(12) United States Patent
Chauhan et al.

(10) Patent No.: US 10,111,598 B2
(45) Date of Patent: Oct. 30, 2018

(54) SYSTEM AND METHOD FOR FOCAL SOURCE IDENTIFICATION

(71) Applicant: University Health Network, Toronto (CA)

(72) Inventors: Vijay Singh Chauhan, Toronto (CA); Sigfus Gizurarson, Reykjavik (IS); Rupin Haily Dalvi, Toronto (CA)

(73) Assignee: University Health Network, Toronto (CA)

( * ) Notice: Subject to any disclaimer, the term of this patent is extended or adjusted under 35 U.S.C. 154(b) by 5 days.

(21) Appl. No.: 15/126,634

(22) PCT Filed: Mar. 31, 2015

(86) PCT No.: PCT/CA2015/000202
§ 371 (c)(1),
(2) Date: Sep. 16, 2016

(87) PCT Pub. No.: WO2015/149153
PCT Pub. Date: Oct. 8, 2015

(65) Prior Publication Data
US 2017/0079539 A1  Mar. 23, 2017

Related U.S. Application Data

(60) Provisional application No. 61/972,894, filed on Mar. 31, 2014.

(51) Int. Cl.
*A61B 5/04* (2006.01)
*A61B 5/0456* (2006.01)
(Continued)

(52) U.S. Cl.
CPC .......... *A61B 5/04012* (2013.01); *A61B 5/044* (2013.01); *A61B 5/046* (2013.01);
(Continued)

(58) Field of Classification Search
CPC ... A61B 5/04012; A61B 5/046; A61B 5/0456; A61B 5/0452
See application file for complete search history.

(56) References Cited

U.S. PATENT DOCUMENTS 5,772,604 A    6/1998  Langberg et al.
8,428,700 B2   4/2013  Harlev et al.
(Continued)

FOREIGN PATENT DOCUMENTS

CA    2942904 A1    10/2015
EP    3125757       2/2017
(Continued)

OTHER PUBLICATIONS

Stiles, et al., "The Effect of Electrogram Duration on Quantification of Complex Fractionated Atrial Electrograms and Dominant Frequency", J Cardiovasc Electrophysiol., 2008, 19(3): 252-258.
(Continued)

*Primary Examiner* — William Levicky
(74) *Attorney, Agent, or Firm* — Bereskin & Parr LLP/S.E.N.C.R.L., s.r.l.; Tony Orsi; T. Cameron Gale

(57) ABSTRACT

Various embodiments are described herein for a system, method, and device for identifying focal source locations of electrophysiological activity in an organ. The system, method and device may also be used to guide catheter ablation of the organ. An electrogram signal can be obtained from a location in the organ, and it can be determined if the electrogram is periodic and, if so, the corresponding periodicity cycle length. A plurality of peaks associated with the cycle length can be identified. The location can be identified as a focal source location when the periodicity cycle length and the plurality of peaks have focal source characteristics.
(Continued)

Methods are also described for identifying a direction of wave propagation and identifying multiple periodicities within an electrogram signal.

26 Claims, 41 Drawing Sheets

(51) Int. Cl.
  *A61B 5/046* (2006.01)
  *A61B 5/0452* (2006.01)
  *A61B 5/044* (2006.01)
  *A61B 18/14* (2006.01)
  *A61B 5/0408* (2006.01)

(52) U.S. Cl.
  CPC .......... *A61B 5/0452* (2013.01); *A61B 5/0456* (2013.01); *A61B 18/1492* (2013.01); *A61B 5/04085* (2013.01)

(56) References Cited

U.S. PATENT DOCUMENTS

| | | |
|---|---|---|
| 8,478,393 B2 | 7/2013 | Ramanathan et al. |
| 2009/0299424 A1 | 12/2009 | Narayan |
| 2010/0094274 A1 | 4/2010 | Narayan et al. |
| 2010/0234909 A1 | 9/2010 | Russell |
| 2011/0251505 A1 | 10/2011 | Narayan et al. |
| 2013/0006131 A1 | 1/2013 | Narayan et al. |
| 2013/0066221 A1 | 3/2013 | Ryu et al. |
| 2014/0005562 A1 | 1/2014 | Bunch et al. |
| 2014/0031708 A1 | 1/2014 | Lo et al. |
| 2014/0088395 A1* | 3/2014 | Dubois .................. A61B 5/044 600/382 |
| 2017/0311835 A1* | 11/2017 | Narayan .............. A61B 5/7221 |

FOREIGN PATENT DOCUMENTS

| | | |
|---|---|---|
| WO | 2007/059362 A2 | 5/2007 |
| WO | 2008035070 A2 | 3/2008 |
| WO | 2015/149153 A1 | 10/2015 |

OTHER PUBLICATIONS

Jacobsen, "Auto-Threshold Peak Detection in Physiological Signals", In Proceedings of the 23rd Annual International Conference of the IEEE, Al-Ain, United Arab Emirates, Engineering in Medicine and Biology Society, 2001, 3: 2194-2195.

Vivó-Truyols, et al., "Automatic program for peak detection and deconvolution of multi-overlapped chromatographic signals—Part I: Peak detection", J. Chromatogr. A, 2005, 1096(1-2): 133-145.

Fortunato, et al., "Generalized Murty's Algorithm With Application to Multiple Hypothesis Tracking", In 10th International Conference on Informational Fusion, IEEE, 2007, 8 pages.

O'Neill, et al., "The stepwise ablation approach for chronic atrial fibrillation—Evidence for a cumulative effect", J Interv Card Electrophysiol., 2006, 16(3):153-167.

Brooks, et al., "Outcomes of long-standing persistent atrial fibrillation ablation: A systematic review", Heart Rhythm, 2010, 7(6): 835-846.

Singh, et al., "A robust R-peak Detection Algorithm using Wavelet Packets", Int J Comput Appl., 2011, 36(5): 37-43.

Umapathy, et al., "Phase Mapping of Cardiac Fibrillation", Circ Arrhythm Electrophysiol, 2010, 3(1): 105-114.

Narayan, et al., "Treatment of Atrial Fibrillation by the Ablation of Localized Sources: The Conventional Ablation for Atrial Fibrillation With or Without Focal Impulse and Rotor Modulation (CONFIRM) Trial," J Am Coll Cardiol. 2012, 60(7): 628-636.

Ghoraani, et al., "Localized rotational activation in the left atrium during human atrial fibrillation: Relationship to complex fractionated atrial electrograms and low-voltage zones", Heart Rhythm, 2013, 10(12): 1830-1838.

Saul, et al., "Periodic Component Analysis: An Eigenvalue Method for Representing Periodic Structure in Speech", In 14th Annual Neural Information Processing Systems Conference, NIPS 2000, Advances in Neural Information Processing Systems, 2001, 13, 7 pages.

Sameni, et al., "Multichannel Electrocardiogram Decomposition Using Periodic Component Analysis", IEEE Trans Biomed Eng., 2008, 55(8): 1935-1940.

Fischer, et al., "On Computing Dominant Frequency From Bipolar Intracardiac Electrograms", IEEE Trans Biomed Eng., 2007, 54(1): 165-169.

Benitez, et al., "The use of the Hilbert transform in ECG signal analysis", Comput Biol Med., 2001, 31(5): 399-406.

Lin, "QRS Feature Extraction Using Linear Prediction", IEEE Trans Biomed Eng., 1989, 36(10): 1050-1055.

De Bakker, et al., "The Pathophysiologic Basis of Fractionated and Complex Electrograms and the Impact of Recording Techniques on Their Detection and Interpretation", Circ Arrhythm Electrophysiol., 2010, 3(2): 204-213.

Mehta, et al., "K-means algorithm for the detection and delineation of QRS-complexes in Electrocardiogram", IRBM 2010, 31(1): 48-54.

Narayan, et al., "Clinical Mapping Approach to Diagnose Electrical Rotors and Focal Impulse Sources for Human Atrial Fibrillation", J Cardiovasc Electrophysiol., 2012, 23(5): 447-454.

Slimane, et al., "QRS complex detection using Empirical Mode Decomposition", Digit Signal Proc., 2010, 20(4): 1221-1228.

Coast, et al., "An Approach to Cardiac Arrhythmia Analysis Using Hidden Markov Models", IEEE Trans Biomed Eng., 1990, 37(9): 826-836.

Scholkmann, et al., "An Efficient Algorithm for Automatic Peak Detection in Noisy Periodic and Quasi-Periodic Signals", Algorithms, 2012, 5(4): 588-603.

Ng et al., "Iterative Method to Detect Atrial Activations and Measure Cycle Length From Electrograms During Atrial Fibrillation", IEEE IEEE Trans Biomed Eng., 2014, 61(2): 273-278.

Sugavaneswaran, et al., "Robust approach for evaluating periodicity in human atrial fibrillation bipolar electrograms", In Digital Signal Processing and Signal Processing Education Meeting DSP/SPE, IEEE, 2013, pp. 90-95.

Dalvi, et al., "Reviving the maximum likelihood method for detecting dominant periodicities from near-periodic signals", In Digital Signal Processing and Signal Processing Education Meeting (DSP/SPE), San Francisco, IEEE, 2013, pp. 256-261.

Sahadevan, et al., "Epicardial Mapping of Chronic Atrial Fibrillation in Patients—Preliminary Observations", Circ., 2004, 110(21): 3293-3299 .

Pandit, et al., "Rotors and the Dynamics of Cardiac Fibrillation", Circ Res., 2013, 112(5): 849-862.

Lee, et al., "High Density Mapping of Atrial Fibrillation During Vagal Nerve Stimulation in the Canine Heart: Restudying the Moe Hypothesis", J Cardiovasc Electrophysiol., 2013, 24: 328-335.

International Preliminary Report on Patentability dated Oct. 4, 2016 in corresponding International Patent Application No. PCT/CA2015/000202.

Vaquero, et al., "Cardiac Fibrillation: From Ion Channels to Rotors in the Human Heart", Heart Rhythm, 2008, 5(6): 872-879.

Sanders, et al., "Spectral Analysis Identifies Sites of High-Frequency Activity Maintaining Atrial Fibrillation in Humans", Circulation, 2005, 112(6): 789-797.

Gizurarson, et al., "Focal Sources Identified by Periodic Component Analysis Predicts the Need for Ablation Outside the Pulmonary Veins in Patients Undergoing Atrial Fibrillation Catheter Ablation", Heart Rhythm, 2014, 11(5): S27-S28.

Sethares, et al., "Periodicity Transforms," Signal Processing, IEEE Transactions on Signal Processing, 1999, 47(11): 2953-2964.

Benedetto, et al., "Periodic Wavelet Transforms and Periodicity Detection", SIAM J Appl Math., 2006, 62(4): 1329-1368.

Ng, et al., "Understanding and Interpreting Dominant Frequency Analysis of AF Electrograms", Journal of Cardiovascular Electrophysiology, 2007, 18(6): 680-685.

Extended European Search Report dated Oct. 24, 2017 in corresponding EP Patent Application No. 15773870.9.

(56) References Cited

OTHER PUBLICATIONS

Narayan, et al., "Evaluating Fluctuations in Human Atrial Fibrillatory Cycle Length Using Monophasic Action Potentials", PACE, 2006, 29(11): 1209-1218.

* cited by examiner

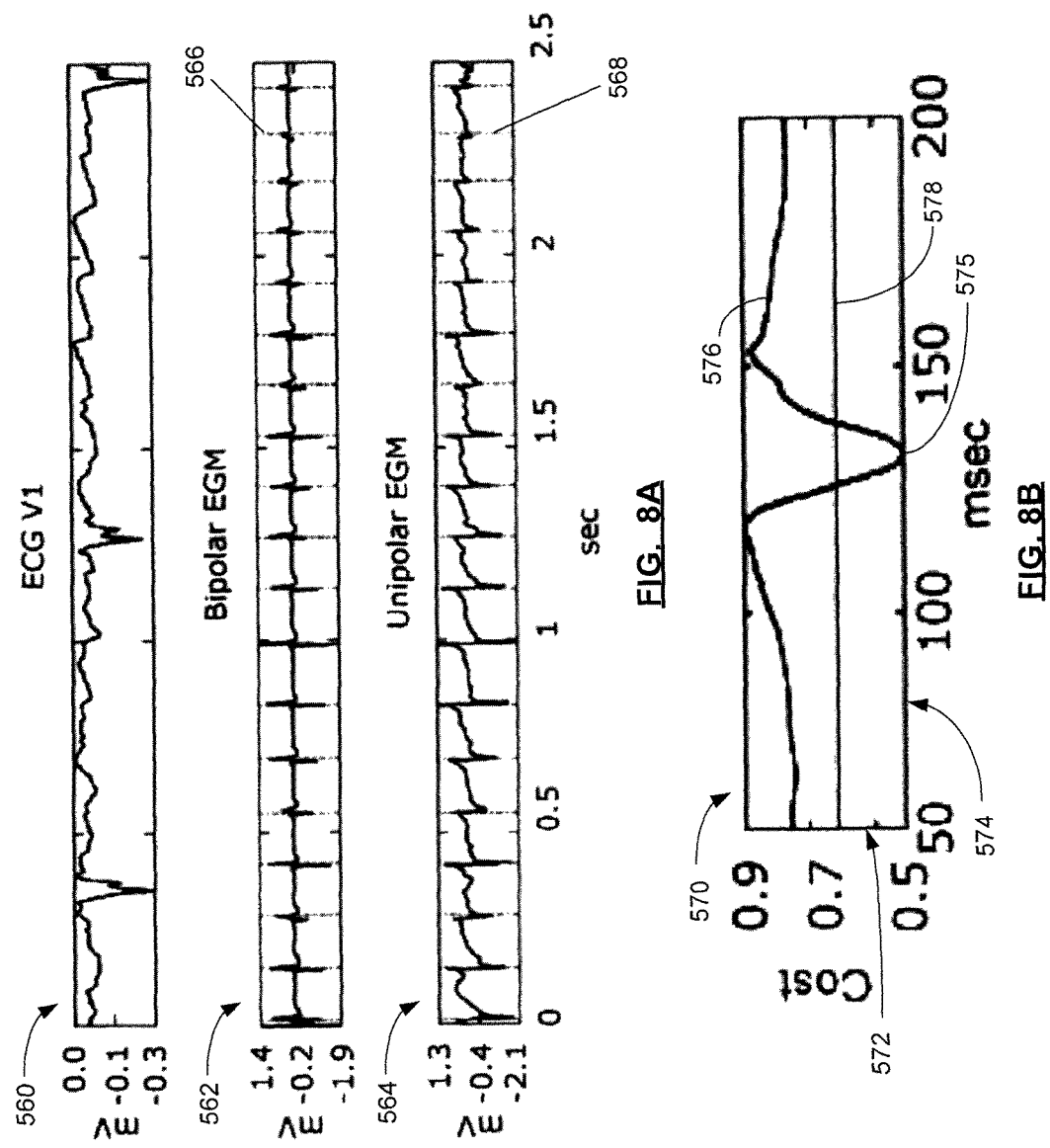

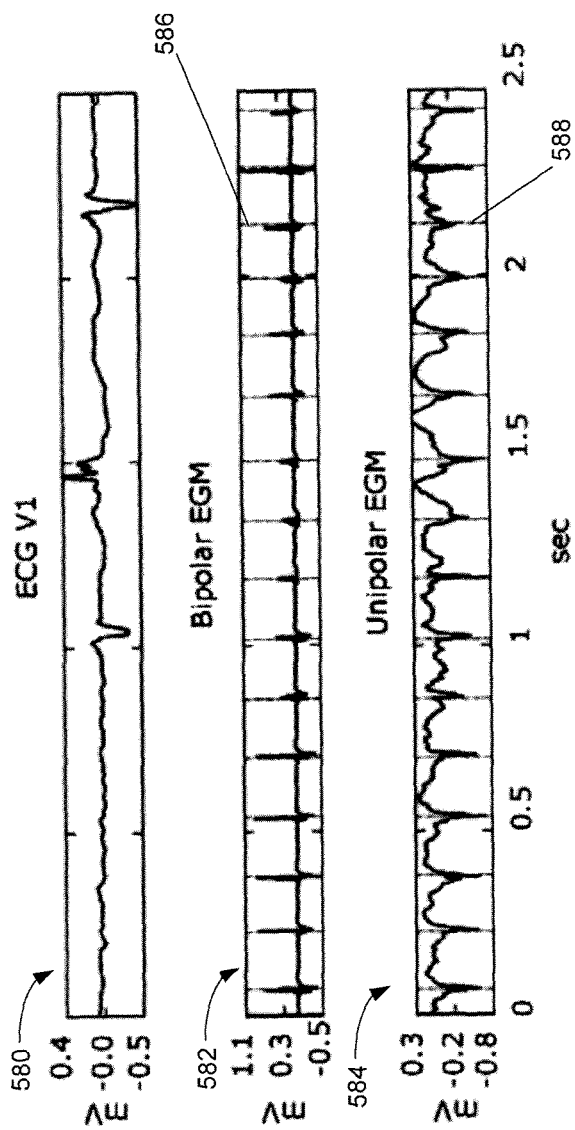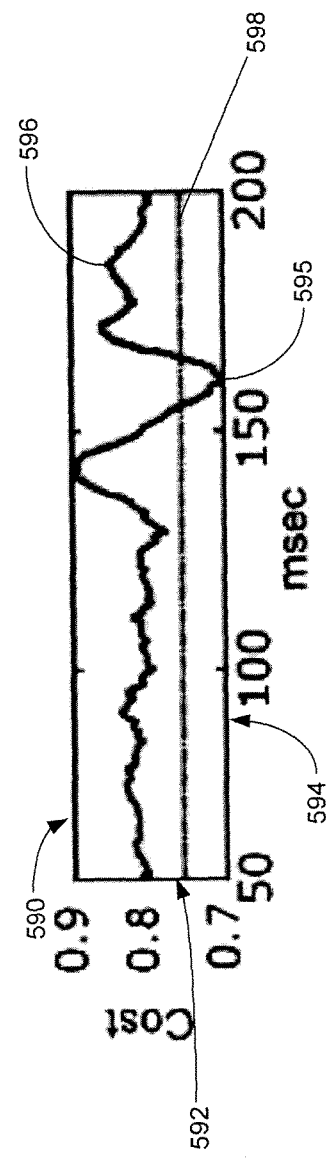
FIG. 8C
FIG. 8D (a) Atrium with few periodic regions (b) Atrium with many periodic regions

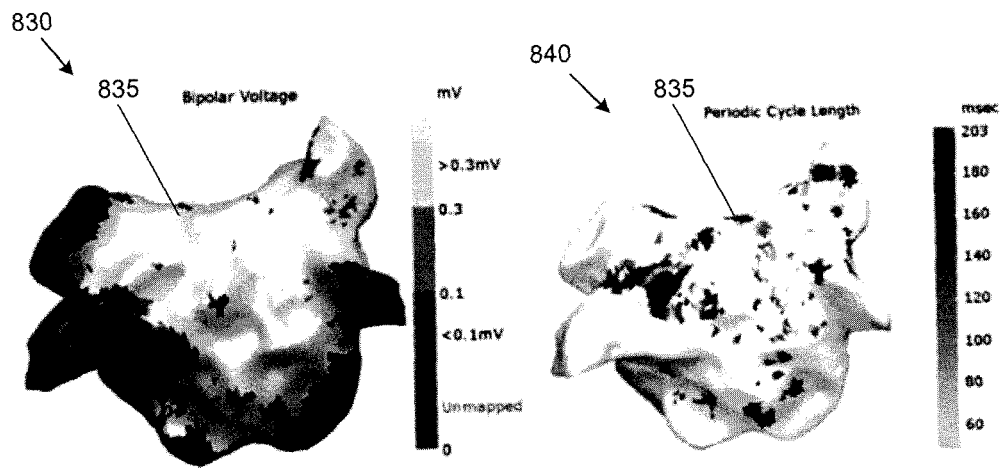
FIG. 14A  FIG. 14B
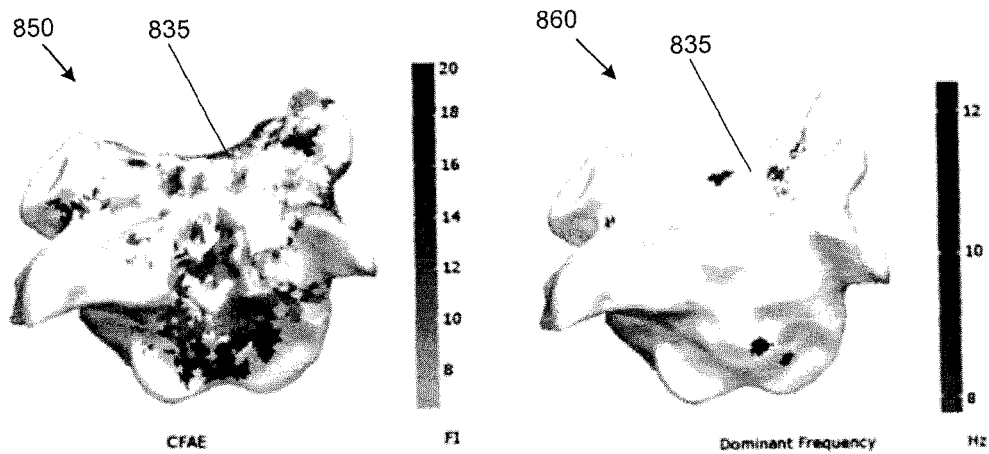
FIG. 14C  FIG. 14D

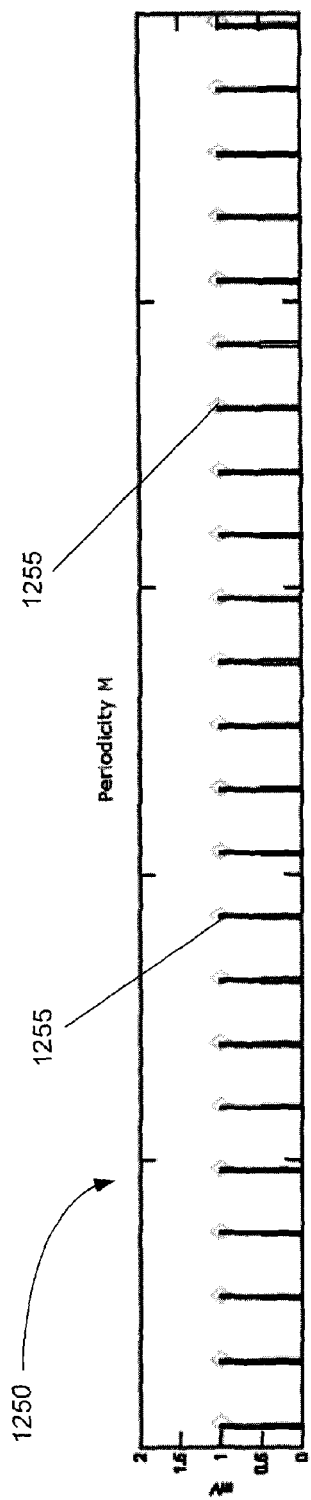
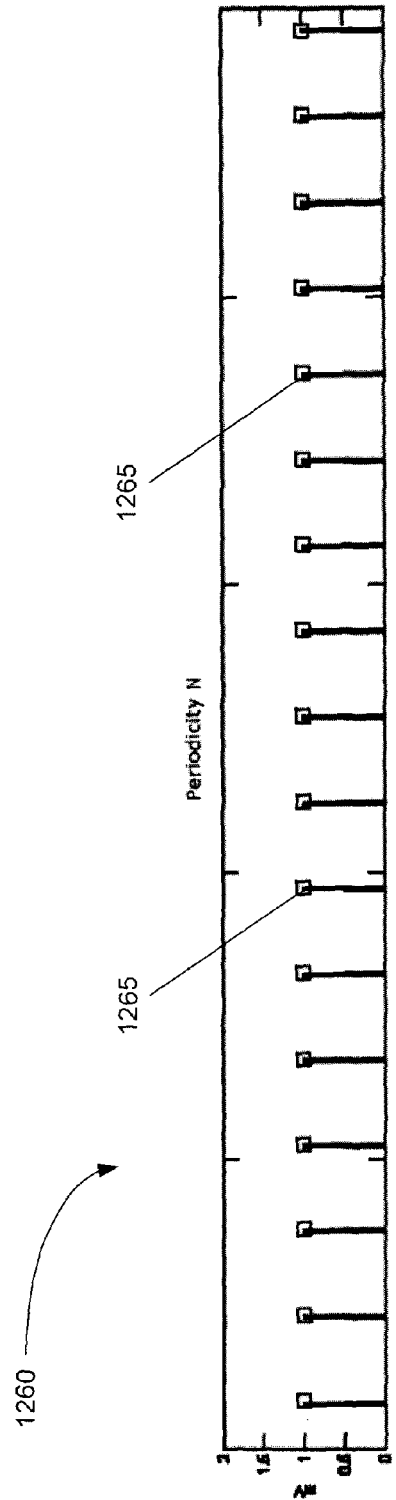
FIG. 21A
FIG. 21B

SYSTEM AND METHOD FOR FOCAL SOURCE IDENTIFICATION

CROSS-REFERENCE TO RELATED APPLICATION

This application claims the benefit of U.S. Provisional Patent Application No. 61/972,894, filed Mar. 31, 2014 and PCT Patent Publication No. WO 2015/149153 filed Mar. 31, 2015; the entire contents of Patent Application No. 61/972,894 and Patent Publication No. WO 2015/149153 are hereby incorporated by reference.

FIELD

The various embodiments described herein generally relate to a system and method for identifying focal source locations of electrophysiological activity in an organ.

BACKGROUND

Abnormal electrical rhythms in the heart or brain can arise from repetitively firing electrical impulses, sometimes known as focal sources (FS) or triggers. These electrical impulses generate electrical propagating waves in the heart or brain which spread out and collide with one another to create chaotic electrical rhythms. Locating these focal sources and triggers is often essential to treat these abnormal electrical rhythms.

Atrial fibrillation (AF) is a common cardiac arrhythmia characterized by chaotic electric activity in the heart. Computational, animal and human studies have indicated that AF can, in some instances, be driven by discrete periodic focal sources with high frequency. However, finding these focal sources remains a challenge.

A common therapy for AF is catheter ablation where heat energy is delivered to the atrium in order to stop AF. However, standard AF catheter ablation does not work well despite extensive burning in the atrium because the ablation sites may not reliably target the focal sources or triggers that cause AF. Thus, a significant number of patients develop AF recurrence after ablation and need another ablation procedure. Given the prevalence of AF in society, its disabling health consequences, and the constraints on healthcare costs, the success rate of AF ablation must be improved.

SUMMARY OF VARIOUS EMBODIMENTS

In a broad aspect, at least one embodiment described herein provides a method of identifying one or more focal source locations of electrophysiological activity for an organ. The method comprises receiving a first electrical signal set obtained from a first location of the organ; determining that the first electrical signal set is periodic; identifying a periodicity cycle length of the first electrical signal set if the first electrical signal set is periodic; identifying a plurality of peaks in the first electrical signal set that are associated with the identified periodicity cycle length; and identifying the first location in the organ as a first focal source location of the one or more focal source locations when the identified periodicity cycle length and the identified plurality of peaks have focal source characteristics.

In another broad aspect, at least one embodiment described herein provides a computer readable medium comprising a plurality of instructions that are executable on a microprocessor of a device for adapting the device to implement a method of identifying one or more focal source locations of electrophysiological activity for an organ, wherein the method is defined herein.

In another broad aspect, at least one embodiment described herein provides an electronic device for identifying one or more focal source locations of electrophysiological activity for an organ. The electrical device comprises an input for receiving a first electrical signal set obtained from a first location of the organ; a processing unit coupled to the input to receive the first electrical signal set and configured to determine if the first electrical signal set is periodic; to identify a periodicity cycle length of the first electrical signal set if the signal is periodic; to identify a plurality of peaks in the first electrical signal set that are associated with the identified periodicity cycle length; and to identify the first location in the organ as a first focal source location of the one or more focal source locations when the identified periodicity cycle length and the identified plurality of peaks have focal source characteristics; and an output coupled to the processing unit to provide an indication of any identified focal source locations for the organ.

In another broad aspect, at least one embodiment described herein provides a use of a method of identifying one or more focal source locations of electrophysiological activity for an organ in order to guide catheter ablation of the at least one of the one or more focal source locations, wherein the method is defined herein.

In another broad aspect, at least one embodiment described herein provides a use of a device for identifying one or more focal source locations of electrophysiological activity of an organ in order to guide catheter ablation of at least one of the one or more focal source locations, wherein the device is defined herein.

In another broad aspect, at least one embodiment described herein provides a system for identifying one or more focal source locations of electrophysiological activity for an organ and guiding catheter ablation of the one or more focal source locations, wherein the system comprises a device as defined herein and an ablation unit for performing the catheter ablation.

In another broad aspect, at least one embodiment described herein provides a method of identifying a direction of a propagating wave based on one or more focal source locations of electrophysiological activity for an organ. The method comprises receiving a plurality of electrical signal sets obtained substantially simultaneously from a plurality of locations of the organ; identifying a first subset of the plurality of electrical signal sets having periodicity; determining periodicity cycle lengths for the first subset of electrical signal sets that have periodicity; identifying a second subset of electrical signal sets having similar periodicity cycle lengths in the first subset of electrical signal sets; identifying a plurality of valid peaks for each electrical signal set in the second subset of electrical signal sets; determining if the plurality of valid peaks have propagating wave characteristics; and sorting the valid peaks to identify the direction of the propagating wave if the plurality of valid peaks have propagating wave characteristics.

In another broad aspect, at least one embodiment described herein provides a computer readable medium comprising a plurality of instructions that are executable on a microprocessor of a device for adapting the device to implement a method of identifying a direction of a propagating wave based on one or more focal source locations of electrophysiological activity for an organ, wherein the method is defined herein.

In another broad aspect, at least one embodiment described herein provides an electronic device for identifying a direction of a propagating wave based on one or more focal source locations of electrophysiological activity for an organ. The electronic device includes an input for receiving a plurality of electrical signal sets obtained substantially simultaneously from a plurality of locations of the organ. The electronic device also includes a processing unit coupled to the input to receive the first electrical signal set and configured to identify a first subset of the plurality of electrical signal sets having periodicity; to determine periodicity cycle lengths for the first subset of electrical signal sets that have periodicity; to identify a second subset of electrical signal sets having similar periodicity cycle lengths in the first subset of electrical signal sets; to identify a plurality of peaks for each electrical signal set in the second subset of electrical signal sets; and to identify the direction of the propagating wave if the plurality of peaks in the second subset of electrical signal sets have propagating wave characteristics. The electronic device also includes an output coupled to the processing unit to provide an indication of the direction of the propagating wave for the organ.

In another broad aspect, at least one embodiment described herein provides a use of a method of identifying a direction of a propagating wave based on one or more focal source locations of electrophysiological activity for an organ in order to guide catheter ablation of at least one of the one or more focal source locations, wherein the method is defined herein.

In another broad aspect, at least one embodiment described herein provides a use of a device for identifying a direction of a propagating wave based on one or more focal source locations of electrophysiological activity for an organ in order to guide catheter ablation of at least one of the one or more focal source locations, wherein the device is defined herein.

In another broad aspect, at least one embodiment described herein provides a system for identifying a direction of a propagating wave based on one or more focal source locations of electrophysiological activity for an organ and guiding catheter ablation of the one or more focal source locations, wherein the system comprises an electronic device defined herein and an ablation unit for performing the catheter ablation.

In another broad aspect, at least one embodiment described herein provides a method of identifying multiple significant periodicities in an electrical signal set representing electrophysiological activity for an organ. The method comprises receiving the electrical signal set obtained from a location of the organ; identifying a periodicity cycle length of the electrical signal set; determining a plurality of peaks in the electrical signal set that are associated with the identified periodicity cycle length; noting the identified periodicity cycle length; generating an updated electrical signal set by removing information associated with the identified periodicity cycle length; and repeating the identifying, determining, noting and generating acts until no periodicity is detected in the updated electrical signal set.

In another broad aspect, at least one embodiment described herein provides a computer readable medium comprising a plurality of instructions that are executable on a microprocessor of a device for adapting the device to implement a method of identifying multiple significant periodicities in an electrical signal set representing electrophysiological activity for an organ, wherein the method is defined herein.

In another broad aspect, at least one embodiment described herein provides an electronic device for identifying multiple significant periodicities in an electrical signal set representing electrophysiological activity for an organ. The electronic device includes an input for receiving the electrical signal set obtained from a location of the organ. The electronic device also includes a processing unit coupled to the input to receive the first electrical signal set and configured to identify a periodicity cycle length of the electrical signal set; to determine a plurality of peaks in the electrical signal set that are associated with the identified periodicity cycle length; to note the identified periodicity cycle length; to generate an updated electrical signal set by removing information associated with the identified periodicity cycle length; and to repeat the identifying, determining, noting and generating acts until no periodicity is detected in the updated electrical signal set. The electronic device also includes an output coupled to the processing unit to provide an indication of all of the multiple significant periodicities in the electrical signal set.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described.

FIG. 8A is a diagram illustrating a unipolar electrogram, a bipolar electrogram and an ECG lead V1 received from a first recording site in the left atrium (LA) of a patient with visually apparent periodic bipolar electrograms.

FIG. 8B is a diagram illustrating a periodicity cost function corresponding to the bipolar electrogram of FIG. 8A.

FIG. 8C is a diagram illustrating a unipolar electrogram, a bipolar electrogram and an ECG lead V1 received from a second recording site in the left atrium of another patient with visually apparent periodic bipolar electrograms.

FIG. 8D is a diagram illustrating a periodicity cost function corresponding to the bipolar electrogram of FIG. 8C.

FIG. 14A is a diagram illustrating an example of a 3D map of the left atrium of a patient with the voltage of the corresponding bipolar electrogram highlighted.

FIG. 14B is a diagram illustrating another example of the 3D map of the left atrium of the patient shown in FIG. 14A with the periodic regions highlighted.

FIG. 14C is a diagram illustrating another example of the 3D map of the left atrium of the patient shown in FIG. 14A with regions of complex fractionated atrial electrocardiograms highlighted.

FIG. 14D is a diagram illustrating another example of the 3D map of the left atrium of the patient shown in FIG. 14A with regions having dominant frequencies highlighted.

FIG. 21A is a diagram illustrating an example plot of a simulated electrogram signal with a periodic signal having a first cycle length.

FIG. 21B is a diagram illustrating an example plot of a simulated electrogram signal with a periodic signal having a second cycle length.

Figure 1:
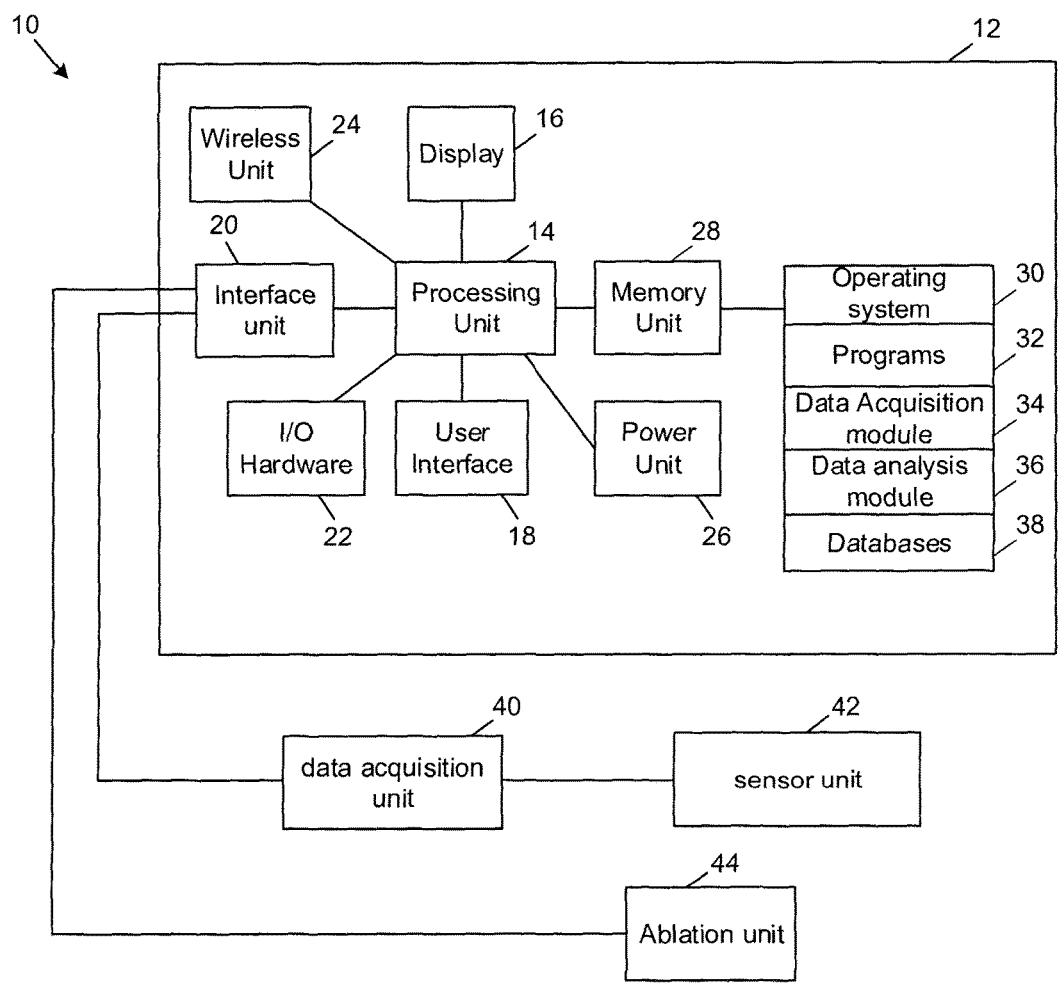
FIG. 1 is a block diagram of an example embodiment of a system that can perform focal source and trigger identification methods to identify focal source locations of electrophysiological activity for an organ.

Further aspects and features of the embodiments described herein will appear from the following description taken together with the accompanying drawings.

DETAILED DESCRIPTION OF THE EMBODIMENTS

Various apparatuses or methods will be described below to provide an example of an embodiment of the claimed subject matter. No embodiment described below limits any claimed subject matter and any claimed subject matter may cover methods or apparatuses that differ from those described below. The claimed subject matter is not limited to apparatuses or methods having all of the features of any one apparatus or methods described below or to features common to multiple or all of the apparatuses or methods described below. It is possible that an apparatus or methods described below is not an embodiment that is recited in any claimed subject matter. Any subject matter disclosed in an apparatus or methods described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are various example embodiments of a system and method that can be used for identifying the periodicity cycle length and corresponding peaks of an electrogram (EGM) signal recorded at a location in an organ, which may be used for various goals, including focal source locations which may then be used as identifying targets for AF ablation. Although the application focuses on EGM signal and focal sources for AF, it should be noted that the techniques described herein may be adapted for use with locating other focal source locations of electrophysiological activity such as, but not limited to, locating focal sources for epileptic seizures, for example.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described in accordance with the teachings herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Referring now to FIG. 1, shown therein is a block diagram of an example embodiment of a focal source identification system 10 that can be used to identify one or more focal source locations of electrophysiological activity for an organ. The system 10 includes an operator unit 12, a data acquisition unit 40, a sensor unit 42, and an ablation unit 44. The system 10 is provided as an example and there can be other embodiments of the system 10 with different components or a different configuration of the components described herein. The system 10 further includes several power supplies (not all shown) connected to various components of the system 10 for providing power thereto as is commonly known to those skilled in the art. In general, a user may interact with the operator unit 12 to record electrical signal sets, such as bipolar and unipolar EGM data from a subject or a patient, and then perform data analysis on the recorded data to identify focal source locations of electrophysiological activity for an organ of the patient.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, a data acquisition module 34, a data analysis module 36, and one or more databases 38. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power depending on the configuration, purposes and requirements of the system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

Figure 19A:
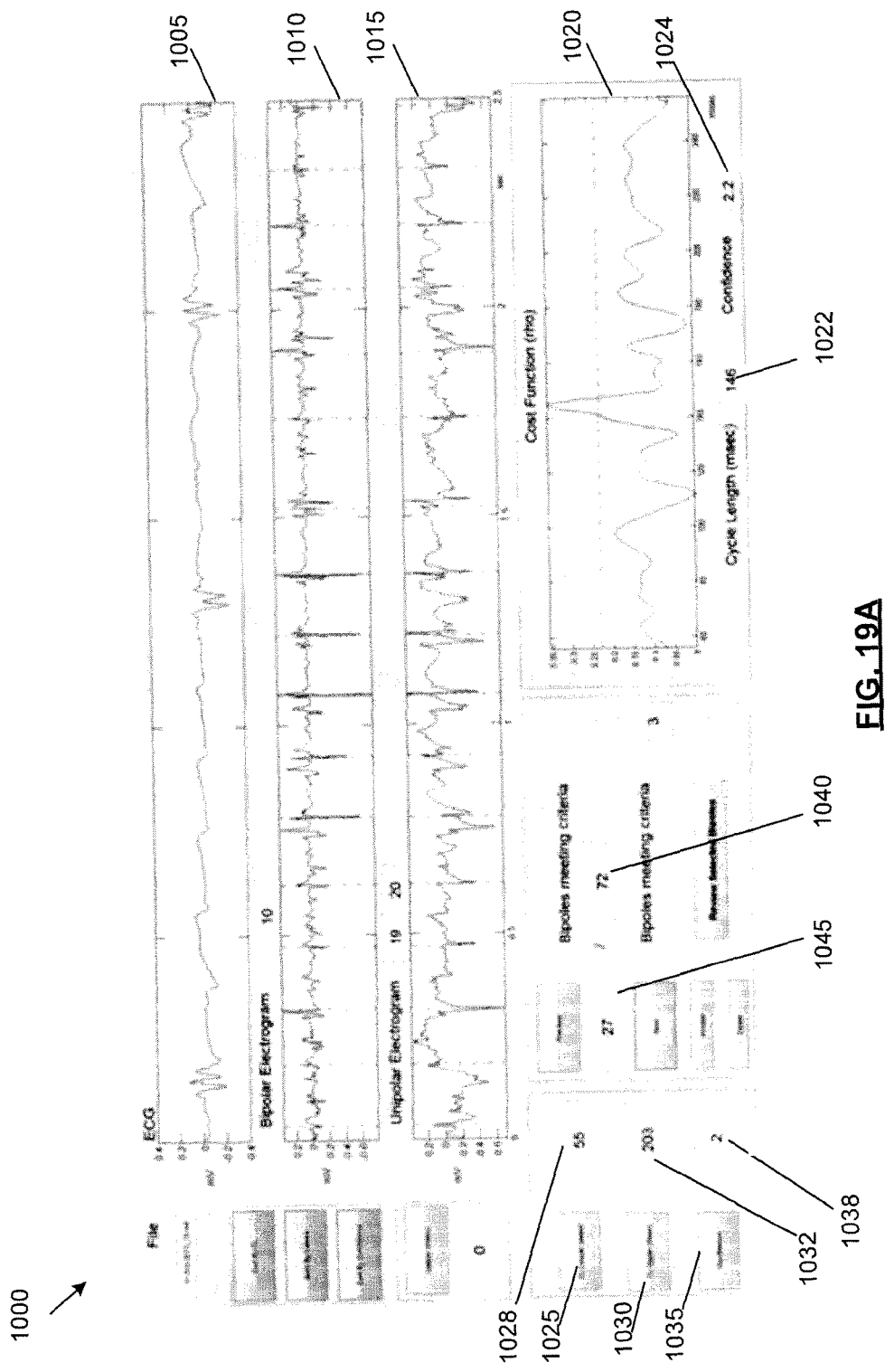
FIG. 19A is a diagram illustrating an example embodiment of a graphical user interface that may be displayed by the system of FIG. 1 when performing a focal source location method on electrogram data.
Figure 19B:
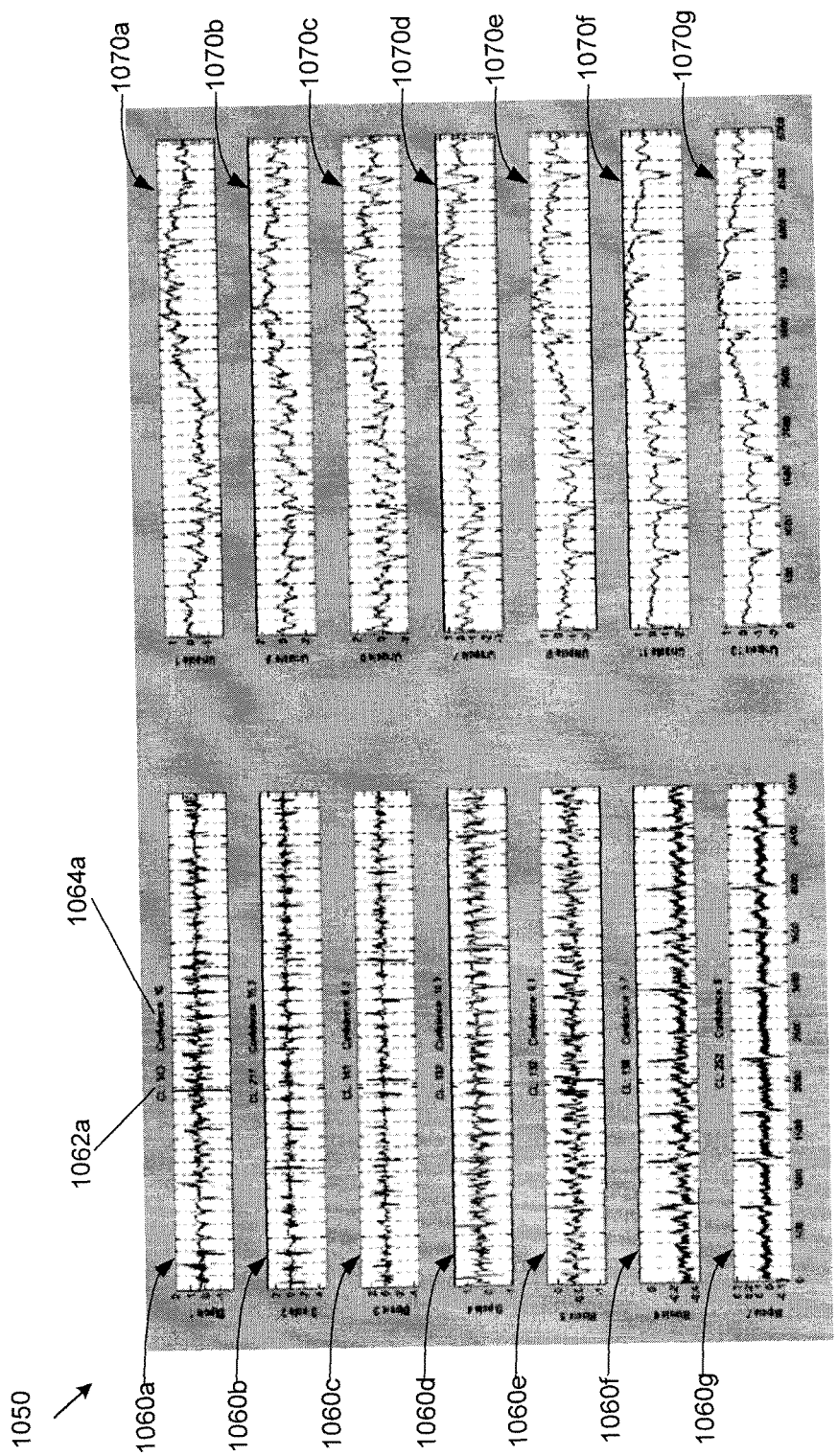
FIG. 19B is a diagram illustrating another example embodiment of a graphical user interface that may be displayed by the system of FIG. 1 when performing a focal source location method on electrogram data.
Figure 19C:
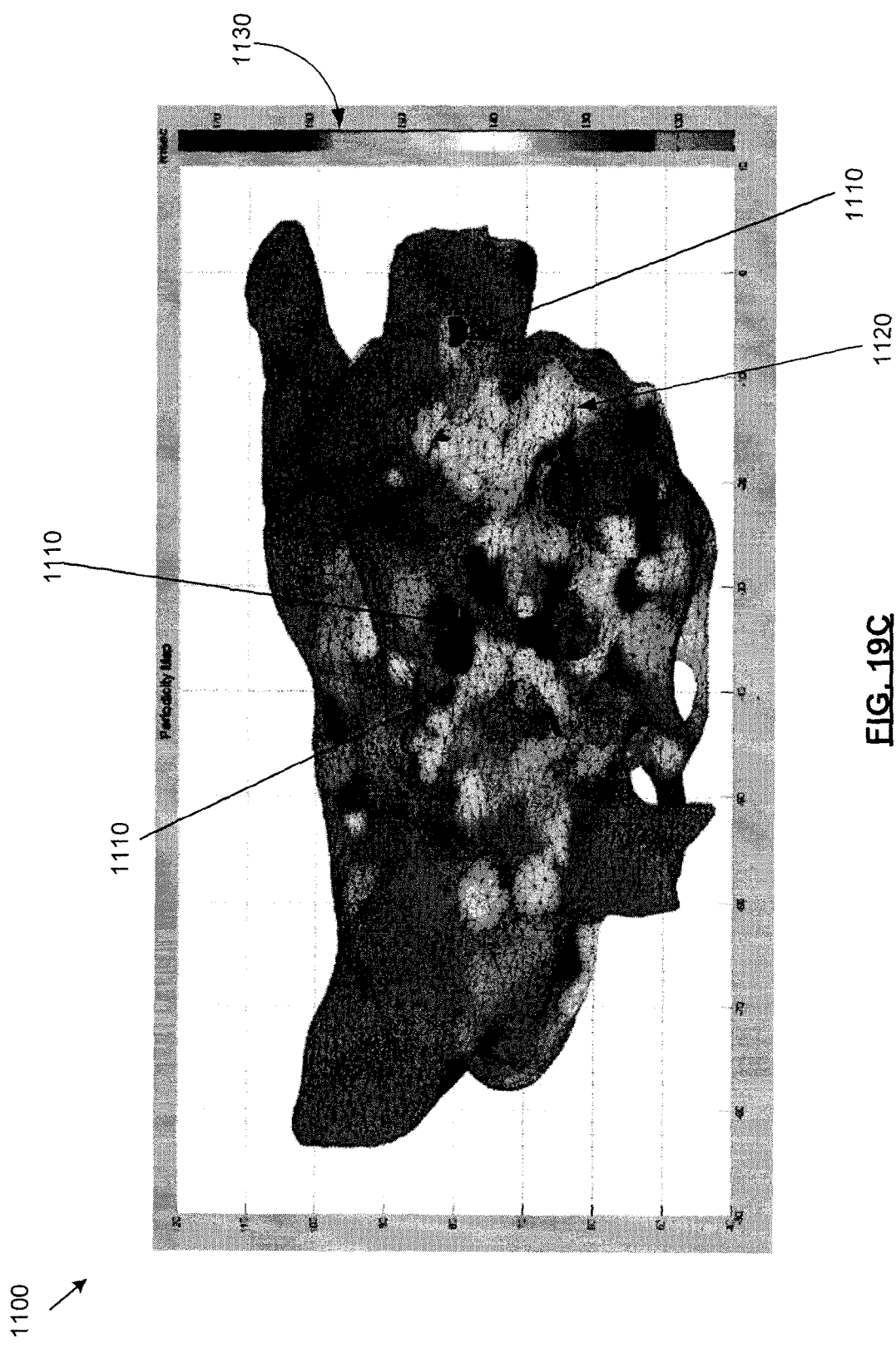
FIG. 19C is a diagram illustrating another example embodiment of a graphical user interface that may be displayed by the system of FIG. 1 when performing a focal source location method on electrogram data.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like. Examples of graphical user interfaces that may be shown to a user on the display 16 are shown in FIGS. 19A-C.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet, Local Area Network (LAN), Ethernet, Firewire, modem or digital subscriber line connection. Various combinations of these elements can be incorporated within the interface unit 20.

The I/O hardware 22 is optional and can include, but is not limited to, at least one of a microphone, a speaker and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, viewing and manipulating data, adjusting parameters for data analysis as well as sending messages as the case may be.

The data acquisition module 34 is used to obtain electrical signal sets from one or more locations in a patient or a subject, and more particularly from one or more locations at an organ of interest for the patient or subject. For example, in some embodiments, the data acquisition module 34 is operable to acquire signals from at least one region in the atrium of a patient's heart. The data acquisition module 34 is coupled to the data acquisition unit 40 and the sensor unit 42 in order to acquire these signals.

In some cases, the data acquisition module 34 may be used to obtain electrical signal sets from a single location at an organ of interest. In other cases, the data acquisition module 34 may be used to obtain electrical signal sets from multiple locations simultaneously depending on the sensor unit 42 that is used. For example, in order to obtain electrical signal sets from multiple locations simultaneously, the data acquisition unit 40 may use a sensor unit 42 having a multi-electrode catheter.

Each electrical signal set obtained by the data acquisition module 34 can include bipolar and unipolar EGM from a region of electrically active tissue, such as the atrium and ventricle of a patient's heart, for example. In some cases, the electrical signal sets may also include the surface ECG lead signals obtained from the patient. The electrical signal sets may be preprocessed by the data acquisition unit 40 and transferred to the operator unit 12 through interface unit 20. The preprocessing that is done may include standard signal processing techniques such as, but not limited to, at least one of amplification, filtering and de-noising (e.g. averaging) using parameters that depend on the particular signals that are acquired. The interface unit 20 may be a multichannel data interface coupling the data acquisition unit 40 to the operator unit 12.

It should be noted that while the system 10 is described as having the data acquisition unit 40, the sensor unit 42 and the data acquisition module 34 for acquiring electrophysiological signals, the system 10 may be implemented without these components in an alternative embodiment. This corresponds to situations in which the electrophysiological signals have already been recorded and the system 10 is being used to analyze the recorded electrophysiological signals.

The data analysis module 36 processes the data that is recorded by the data acquisition module 34 in order to determine focal source locations of electrophysiological activity for an organ of interest. For example, the electrophysiological activity may be atrial fibrillation or ventricular fibrillation of a patient's heart. Example embodiments of analysis methods that may be employed by the data analysis module 36 are described in more detail with respect to FIGS. 3 to 6, 20 and 22 to 25. The focal source locations may then be provided as an output consisting of an electronic file or a display image with information in the form of a cardiac map and the like, examples of which are discussed below with references to FIGS. 19A, 19B and 19C. The data analysis module 36 can be coupled to a commercially available mapping system, such as the CARTO™ system manufactured by Biosense Webster, or the NAVX™ system manufactured by St. Jude Medical, to mark locations in the atrium of a patient that have been identified as focal source locations, an example of which is shown in FIG. 19C. Alternatively, the data analysis module 36 may be coupled to a memory element, such as the databases 38 or a storage element, for analyzing previously recorded electrophysiological signals.

In alternative embodiments, the modules 34 and 36 may be combined or may be separated into further modules. The modules 34 and 36 are typically implemented using software, but there may be instances in which they are implemented using FPGA or application specific circuitry. For ease of understanding, certain aspects of the methods described in accordance with the teachings herein are described as being performed by the data analysis module 36. It should be noted, however that these methods are not limited in that respect, and the various aspects of the methods described in accordance with the teachings herein may be performed by other modules for identifying focal source locations.

The databases 38 can be used to store data for the system 10 such as system settings, parameter values, and calibration data. The databases 38 can also store other information required for the operation of the programs 32 or the operating system 30 such as dynamically linked libraries and the like.

The operator unit 12 comprises at least one interface that the processing unit 14 communicates with in order to receive or send information. This interface can be the user interface 18, the interface unit 20 or the wireless unit 24. For instance, the various threshold parameters used by the system 10 in order to perform focal source location and trigger identification may be inputted by a user through the user interface 18 or they may be received through the interface unit 20 from a computing device. The processing unit 14 can communicate with either one of these interfaces as well as the display 16 or the I/O hardware 22 in order to output information related to focal source location, trigger identification and the threshold parameters. In addition, users of the operator unit 12 can communicate information across a network connection to a remote system for storage and/or further analysis in some embodiments. This communication may also include email communication.

The user can also use the operator unit 12 to input information needed for system parameters that are needed for proper operation of the system 10 such as calibration information and other system operating parameters as is known by those skilled in the art. Data that are obtained from tests, as well as parameters used for operation of the system 10, may be stored in the memory unit 28. The stored data may include raw recorded data, preprocessed recorded data as well as processed cardiac map data.

The data acquisition unit 40 comprises hardware and circuitry that is used to record electrical signal sets from a patient or subject. The data acquisition unit 40 may be custom designed or may be implemented using commercially available clinical electrophysiology data acquisition systems and/or three-dimensional electroanatomical mapping systems such as, but not limited to, the CARTO™ system manufactured by Biosense Webster, or the NAVX™ system manufactured by St. Jude Medical, for example.

The sensor unit 42 is used to measure the electrical information from the organ of the patient or subject. The sensor unit 42 may have one or only a few electrodes such as a roving 4-electrode catheter, for example. In other embodiments, the sensor unit 42 can be a multi-electrode sensor such as a 10- or 20-electrode catheter such as the Lasso™ (Biosense Webster), the Pentarray™ (Biosense Webster) and the Spiral™ (St. Jude Medical) that can be used to gather electrical information from discrete areas of the organ. In other embodiments, a multi-electrode contact basket catheter can also be used such as the Constellation™ (Boston Scientific).

The ablation unit 44 is used to ablate focal source locations that have been identified in the patient's organ of interest. The ablation unit 44 can be any suitable ablation unit such as the commercially available Stockert™ ablation generator manufactured by Biosense Webster, for example. The ablation unit 44 may be used to deliver heat energy to the atrium of the patient at identified ablation targets. For example, a medical practitioner may use the methods described in accordance with the teachings herein to identify focal source locations for ablation and to guide ablation of those focal source locations.

Figure 2A:
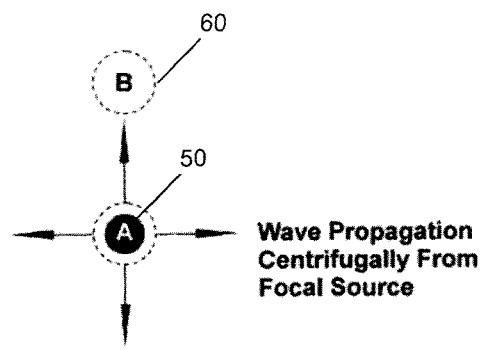
FIG. 2A is a diagram illustrating a first recording site located at a focal source location relative to a second recording site located at a non-focal source location.

Referring now to FIG. 2A, shown therein is a diagram illustrating an example of a first recording location 50 relative to a second recording location 60 in an organ of a patient. The first recording location 50 corresponds to a focal source of electrical activity for the organ. The second recording location 60 corresponds to a recording site located remote from the focal source location. A focal source location is a discrete site in an organ where electrical impulses are generated at high-frequency. Electrical waves then propagate centrifugally away from the focal source location.

Figure 2B:
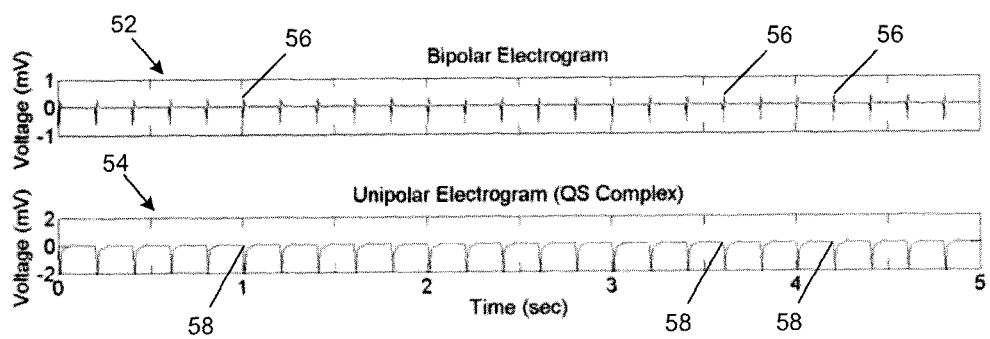
FIG. 2B is a diagram illustrating an example of a bipolar electrogram and a unipolar electrogram recorded at the first recording site shown in FIG. 2A.

Referring now to FIG. 2B, shown therein is a diagram illustrating an example of a bipolar EGM 52 and a unipolar EGM 54 recorded at the first recording location 50 of FIG. 2A. In some cases, a focal source location may be identified by identifying recording locations in an organ with temporally-stable, high-frequency periodic activity in the bipolar EGM and QS morphology in portions of the unipolar EGM that correspond to peaks of the high-frequency periodic activity in the bipolar EGM.

The bipolar EGM 52 corresponding to the first recording location 50 shows regular periodic activity. Peaks 56 can be identified in the bipolar EGM 52 at intervals corresponding to the cycle length of the periodic activity referred to herein as periodicity cycle length. The portions of the unipolar EGM 58 that correspond to the peaks 56 show a QS morphology. Accordingly, the first recording location 50 can be identified as a focal source location for electrical activity in the organ of the patient.

Figure 2C:
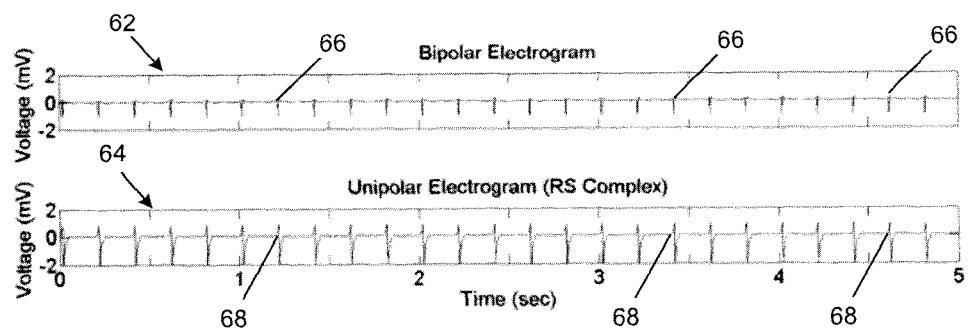
FIG. 2C is a diagram illustrating an example of a bipolar electrogram and a unipolar electrogram recorded at the second recording site shown in FIG. 2A.

Referring now to FIG. 2C, shown therein is a diagram illustrating an example of a bipolar EGM 62 and a unipolar EGM 64 recorded at the second recording location 60 of FIG. 2A. The bipolar EGM 62 shows regular periodic activity at peaks 66. However, the unipolar EGM 62 shows an RS morphology at portions 68 corresponding to the peaks 66. Accordingly, the second recording location 60 would not be identified as a focal source location in the organ of the patient.

Conventional focal source detection methods often identify the periodicity alone or identify all peaks based on a given criterion and estimate the cycle length based on the peak locations. The peak locations may be identified with peak detection techniques that use window-threshold techniques, wavelet transform, Hilbert transform, linear prediction and higher-order statistics analysis, K and fuzzy C-Means clustering, empirical mode decomposition, hidden Markov models and other techniques. Some peak detection methods, such as the automatic multiscale peak detection (AMPD) algorithm and the cycle length iteration (CLI) algorithm attempt non-parametric approaches to improve the robustness and reproducibility of the peak detection method.

Although various methods have been proposed to identify focal source locations, finding focal source locations remains a challenge. Some methods have attempted to characterize an electrogram signal as a whole to identify whether the recording site is a focal source. However, the complex signals generated during AF make it difficult to accurately characterize the signal recorded at a given location.

Many of the periodic peak detection algorithms available assume that all valid peaks are part of the periodic activity. Often, the cycle length will be determined from the identified peaks. However, in real-world applications, many peaks or activations are due to noise and other non-periodic sources not part of the periodic activity of interest.

Many known algorithms may also assume that peak validity is directly proportional to amplitude and may miss genuine peaks that are not local maxima. Many known algorithms are thus prone to degradation in performance if the periodic activity is embedded in other, non-periodic data or in the presence of high levels of noise.

The inventors have discovered that the ability to identify activations or peaks based on periodic activity identified in EGMs may allow focal source locations to be identified with greater accuracy. Such an approach may provide increased accuracy in detecting peaks, particularly in noisy periodic and quasi-periodic signals.

In highly complex signals, such as intracardiac recordings from patients with AF, the peaks corresponding to the periodic signal may not be local maxima. This is because noise, such as aperiodic signals and far-field signals (i.e. signals from remote sites), may sometimes have higher amplitudes than the periodic signals of interest. The inventors have discovered that using an identified periodic cycle length rather than amplitude as the main basis for identifying the peaks in an electrical signal set may thus improve the accuracy of peak detection.

A QS morphology of the unipolar EGM, indicating wave propagation centrifugally away from the recording site, may also be indicative of a focal source in electrophysiology. However, unipolar EGMs recorded during AF are often complex, rendering the identification of the QS morphology a challenge. The inventors have discovered that an approach to examine the morphology of the unipolar EGM recorded during AF based on accurate peak detection may provide increased accuracy in detecting focal source locations. According to the teachings herein, identified peaks may be used to indicate where the morphology of the unipolar EGM should be analyzed to determine whether a focal source location has been identified.

Figure 3:
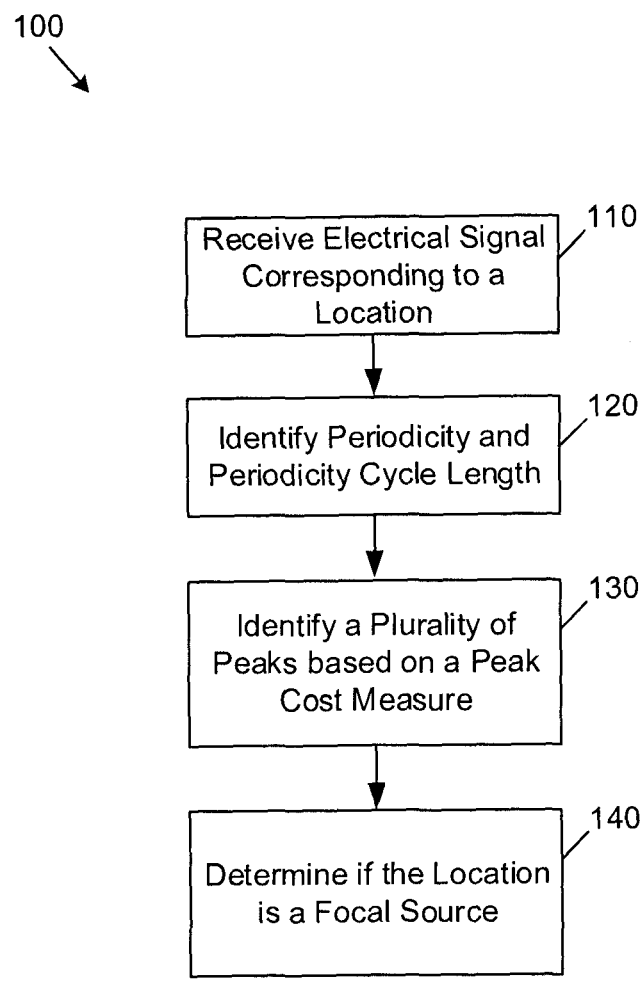
FIG. 3 is a flowchart of an example embodiment of a focal source identification method for analyzing electrophysiological activity from an organ to locate a focal source of electrical activity for the organ.

Referring now to FIG. 3, shown therein is a flowchart of an example embodiment of a focal source identification method 100 that can be used by the system 10 to analyze electrophysiological activity from an organ to locate a focal source of electrical activity for the organ.

At 110, a first electrical signal set corresponding to and obtained from a first location of an organ is received. The electrical signal set may be recorded at the first location using the data acquisition unit 40 and the sensor unit 42, it may be retrieved from a storage element or it may be received from another computing device that may be at a remote location, for example. In some cases, a plurality of additional electrical signal sets may also be obtained with each of the additional electrical signal sets being recorded from different locations in the organ.

In some cases, the plurality of electrical signal sets may be recorded individually at separate times. In other cases, the plurality of electrical signal sets, or subsets of the electrical signal sets may be recorded simultaneously. For example, 10 electrical signals sets may be recorded simultaneously using a sensor unit 42 with a multi-electrode catheter having 10 sensors or a catheter having one sensor may be positioned over time at 10 different locations to obtain the 10 electrical signal sets.

The first electrical signal set generally includes a unipolar EGM and a bipolar EGM corresponding to the electrical signals obtained from the first location. The unipolar EGM and the bipolar EGM may be recorded for various lengths of time as long as the recording time frame is long enough so that enough data suitable for analysis is recorded. In some embodiments where the electrical signal sets are being recorded in real-time, the recording time frame may be selected by a user of the operator unit 12.

At 120, the periodicity and a periodicity cycle length of the first electrical signal set are identified. First it is determined whether there is periodicity in the first electrical signal set and if so the periodicity cycle length is then determined. The periodicity cycle length may be determined using various methods such as, but not limited to, spectral analysis-based methods, auto-correlation-based methods, periodicity transforms, wavelet-based periodicity detection, maximum likelihood-based approaches and other known methods, for example.

Figure 4:
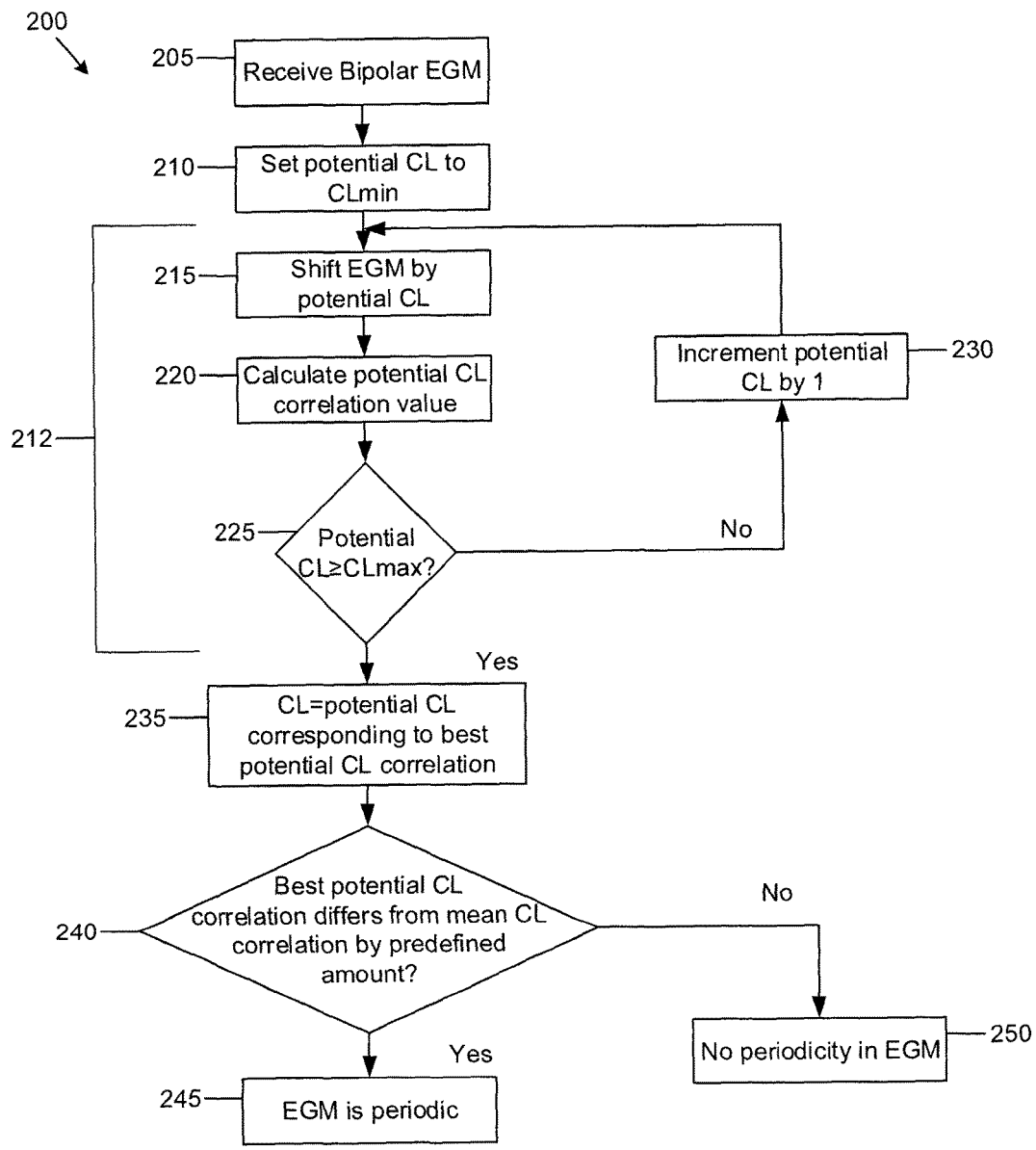
FIG. 4 is a flowchart of an example embodiment of a periodicity cycle length (CL) identification method that can be used by the focal source identification method of FIG. 3.

Referring now to FIG. 4, shown therein is a flowchart of an example embodiment of a periodicity cycle length identification method 200 that can be used in the focal source identification method 100. The periodicity cycle length identification method 200 can be an automated method that may be performed by the data analysis module 36 on an electrical signal set.

At 205, a bipolar EGM corresponding to the first electrical signal set is obtained. In some cases, the first electrical signal set may be preprocessed to exclude data points if the stability of the recording catheter is poor or if only far-field activity is present.

At 210, a potential cycle length CL is obtained from a plurality of potential cycle lengths that may be used to identify the periodicity cycle length of the first electrical signal set. In some cases, the plurality of potential cycle lengths may include a range of potential cycle lengths from a minimum cycle length to a maximum cycle length. The range of potential cycle lengths may be determined based on a range of cycle lengths that correspond physiologically with cycle lengths expected for focal source locations. For example, the potential cycle lengths could range from a minimum potential cycle length of 50 ms to a maximum potential cycle length of 200 ms. In some cases, the potential cycle lengths can be manually adjusted by a user of the operator unit 12. At 210, the potential cycle length may first be set to be the minimum potential cycle length.

The method 200 then begins iterative method 212 in which acts 215-225 may be repeated for several potential cycle lengths. The iterative method 212 is used to determine a plurality of correlation values corresponding to the plurality of potential cycle lengths.

At 215, a first signal portion of the first electrical signal set is identified. In some cases, the first signal portion may be the entire bipolar EGM of the first electrical signal set. A second signal portion from the first electrical signal set is then generated by applying a circular shift to the first signal portion. The amount of the circular shift is the current potential cycle length.

At 220, the correlation value between the first signal portion and the second signal portion for the current potential cycle length is determined. The correlation value can be calculated using any suitable autocorrelation method. In some cases, for example, where one electrical signal set is obtained using a 4-electrode catheter, a standard autocorrelation formula can be used, such as the autocorrelation formula implemented in MATLAB™. In some cases, each correlation value may be determined by applying a cost function to each potential cycle length. For example, the cost function may be a cost function used in periodic component analysis to determine the cost value for a potential cycle length.

At 225, it is determined whether the current potential cycle length is the last potential cycle length to be analyzed. In the embodiment shown in FIG. 4, this is done by determining whether the current potential cycle length is greater than or equal to the maximum potential cycle length. If this determination is not true, the method 200 proceeds to 230. If this determination is true, the method 200 proceeds to 235.

At 230, the current potential cycle length is set to the next potential cycle length to be analyzed. In the embodiment shown in FIG. 4, this is done by incrementing the current potential cycle length by 1. For example, in an embodiment where the potential cycle lengths range from 50 ms to 200 ms, the data analysis module 36 may increment the current potential cycle length by 1 ms at step 230.

At 235, the method 200 determines the periodicity cycle length as the potential cycle length having the optimal correlation value. For example, the optimal correlation value may be considered the highest correlation value in some cases. In cases where the correlation value (i.e. a cost value) is determined using a cost function, the optimal correlation value may be a minimum cost value.

At 240, the method 200 determines a mean correlation value and a standard deviation correlation value from all of the correlation values calculated for the first electrical set at 220. At 240, the method 220 determines whether the optimal correlation value differs from the mean correlation value by a predefined amount in order to determine whether the first electrical signal set has periodicity. The predefined amount may be referred to as a threshold correlation value or a periodicity cycle length confidence threshold.

In some cases, the predefined amount can be based on the standard deviation correlation value. In some cases, a user of the operator unit 12 can adjust the periodicity cycle length confidence threshold for determining whether an electrical signal set is periodic. For example, the user may adjust the confidence threshold so that an electrical signal set is determined to be periodic if the optimal correlation value differs from the mean correlation value by at least two standard deviations.

If the method 200 determines that the optimal correlation value differs from the mean correlation value by the predefined amount (e.g. a threshold correlation value), then at 245 the electrical signal set is identified as being periodic and the periodicity cycle length is recorded. If the method 200 determines that the highest correlation value is not greater than the mean correlation value by the predefined amount, then at 250 the electrical signal set is identified as not being periodic.

In some cases, method 200 can be implemented using periodic component analysis (PICA) as the iterative method 212. PiCA is an eigenvalue-based method for estimating periodicity in a periodic or near-periodic signal. Whether there are multiple periodic signals (e.g. recorded from multiple bipoles of a circular catheter over a periodic source) or repetitive salvos of a periodic signal (e.g. recorded from a single bipole), PICA seeks to combine the signals to maximize the periodic structure at a fundamental frequency, or periodicity cycle length.

PiCA can be used to evaluate the periodicity and potential cycle lengths of the bipolar EGMs in the first electrical signal set. For example, where the electrical signal set was obtained using a multi-electrode catheter, PiCA can be used to determine the correlation value for a plurality of potential cycle lengths for the electrical signal set. In this case, the correlation value for a potential cycle length may be the cost value of the PICA cost function for that potential cycle length. Thus, the optimal correlation value may correspond to the most optimal cost of the cost function (e.g. a local minimum of the cost function). In some cases, the correlation/cost value for a potential cycle length may be dependent on having matching morphologies between the peaks in the bipolar electrogram. That is, where the peaks in the bipolar electrogram for a potential cycle length have the same (or similar) morphologies, the correlation value may be expected to be better than for a potential cycle length where the morphologies of overlapping peaks do not match.

PiCA can be used to optimize a cost function for a range of periodicities (i.e. a range of potential cycle lengths) by combining the recorded signals in a weighted fashion with the weights chosen so that the periodic components of the signal constructively interfere (and are therefore enhanced) while the non-periodic components destructively interfere and are effectively canceled out. The potential cycle length corresponding to the most optimal cost function across all considered potential cycle lengths may be set as the cycle length of the first electrical signal set. Similar to the example embodiment of method 200 described above, in some cases the first electrical signal set may be considered periodic when the optimal correlation value (i.e. optimal/lowest cost value) differs from the mean optimal cost value by a predefined amount or threshold correlation value. For example, the threshold correlation value may be a predefined amount based on the standard deviation of the plurality of cost values. Determining that the first electrical signal set is periodic may occur when the cost value for the cycle length of that electrical signal set is at least two standard deviations below the mean cost value.

In some cases, the method 200 may provide an output such as a visual indication through display 16 to alert the user as to whether the electrical signal set is periodic. In some cases, the periodicity cycle length confidence threshold that was used may also be displayed to the user. A confidence level may also be displayed which reflects a ratio of the standard deviation of correlation values and the difference between the optimal correlation value and the mean correlation value. Example embodiments of a Graphical User Interface that may be displayed to a user will be discussed below with reference to FIGS. 19A-19C.

Referring again to FIG. 3, once an electrical signal set has been identified as having periodicity and the periodicity cycle length of the electrical signal set has been identified at 120, the method 100 proceeds to 130. In some cases, if method 100 determines that the electrical signal set is not periodic, then the method 100 may stop after 120 or the method 100 may obtain another electrical signal set at 110 for analysis. If the electrical signal set is not periodic, then the recording location corresponding to that electrical signal set may not be a focal source location, and would not be identified as a focal source location by method 100.

At 130, a plurality of peaks in the first electrical signal set are identified based on the identified periodicity cycle length. The plurality of peaks in the first electrical signal set may be identified using various suitable peak detection methods. For example, the method 100 may use a two stage procedure in which a first plurality of peaks are identified as being potential peaks and then a second plurality of peaks are identified from the potential peaks using a peak cost measure based on the identified periodicity cycle length. Analysis then continues using the second plurality of peaks which are identified as being peaks associated with the identified periodicity cycle length.

Figure 5:
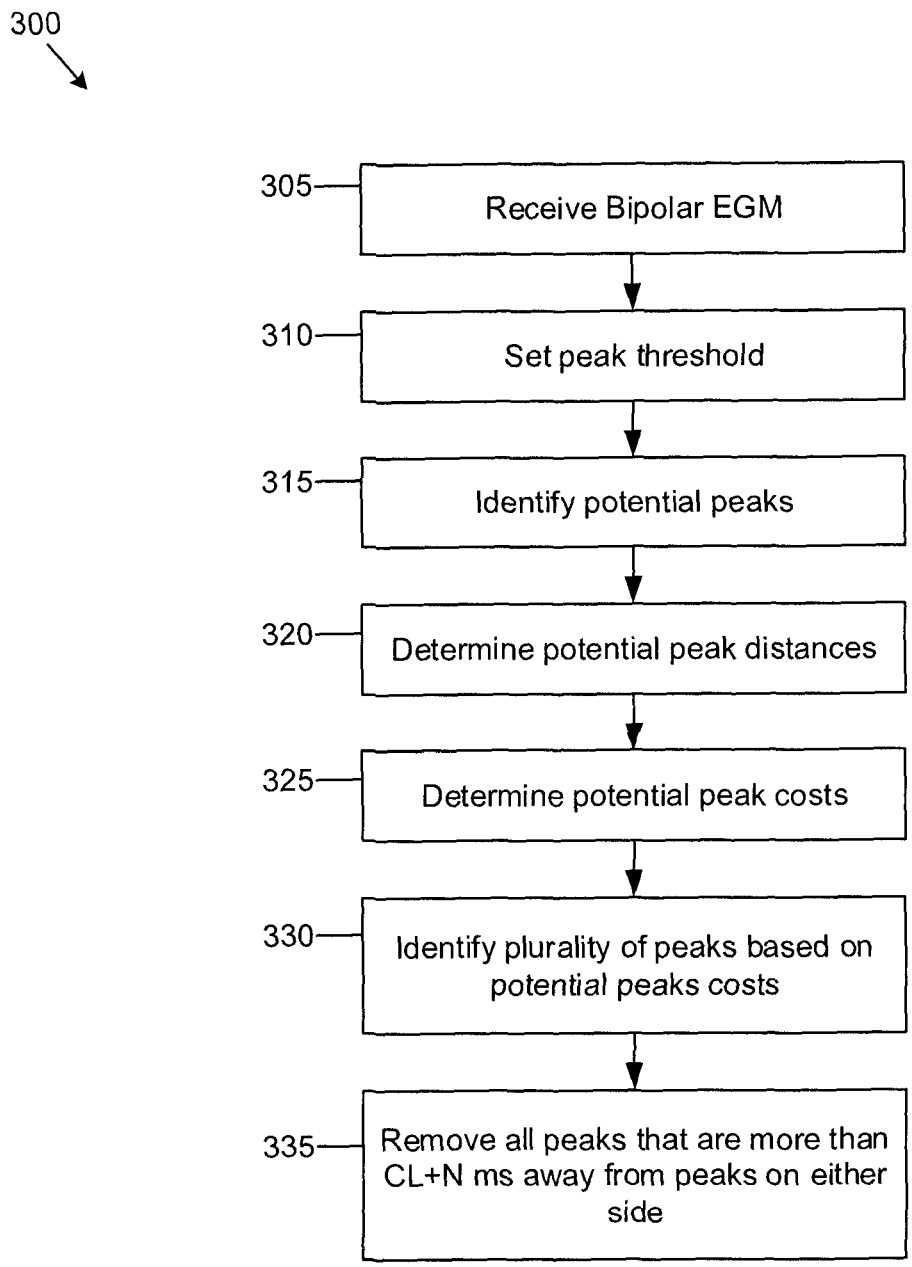
FIG. 5 is a flowchart of an example embodiment of a peak detection method that can be used by the focal source identification method of FIG. 3.

Referring now to FIG. 5, shown therein is a flowchart of an example embodiment of a peak detection method 300 that can be used by the focal source identification method 100. At 305, the method 300 obtains the bipolar EGM corresponding to the electrical signal set that is being analyzed.

At 310, a peak threshold is set or identified. The peak threshold may be an amplitude threshold. In some cases, the peak threshold may also include a gradient threshold. In some cases, the peak threshold can be set automatically while in other cases, the peak threshold can be adjusted by the user. In some cases, the peak threshold may be automatically set initially and can be subsequently adjusted by the user.

Once the peak threshold is set, at 315 the method 300 identifies a plurality of potential peaks. The plurality of potential peaks can be identified in the first electrical signal set by finding peaks in the first electrical signal set that satisfy the peak threshold. For example, the plurality of potential peaks may be identified as those peaks having an amplitude that is larger than the peak threshold where the peak threshold is an amplitude threshold.

At 320, the method 300 determines a plurality of potential peak distances. Each of the potential peak distances corresponds to a distance in the first electrical signal set between two of the potential peaks. In some cases, the potential peak distances may be calculated as a matrix or array of the absolute value of the differences between all of the potential peak locations with respect to one other in the first electrical signal set as shown in equation 1.

$$Peak_{Distances} = \text{Matrix of absolute value of} \quad (1)$$

difference of all peak locations w.r.t each other $$Peak_{Distances} = \begin{bmatrix} |P(1) - P(1)| & \cdots & |P(1) - P(N)| \\ \vdots & \ddots & \vdots \\ |P(N) - P(1)| & \cdots & |P(N) - P(N)| \end{bmatrix}$$

$P(N)$ – $N$th peak location in $Peak_{EGM}$

At 325, the method 300 determines a plurality of potential peak costs as is shown in equation 2. Each of the potential peak costs corresponds to one of the potential peak distances. In some cases, each of the potential peak costs may be determined based on a difference between the corresponding peak distance and the identified periodicity cycle length. This difference may represent a simple difference, log of differences or square of differences. The plurality of potential peak costs may be stored as a matrix or array of peak costs.

$$Peak_{Cost} = Peak_{Distances} - P \quad (2)$$

$$Peak_{Cost} = \begin{bmatrix} |Peak_{Distances}(1, 1) - P| & \cdots & |Peak_{Distances}(1, N) - P| \\ \vdots & \ddots & \vdots \\ |Peak_{Distances}(N, 1) - P| & \cdots & |Peak_{Distances}(N, N) - P| \end{bmatrix}$$

At 330, the method 300 identifies the plurality of peaks based on the potential peak costs. In some embodiments, prior to identifying the plurality of peaks, the method 300 may identify a plurality of subsets of potential peaks from the plurality of potential peaks.

For example, in some cases, one or more starting peaks and one or more ending peaks in the plurality of potential peaks may be identified. For example, these may be the first 5 peaks and the last 5 peaks in the electrical signal set satisfying the peak threshold. A shortest path algorithm may then be iteratively applied to the plurality of potential peaks to identify different peak paths (or peak subsets) from one of the starting peaks to one of the ending peaks to provide an initial identification of these subsets of peaks.

After identifying the plurality of subsets of potential peaks, the method 300 may then determine the peak cost measure for each subset of potential peaks. In some cases, the peak cost measure is determined based on a sum of the potential peak costs corresponding to the peaks in the subset of potential peaks. The plurality of peaks can be identified based on the subset of potential peaks having a lowest peak cost measure. In some cases, the plurality of subsets of potential peaks may be identified iteratively and a peak cost measure may be determined for each subset of potential peaks.

In some cases, the subset of potential peaks may be identified by applying a shortest path distance algorithm on the matrix of peak costs for the peaks having the lowest peak cost measure. For example, the shortest path distance algorithm may determine the shortest cost path between the first peak and last peak in the plurality of potential peaks, and determine the subset of the plurality of peaks corresponding to that path. Suitable shortest path distance algorithms include, but are not limited to, Djikstra's algorithm and the Bellman-Ford algorithm, for example.

At 335, the method 300 may remove each of the peaks in the subset of potential peaks that are not within a peak threshold distance of an adjacent peak to identify a pruned subset of peaks. The method 300 may then identify the plurality of peaks as the pruned subset of peaks.

In some embodiments, the peak threshold distance can be determined based on the identified periodicity cycle length. In the example embodiment shown in FIG. 5, the peak threshold distance has been set to the identified periodicity cycle length plus an additional tolerance amount N. Removing the peaks that are not within a peak threshold distance of an adjacent peak may be used to ensure that the identified plurality of peaks conform to the identified periodicity cycle length.

Referring again to FIG. 3, once the plurality of peaks have been identified at 130, the method 100 proceeds to determine if the location is a focal source at 140. In some cases, identifying a first location as a focal source can include determining that the electrical signal set obtained from the first location is periodic. The cycle length and the plurality of peaks in the first electrical signal associated with the cycle length can be identified using the various methods described in accordance with the teachings herein. The location corresponding to the electrical signal set can be identified as a focal source location by analyzing the periodicity cycle length and the associated plurality of peaks. An example of a focal source identification method will be described in further detail below with reference to FIG. 6.

In some cases, analyzing the plurality of peaks having a periodicity cycle length based on the identified periodicity in the first electrical signal set can include determining that the peaks are stable. In some cases, analyzing the plurality of peaks having a periodicity cycle length based on the identified periodicity in the first electrical signal set can also include analyzing a corresponding plurality of peak morphologies in the first electrical signal set.

While the focal source identification methods may be described herein with reference to a single electrical signal set, it should be noted that the methods can also be applied to a plurality of additional electrical signal sets with each of the additional electrical signal sets being obtained from different locations in an organ of a patient.

Figure 6:
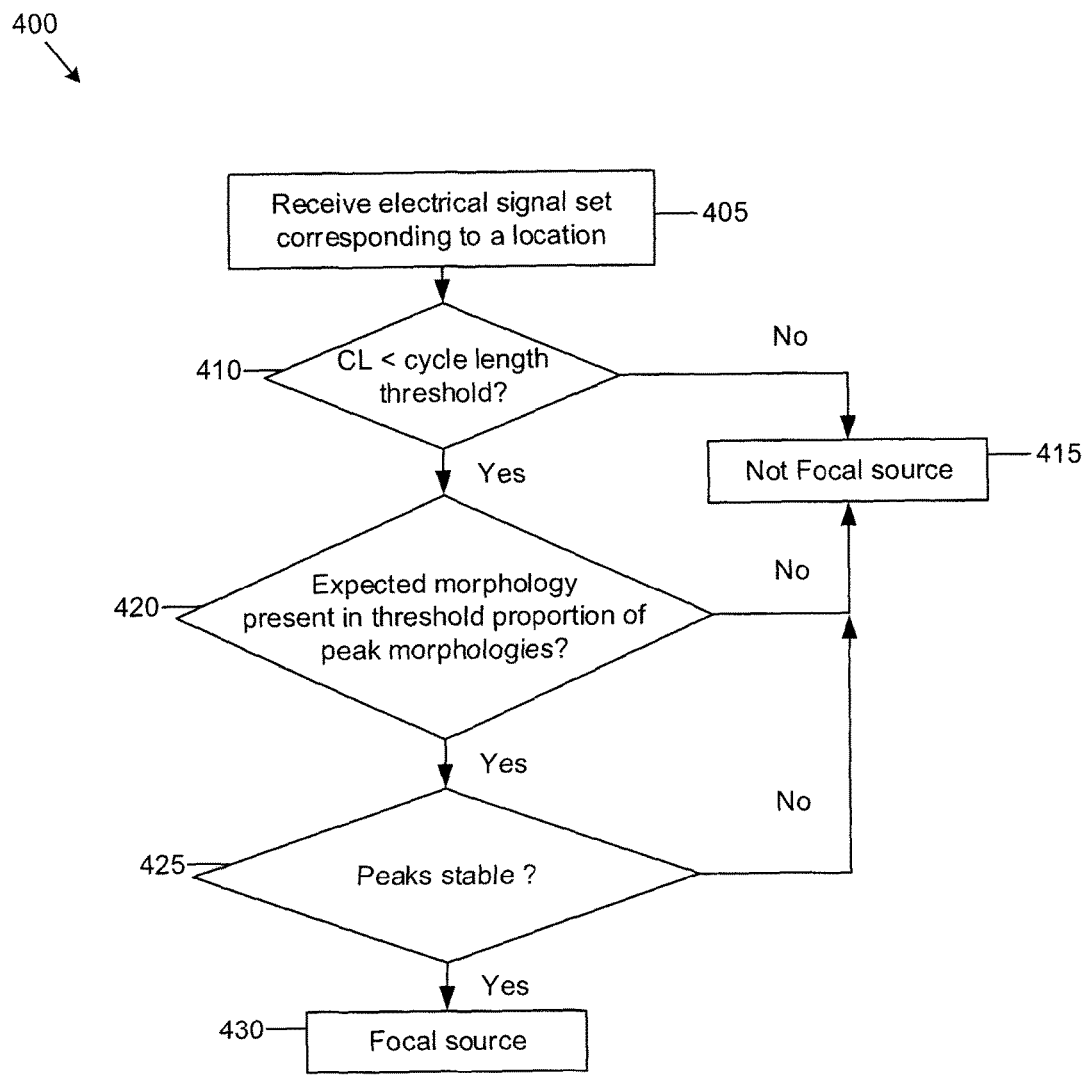
FIG. 6 is a flowchart of an example embodiment of a focal source verification method that can be used by the focal source identification method of FIG. 3.

Referring now to FIG. 6, shown therein is a flowchart of an example embodiment of a focal source verification method 400 that can be used by the focal source identification method 100. At 405, the method 400 obtains the first electrical signal set corresponding to the first location. The method 400 also receives the periodicity cycle length and the plurality of peaks that correspond to the periodicity cycle length in the first electrical signal set (which may be determined using methods 100, 200 and 300). Focal source verification method 400 is an example of a method that may be used to determine if the identified periodicity cycle length and the identified plurality of peaks have focal source characteristics. Examples of focal source characteristics will be described with reference to 410, 420, and 425 below.

At 410, the periodicity cycle length is analyzed by determining whether the identified periodicity cycle length is less than a periodicity cycle length threshold. In some cases, a focal source characteristic may be the identified periodicity cycle length being less than the periodicity cycle length threshold. If the identified periodicity cycle length is not less than the periodicity cycle length threshold, the first location is identified as not corresponding to a focal source at 415. In some cases, the operator unit 12 may display the results of the focal source identification method 100 on the display 16.

In some cases, the system 10 can receive and analyze a plurality of electrical signals sets corresponding to different locations in a patient's organ. A periodicity cycle length distribution based on the periodicity cycle lengths may be determined for each of the electrical signal sets. The periodicity cycle length threshold may be determined based on a property of the periodicity cycle length distribution that may be associated with a focal source. Alternatively, in some cases, the periodicity cycle length threshold can be set by the user of the operator unit 12 as a maximum periodicity cycle length that may correspond to a focal source location.

The periodicity cycle length threshold may be used so that only those locations with physiologically relevant, periodic activity are identified as focal source locations. As a result, in some cases the periodicity cycle length threshold can be identified as a percentile threshold of all the periodicity cycle lengths identified in the plurality of electrical signal sets received from the different locations in the patient. For example, in some cases the periodicity cycle length threshold may be set so that only locations with a cycle length in the bottom 10$^{th}$ percentile of the identified periodicity cycle lengths will be considered a focal source location.

If the periodicity cycle length is less than the periodicity cycle length threshold, a plurality of peak morphologies that are associated with these peaks may be analyzed at 420. In some cases, a focal source characteristic may be a percentage of peak morphologies in the first electrical signal set associated with the identified plurality of peaks having an expected morphology. The method 400 may first identify the plurality of peak morphologies in the first electrical signal set, with each peak morphology corresponding to one of the identified peaks. For example, a given peak may first be identified in the bipolar EGM. A unipolar EGM portion in the unipolar EGM corresponding to the given peak of the bipolar EGM can then be identified. The identified unipolar EGM portion can then be analyzed to identify the peak morphology of the given peak.

In some cases, the identified unipolar EGM portions corresponding to each of the identified peaks of the bipolar EGM can be analyzed manually. In those cases, the unipolar EGM portions may be displayed to the user, such as a clinician, on display 16, for example. The user can then analyze the morphology of the unipolar EGM portions. The morphology of the unipolar EGM portions can be analyzed to determine if they correspond to an expected morphology indicative of a focal source location. In these cases, the identification of a plurality of peaks based on an identified periodicity cycle length can be used to guide the user in which portions of the unipolar EGM to analyze.

Alternatively, in some embodiments, the identified unipolar EGM portions corresponding to each of the identified peaks may be analyzed automatically using suitable signal processing algorithms. For example, the method 400 may analyze the unipolar EGM portions and determine the morphology present based on comparison with predefined morphology templates using a form of similarity analysis. In these example embodiments, the method 400 may then automatically determine whether the morphology corresponds to an expected morphology indicative of a focal source location.

The plurality of peak morphologies may be analyzed to determine that at least a certain proportion of the analyzed peak morphologies have an expected morphology. In some embodiments, the expected morphology may be a QS morphology in the unipolar EGM. In some embodiments, the proportion may be such that the expected morphology is found for a majority of the identified unipolar electrogram portions. For example the proportion may be 90% in some embodiments. Thus, in some cases, in order for the first location to be identified as focal source location, the QS morphology may need to be detected in 90% of the unipolar EGM portions corresponding to the plurality of peaks identified in the bipolar EGM at the identified periodicity cycle length. In some embodiments, the presence of an RS morphology in more than a maximum tolerance number of the unipolar EGM portions may be used to indicate that the first location is not a focal source location.

If the expected morphology is present in a certain proportion of peak morphologies that are analyzed, then the plurality of peaks may be further analyzed at 425 to determine whether the first location is a focal source location. In some cases, a focal source characteristic may be that the identified plurality of peaks are stable. Analyzing the plurality of peaks may include determining that the identified plurality of peaks is stable. Determining that the identified plurality of peaks is stable can be done by determining if a number of consecutive peaks in the plurality of peaks are spaced apart by a certain time interval that is substantially equal to the periodicity cycle length and is relatively stable during the recorded EGM, and if the number of consecutive peaks is greater than a consecutive peak threshold. If the number of consecutive peaks is larger than the consecutive peak threshold, then the first location can be identified a focal source location. In some embodiments, the consecutive peak threshold may be adjusted by user to ensure a desired level of confidence in the identification of the focal source locations.

The analysis performed in 425 may be done automatically. In other embodiments, this analysis performed in 425 may be done manually by displaying the plurality of peaks to the user through the display 16.

Figure 7A:
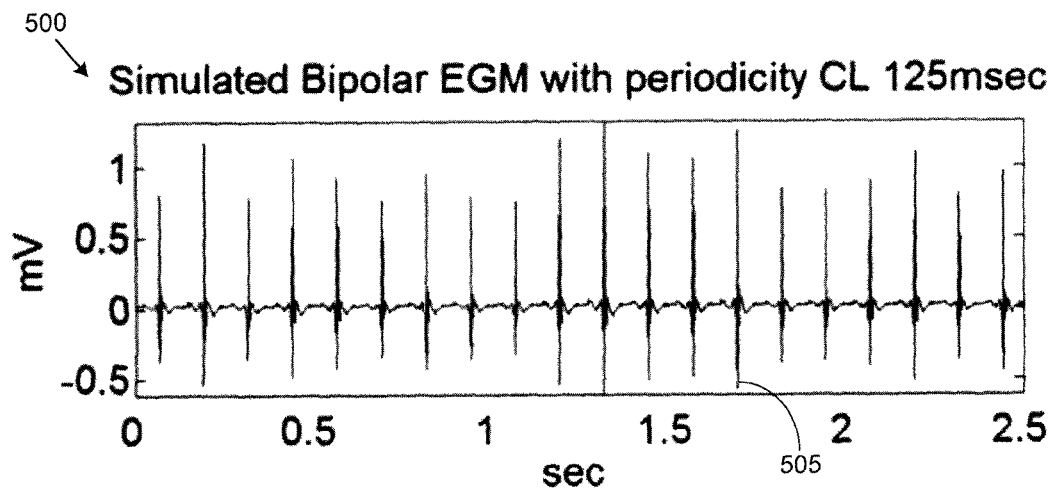
FIG. 7A is a diagram illustrating an example of a simulated bipolar electrogram having periodic activations.

Referring now to FIG. 7A, shown therein is a diagram illustrating an example of a simulated bipolar EGM 500. The bipolar EGM 500 includes a plurality of simulated periodic activation peaks 505. The bipolar EGM 500 has been simulated so that the periodic peaks 505 have a periodicity cycle length of 125 ms.

Figure 7B:
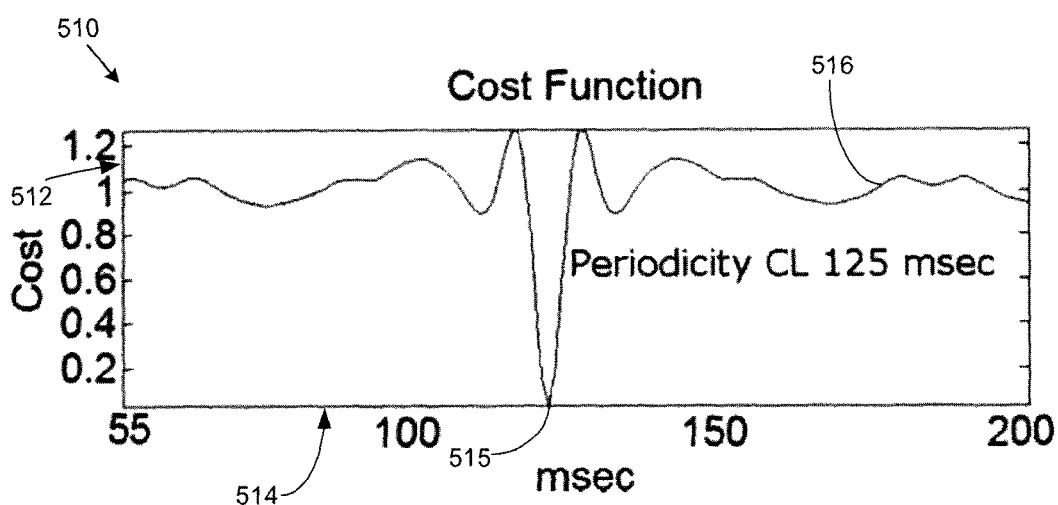
FIG. 7B is a diagram illustrating a periodicity cost function corresponding to the simulated bipolar electrogram of FIG. 7A.

Referring now to FIG. 7B, shown therein is a diagram illustrating a plot 510 of a cost function 516 corresponding to the simulated bipolar EGM 500. The cost function 516 illustrates the cost 512 associated with a range of potential cycle lengths 514 determined using the PiCA method discussed above. The cost function 516 has a local minimum 515 (i.e. an optimal cost or optimal correlation value) at a potential cycle length of 125 ms which corresponds to the known periodicity cycle length of the simulated bipolar EGM 500. The local minimum 515 differs from the mean by more than the threshold correlation value, so the simulated bipolar EGM 500 was determined to be periodic, as expected.

Figure 7C:
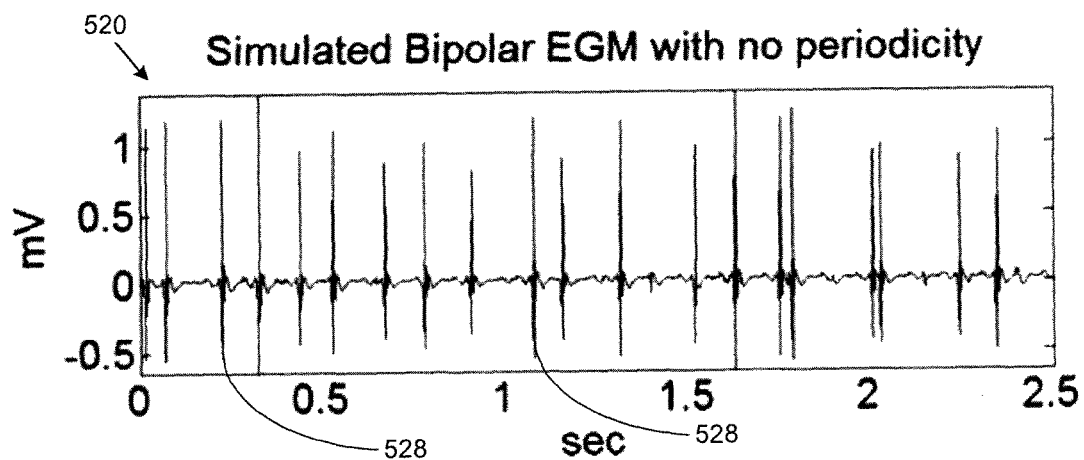
FIG. 7C is a diagram illustrating an example of a simulated bipolar electrogram without periodic activations.

Referring now to FIG. 7C, shown therein is a diagram illustrating an example of another simulated bipolar EGM 520. The bipolar EGM 520 has been simulated to be lacking in periodicity but to include a plurality of aperiodic activation peaks 528.

Figure 7D:
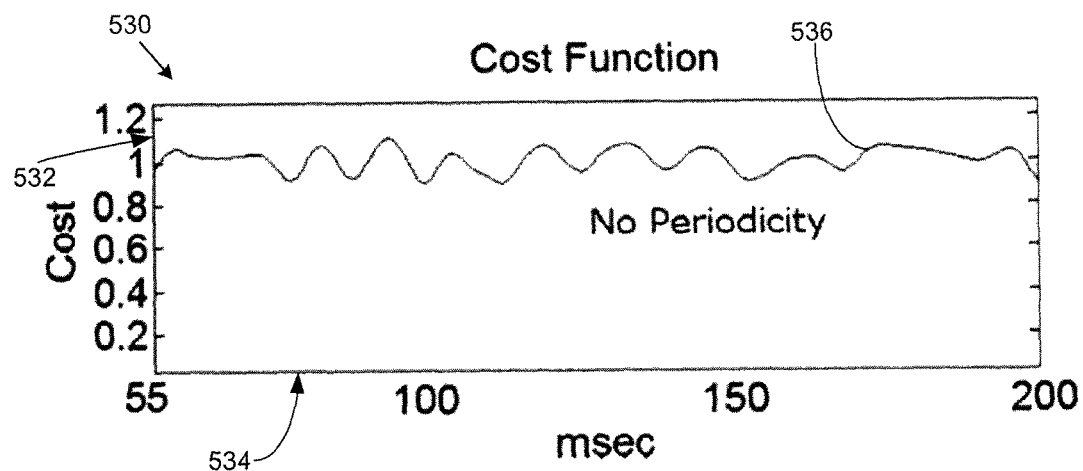
FIG. 7D is a diagram illustrating a periodicity cost function corresponding to the simulated bipolar electrogram of FIG. 7C.

Referring now to FIG. 7D, shown therein is a diagram illustrating a plot 530 of a cost function 536 corresponding to the simulated bipolar EGM 520. The cost function 536 illustrates the cost 532 associated with a range of potential cycle lengths 534 determined using the PICA method discussed above. The cost function 536 does not appear to show any local minimum—none of the potential cycle lengths 534 have an associated cost that differs from the mean cost by more than the predefined amount (the threshold correlation value), so no periodicity was detected.

Figure 7E:
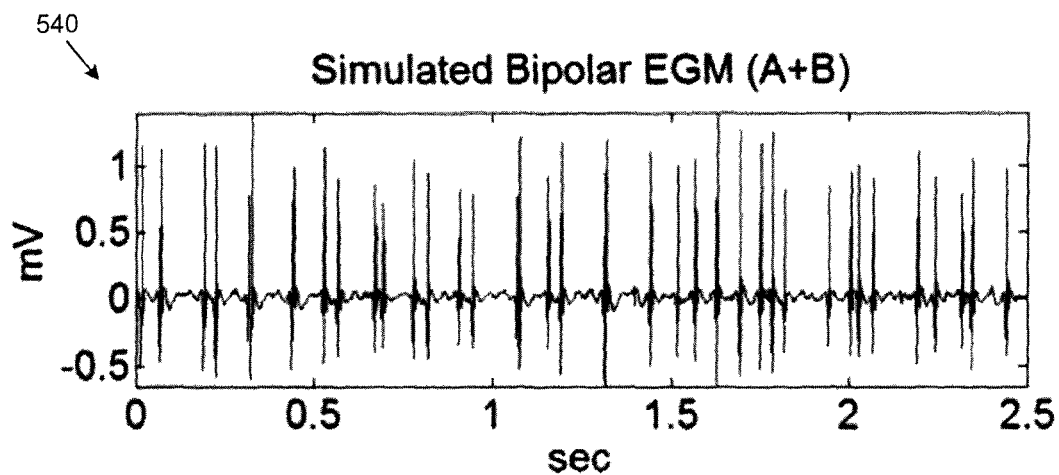
FIG. 7E is a diagram illustrating an example of a simulated bipolar electrogram combining the simulated bipolar electrograms from FIG. 7A and FIG. 7C.

Referring now to FIG. 7E, shown therein is a diagram illustrating an example of another simulated bipolar EGM 540. The bipolar electrogram 540 has been simulated to include both the periodic activation peaks 505 from FIG. 7A and the aperiodic activation peaks 528 of FIG. 7C. Due to the aperiodic peaks 528, the periodicity of the periodic peaks 505 are no longer visually apparent in bipolar EGM 540.

Figure 7F:
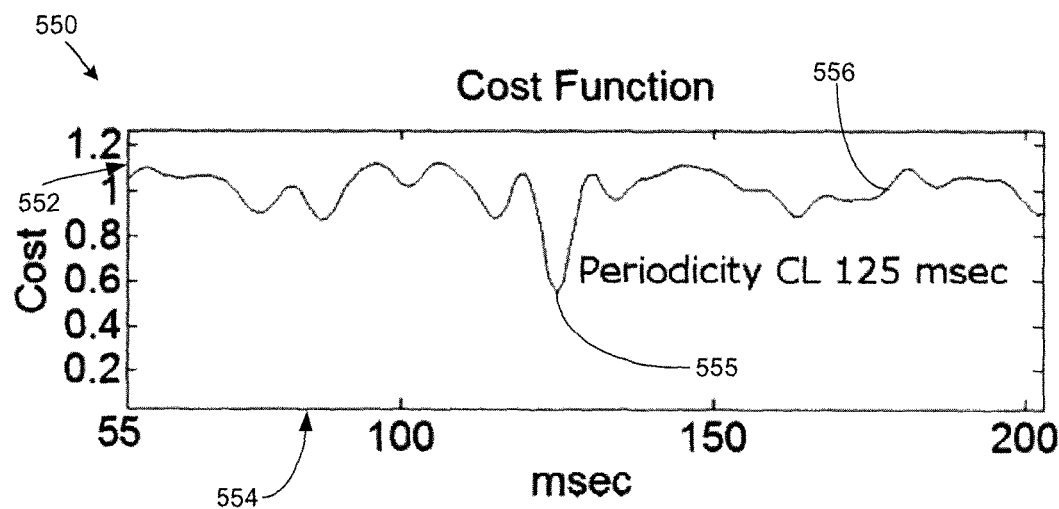
FIG. 7F is a diagram illustrating a periodicity cost function corresponding to the simulated bipolar electrogram of FIG. 7E.

Referring now to FIG. 7F, shown therein is a diagram illustrating a plot 550 of a cost function 556 corresponding to the simulated bipolar EGM 540. The cost function 556 illustrates the cost 552 associated with a range of potential cycle lengths 554 determined using the PiCA method for bipolar EGM 540. The cost function 556 shows a local minimum 555 at 125 ms which corresponds to the periodicity cycle length of the periodic activations 505. The PiCA method described above was able to accurately identify that bipolar EGM 540 was periodic and identified the correct periodicity cycle length, even in the presence of the aperiodic activations 528.

Referring now to FIGS. 8A and 8B, FIG. 8A shows a diagram illustrating a unipolar EGM 564, bipolar EGM 562 and ECG lead V1 560 received from a first recording site in the left atrium of a patient. The bipolar EGM 562 shows visually apparent periodic activation peaks. FIG. 8B shows a plot 570 of a cost function 576 corresponding to the bipolar EGM of FIG. 8A.

The cost function 576 has a local minimum 575 (i.e. optimal cost or optimal correlation value) at a 135 ms potential cycle length. The local minimum 575 is below the threshold level 578 for detecting periodicity. Accordingly the PICA methods described above indicate that the EGMs of FIG. 8A are periodic with a periodicity cycle length of 135 ms.

The peaks 566 are identified in the bipolar EGM 562 based on the periodicity cycle length of 135 ms using the methods described in accordance with the teachings herein. The corresponding peaks 568 in the unipolar EGM 564 are similarly identified. The peaks 568 in the unipolar EGM 564 have an RS morphology, indicating that the first recording site does not satisfy the focal source characteristics described above in method 400 and would not be identified as a focal source location.

Referring now to FIGS. 8C and 8D. FIG. 8C shows a diagram illustrating a unipolar EGM 584, a bipolar EGM 582 and an ECG lead V1 580 received from a second recording site in the left atrium of the patient. The bipolar EGM 582 shows visually apparent periodic activations. FIG. 8D shows a plot 590 of a cost function 596 corresponding to the bipolar EGM of FIG. 8C.

The cost function 596 has a local minimum 595 (i.e. optimal cost or optimal correlation value) at a 169 ms potential cycle length. The local minimum 595 is below the threshold level 598 for detecting periodicity. Accordingly the PiCA methods described above indicate that the EGMs of FIG. 8A are periodic with a periodicity cycle length of 169 ms.

The peaks 586 are identified in the bipolar EGM 582 based on the periodicity cycle length of 169 ms using the methods described in accordance with the teachings herein. The corresponding peaks 588 in the unipolar EGM 564 are similarly identified. The peaks 588 in the unipolar EGM 584 predominantly show a QS morphology, indicating that the second recording site may satisfy the focal source characteristics described above in method 400, if a sufficient percentage of the peaks 588 show the QS morphology.

Figure 8E:
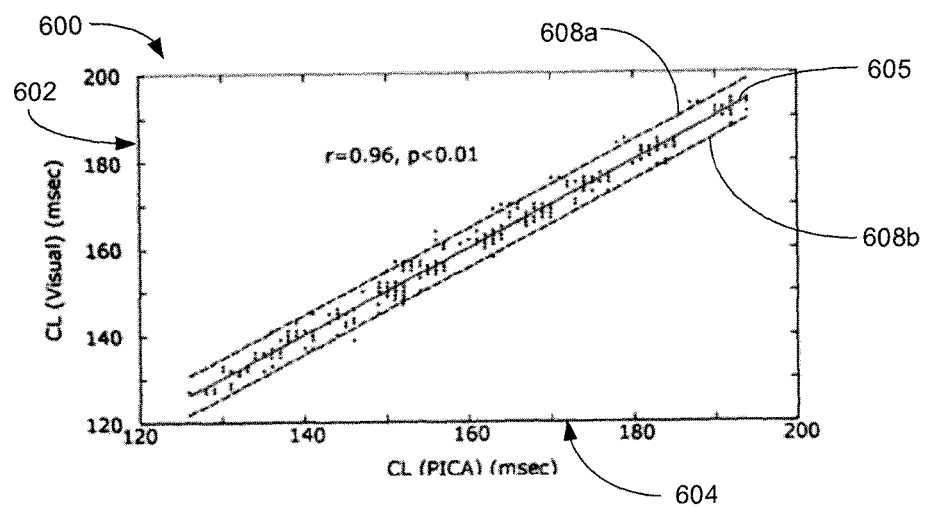
FIG. 8E is a diagram illustrating a plot of periodicity cycle lengths determined using methods described according to the teachings herein compared to visually-derived periodicity cycle lengths.

Referring now to FIG. 8E, shown therein is a plot 600 comparing the periodicity cycle lengths 604 derived using the PiCA-based methods described above with visually-derived cycle lengths 602 among a plurality of bipolar EGMs recorded from the left atrium of patients having visually apparent periodic activity. Plot 600 shows a strong linear correlation 605 between the PiCA derived periodicity cycle lengths 604 and the visually-derived periodicity cycle lengths 602 with a slope of 0.96. The plot 600 shows a significance level of <0.01 indicating that the correlation is statistically significant. The confidence lines 608a and 608b show the 95% confidence interval for the plot 600.

Figure 8F:
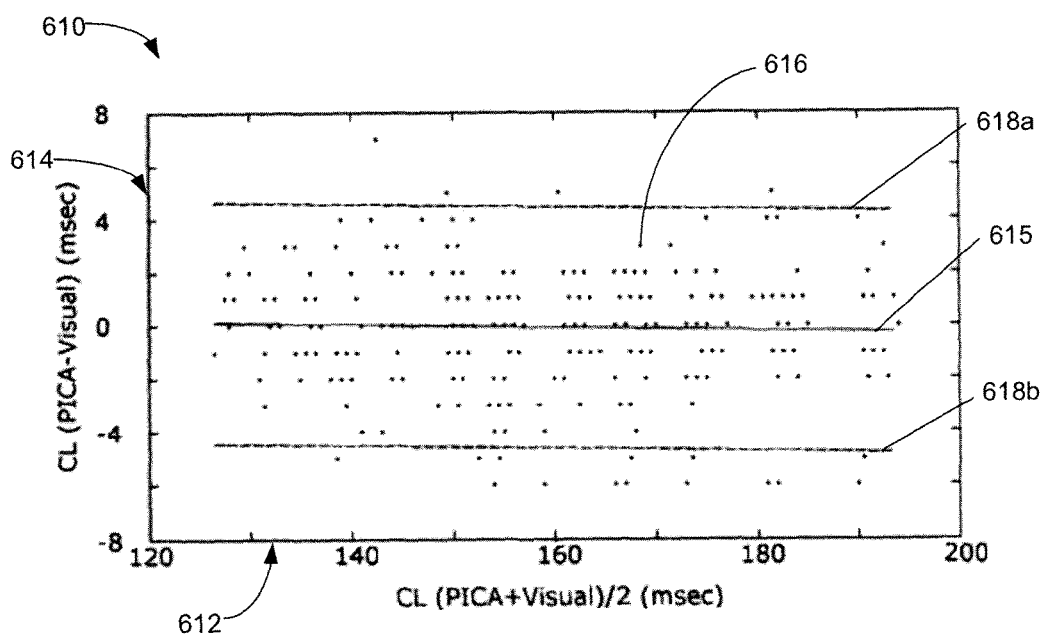
FIG. 8F is a diagram illustrating a Bland Altman plot of the differences between periodicity cycle lengths determined using methods described according to the teachings herein and visually-derived periodicity cycle lengths.

Referring now to FIG. 8F, shown therein is a Bland-Altman plot 610 illustrating the differences between the visually-derived periodicity cycle lengths 612 and the PICA derived periodicity cycle lengths 614 for the same bipolar EGMs as in FIG. 8E. The Bland-Altman plot 610 shows excellent agreement between the visually-derived periodicity cycle lengths 612 and the PiCA derived periodicity cycle lengths 614. The mean error 615 was 0.3±2.2 ms, and the majority of the periodicity cycle lengths are within the 95% confidence intervals 618a and 618b.

Figure 9A:
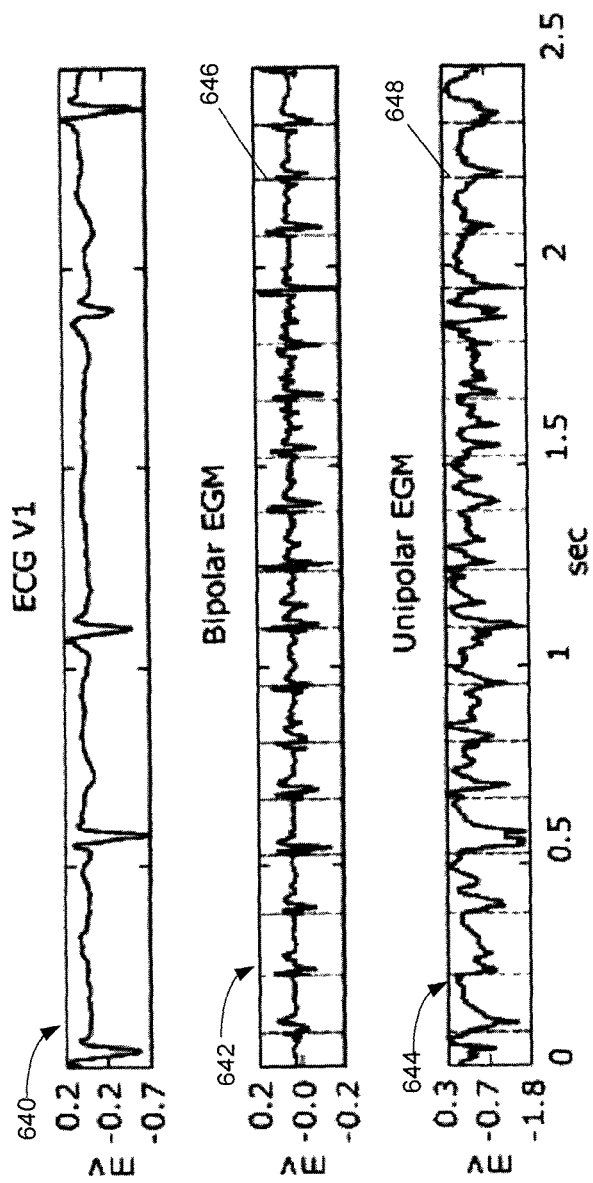
FIG. 9A is a diagram illustrating a unipolar electrogram, a bipolar electrogram and an ECG lead V1 received from a first recording site in the left atrium of a patient without visually apparent periodicity in the bipolar electrogram.
Figure 9B:
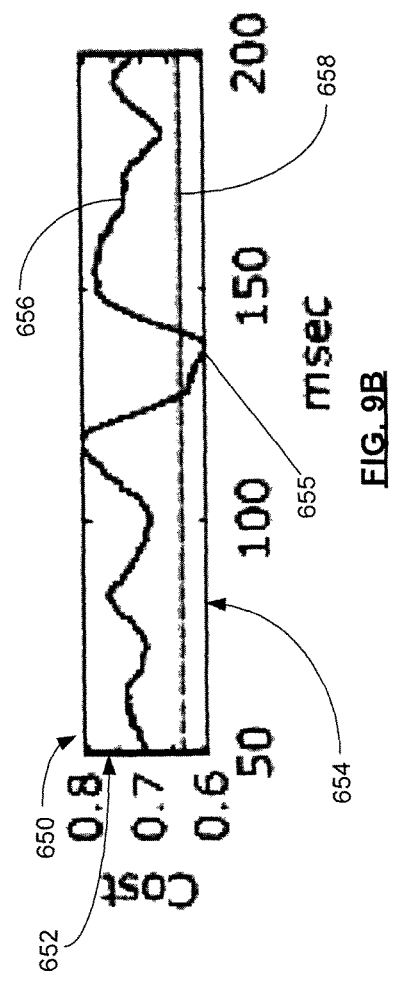
FIG. 9B is a diagram illustrating a periodicity cost function corresponding to the bipolar electrogram of FIG. 9A.

Referring now to FIGS. 9A and 9B, FIG. 9A shows a diagram illustrating a unipolar EGM 644, a bipolar EGM 642 and an ECG lead V1 640 received from a first recording site in the left atrium of a patient. The bipolar electrogram 642 has periodic activations that are not visually apparent. FIG. 9B shows a plot 650 of a cost function 656 corresponding to the bipolar EGM of FIG. 9A.

The cost function 656 has a local minimum 655 (i.e. optimal cost or optimal correlation value) that is below the threshold level 658 for detecting periodicity. Accordingly, the PiCA methods described above indicate that the bipolar EGM of FIG. 9A is periodic with a periodicity cycle length corresponding to the local minimum 655.

The peaks 646 are identified in the bipolar EGM 642 based on the periodicity cycle length corresponding to the local minimum 655 using the methods described in accordance with the teachings herein. The corresponding peaks 648 in the unipolar EGM 644 are similarly identified. The peaks 648 in the unipolar EGM 644 have a QS morphology, suggesting that the first recording site may be a focal source location if the recording site shows sufficient focal source characteristics.

Figure 9C:
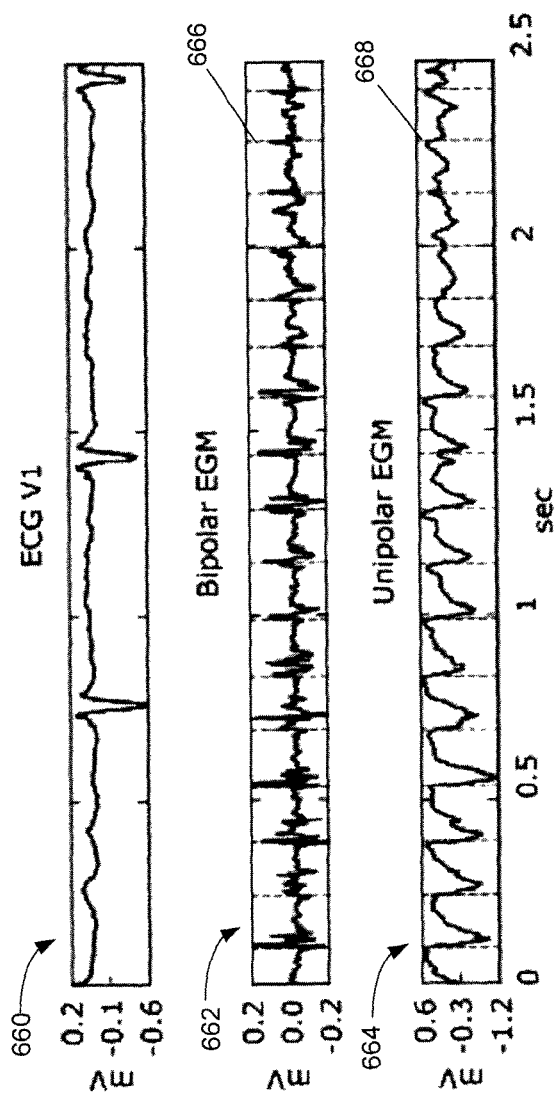
FIG. 9C is a diagram illustrating a unipolar electrogram, a bipolar electrogram and an ECG lead V1 received from a second recording site in the left atrium of a patient without visually apparent periodicity in the bipolar electrogram.
Figure 9D:
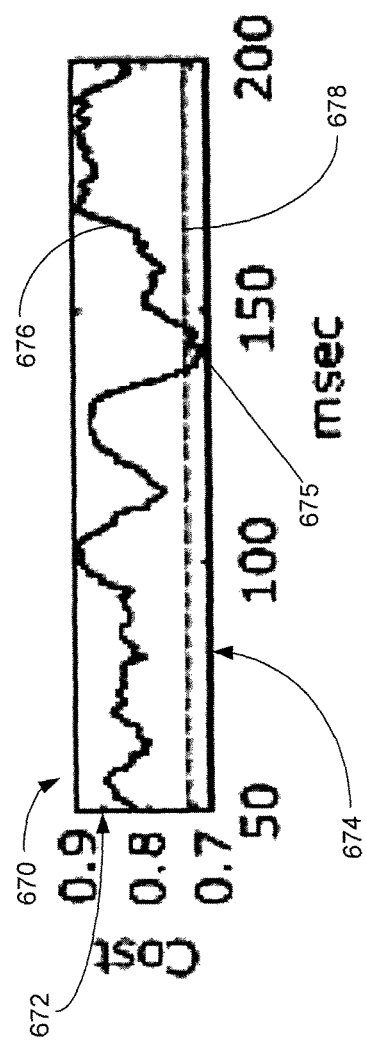
FIG. 9D is a diagram illustrating a periodicity cost function corresponding to the bipolar electrogram of FIG. 9C.

Referring now to FIGS. 9C and 9D, FIG. 9C shows a diagram illustrating a unipolar EGM 664, a bipolar EGM 662 and an ECG lead V1 660 received from a second recording site in the left atrium of a patient. The bipolar electrogram 662 again does not have visually apparent periodicity and shows greater fractionation than the bipolar EGM 642 shown in FIG. 9A. FIG. 9D shows a plot 670 of a cost function 676 corresponding to the bipolar EGMs of FIG. 9C.

The cost function 676 has a local minimum 675 (i.e. optimal cost or optimal correlation value) that is below the threshold level 678 for detecting periodicity. Accordingly the PiCA methods described above indicate that the EGMs of FIG. 9C are periodic with a periodicity cycle length corresponding to the local minimum 675.

The peaks 666 are identified in the bipolar EGM 662 based on the periodicity cycle length corresponding to the local minimum 675 using the methods described in accordance with the teachings herein. The corresponding peaks 668 in the unipolar EGM 664 are similarly identified. The peaks 668 in the unipolar EGM 664 have a QS morphology, suggesting that the second recording site may also be a focal source location.

Figure 9E:
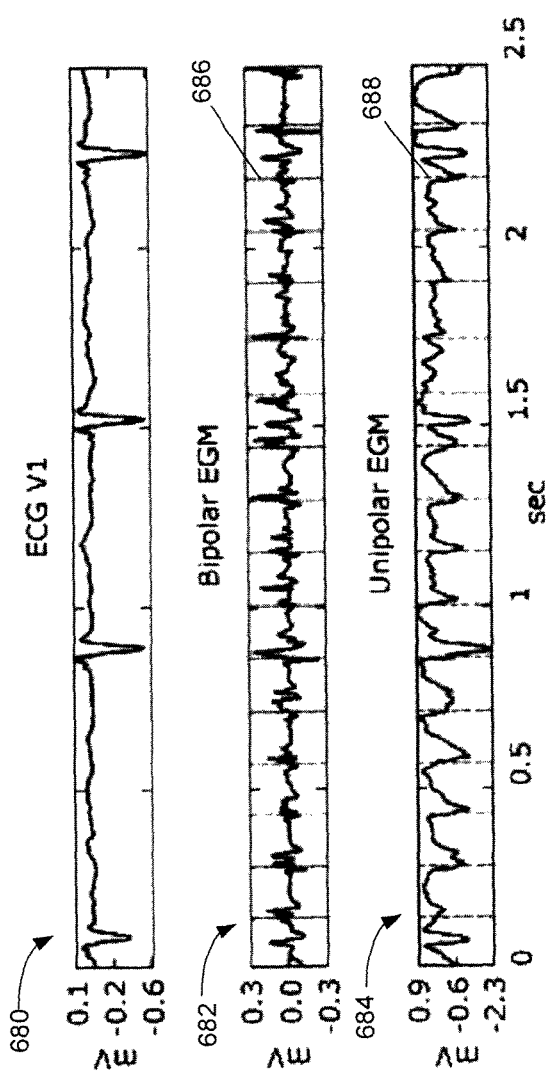
FIG. 9E is a diagram illustrating a unipolar electrogram, a bipolar electrogram and an ECG lead V1 received from a third recording site in the left atrium of a patient without visually apparent periodicity in the bipolar electrogram.
Figure 9F:
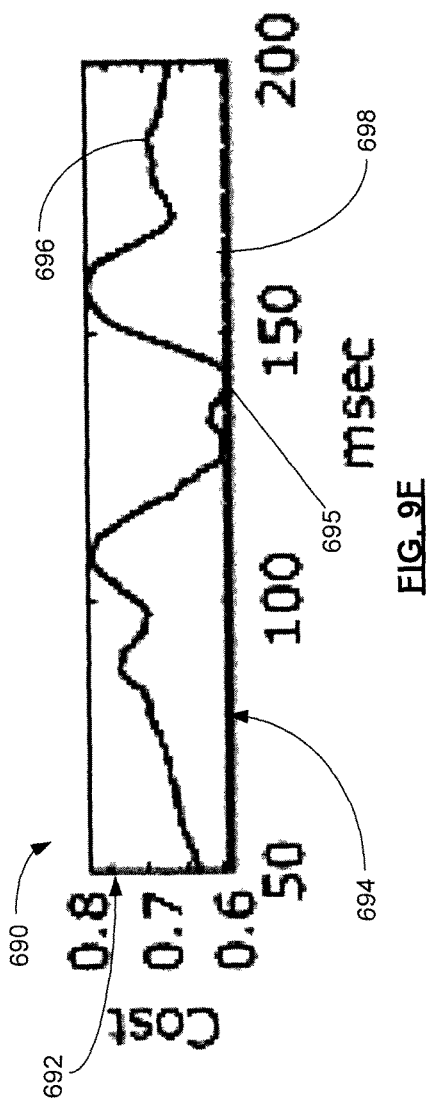
FIG. 9F is a diagram illustrating a periodicity cost function corresponding to the bipolar electrogram of FIG. 9E.

Referring now to FIGS. 9E and 9F, FIG. 9E shows a diagram illustrating a unipolar EGM 684, a bipolar EGM 682 and an ECG lead V1 680 received from a third recording site in the left atrium of a patient. Once again the bipolar EGM 682 does not have visually apparent periodicity and shows even greater fractionation than the bipolar EGM 662 shown in FIG. 9C. FIG. 9F shows a plot 690 of a cost function 696 corresponding to the bipolar EGM of FIG. 9E.

The cost function 696 has a local minimum 695 (i.e. optimal cost or optimal correlation value) that is below the threshold level 698 for detecting periodicity. Accordingly the PICA methods described above indicate that the EGMs of FIG. 9E are periodic with a periodicity cycle length corresponding to the local minimum 695.

The peaks 686 are identified in the bipolar EGM 682 based on the periodicity cycle length corresponding to the local minimum 695 using the methods described in accordance with the teachings herein. The corresponding peaks 688 in the unipolar EGM 684 are similarly identified. The peaks 688 in the unipolar EGM 684 have a QS morphology, suggesting that the third recording site may be another focal source location.

Figure 9G:
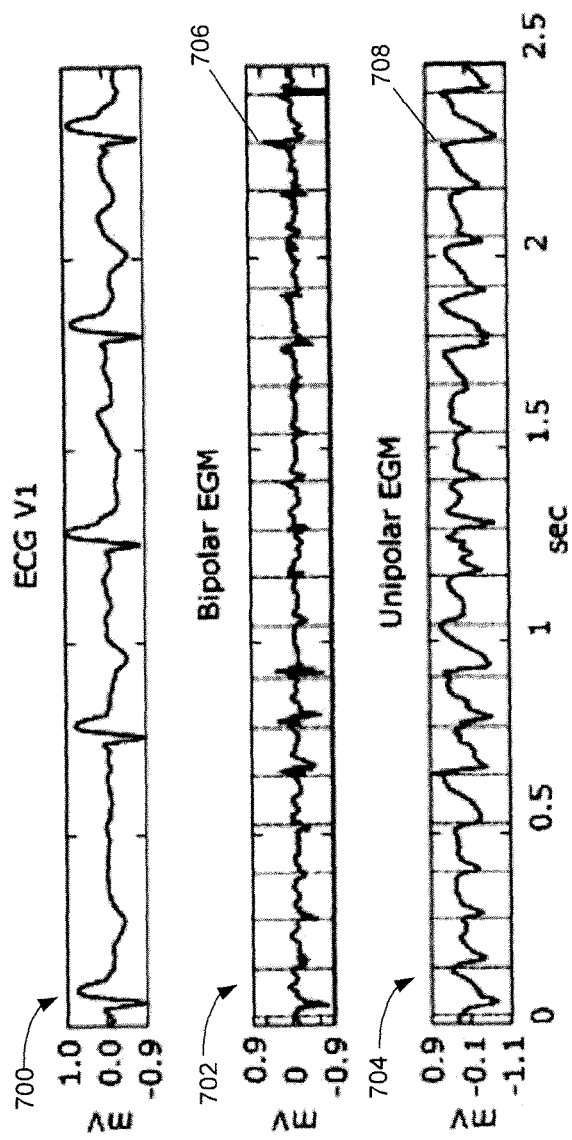
FIG. 9G is a diagram illustrating a unipolar electrogram, a bipolar electrogram and an ECG lead V1 received from a fourth recording site in the left atrium of a patient without visually apparent periodicity in the bipolar electrogram.
Figure 9H:
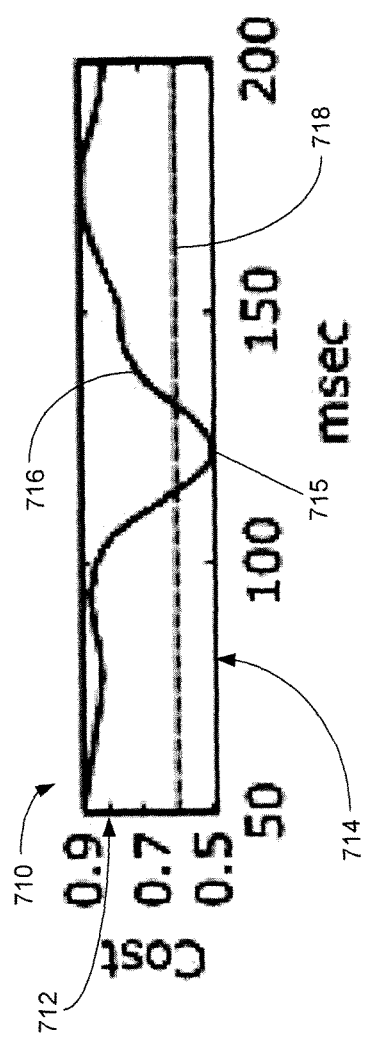
FIG. 9H is a diagram illustrating a periodicity cost function corresponding to the bipolar electrogram of FIG. 9G.

Referring now to FIGS. 9G and 9H, FIG. 9G shows a diagram illustrating a unipolar EGM 704, a bipolar EGM 702 and an ECG lead V1 700 received from a fourth recording site in the left atrium of a patient. The bipolar electrogram 702 does not have visually apparent periodicity and shows even greater fractionation than the bipolar EGM 682 shown in FIG. 9E. FIG. 9H shows a plot 710 of a cost function 716 corresponding to the bipolar EGMs of FIG. 9G.

The cost function 716 has a local minimum 715 (i.e. optimal cost or optimal correlation value) that is below the threshold level 718 for detecting periodicity. Accordingly the PiCA methods described above indicate that the EGMs of FIG. 9G are periodic with a periodicity cycle length corresponding to the local minimum 715.

The peaks 706 are identified in the bipolar EGM 702 based on the periodicity cycle length corresponding to the local minimum 715 using the methods described in accordance with the teachings herein. The corresponding peaks 708 in the unipolar EGM 704 are similarly identified. The peaks 708 in the unipolar EGM 704 also have a QS morphology, suggesting that the fourth recording site may be a further focal source location.

Figure 10A:
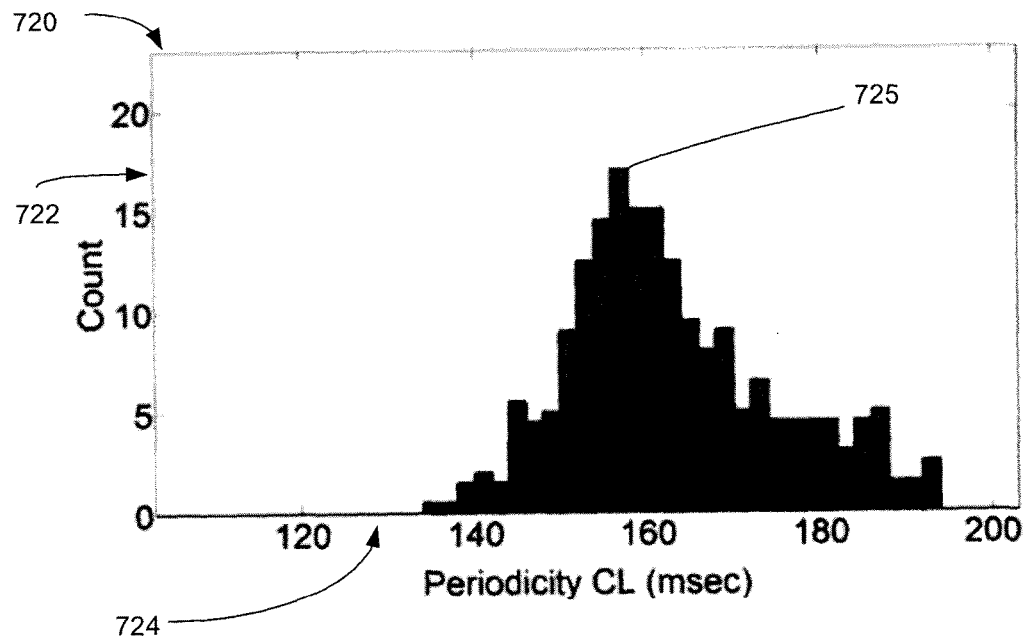
FIG. 10A is a diagram illustrating a histogram plot of the periodicity cycle lengths detected in the left atrium of a first patient.

Referring now to FIG. 10A, shown therein is a histogram plot 720 showing the count 722 of a range of periodicity cycle lengths 724 in the left atrium of a first patient with focal source locations in the pulmonary veins (PV). The histogram plot 720 identifies the dominant periodicity cycle length 725 as 159 ms.

Figure 10B:
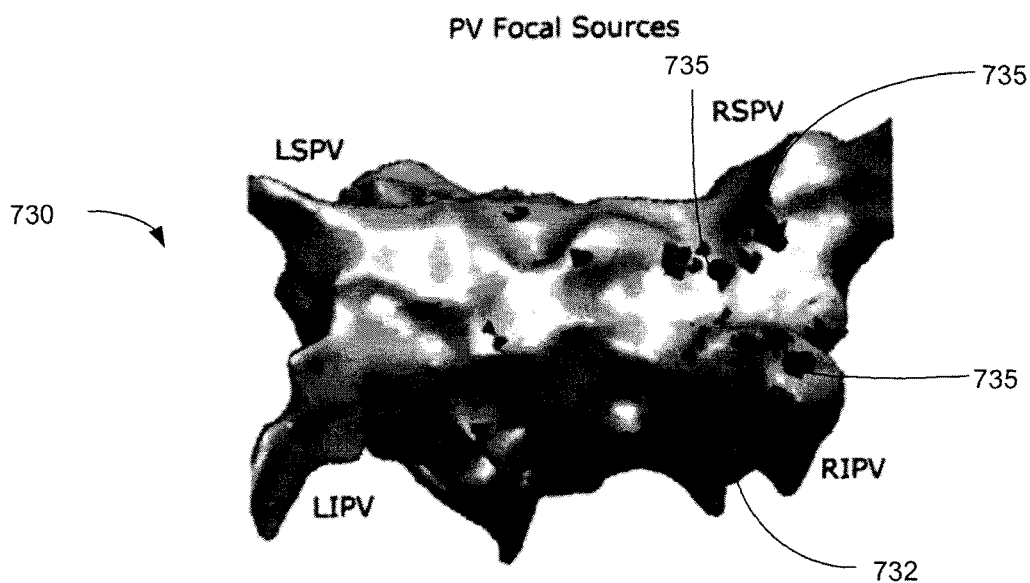
FIG. 10B is a diagram illustrating a 3D anatomical map of the left atrium of the first patient showing regions of periodic bipolar electrograms and focal source locations.

Referring now to FIG. 10B, shown therein is an anatomical map 730 of a posteroanterior view of the left atrium of the first patient. The anatomical map 730 indicates the left superior pulmonary vein (LSPV), left inferior pulmonary vein (LIPV), right superior pulmonary vein (RSPV), and right inferior pulmonary vein (RIPV) for the first patient. The anatomical map 730 shows regions of periodic bipolar EGMs such as region 732 and 3 focal source locations 735 have been identified in the right pulmonary vein ostium/antrum.

Figure 10C:
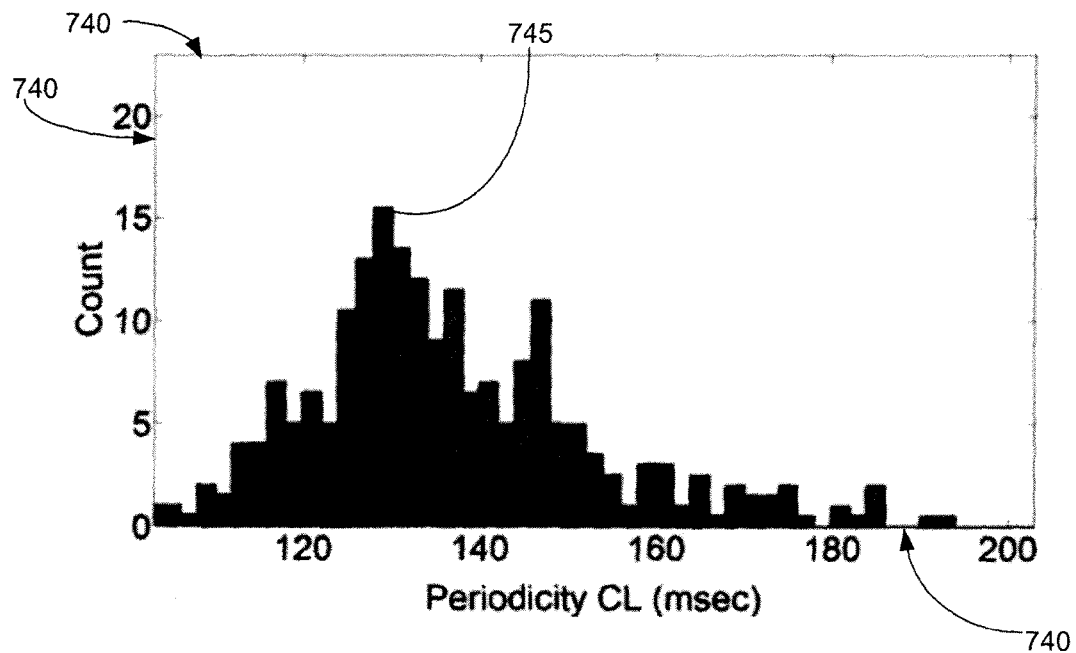
FIG. 10C is a diagram illustrating a histogram plot of the periodicity cycle lengths detected in the left atrium of a second patient.

Referring now to FIG. 10C, shown therein is a histogram plot 740 showing the count 742 of a range of periodicity cycle lengths 744 in the left atrium of a second patient with focal source locations outside the pulmonary vein ostium/antrum. The histogram plot 740 identifies a dominant periodicity cycle length 745 of 129 ms, much shorter than the dominant periodicity cycle length 725.

Figure 10D:
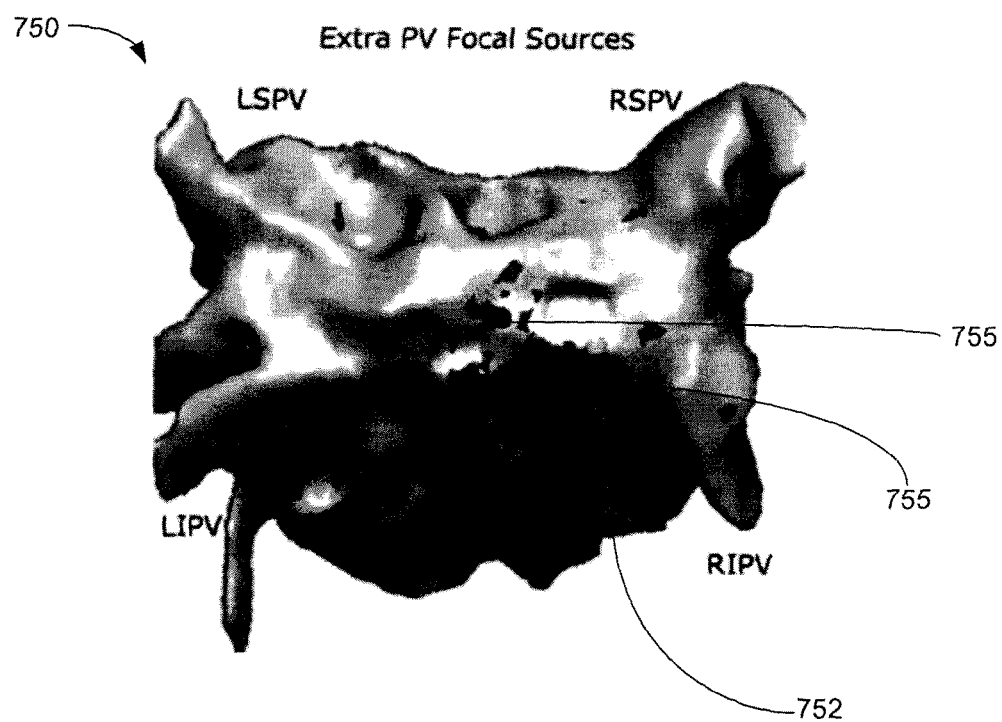
FIG. 10D is a diagram illustrating a 3D anatomical map of the left atrium of the second patient showing regions of periodic bipolar electrograms and focal source locations.

Referring now to FIG. 10D, shown therein is an anatomical map 750 of a posteroanterior view of the left atrium of the second patient. The anatomical map 750 shows regions of periodic bipolar EGMs such as region 752 and 2 focal source locations 755 in the posterior wall.

Figure 11A:
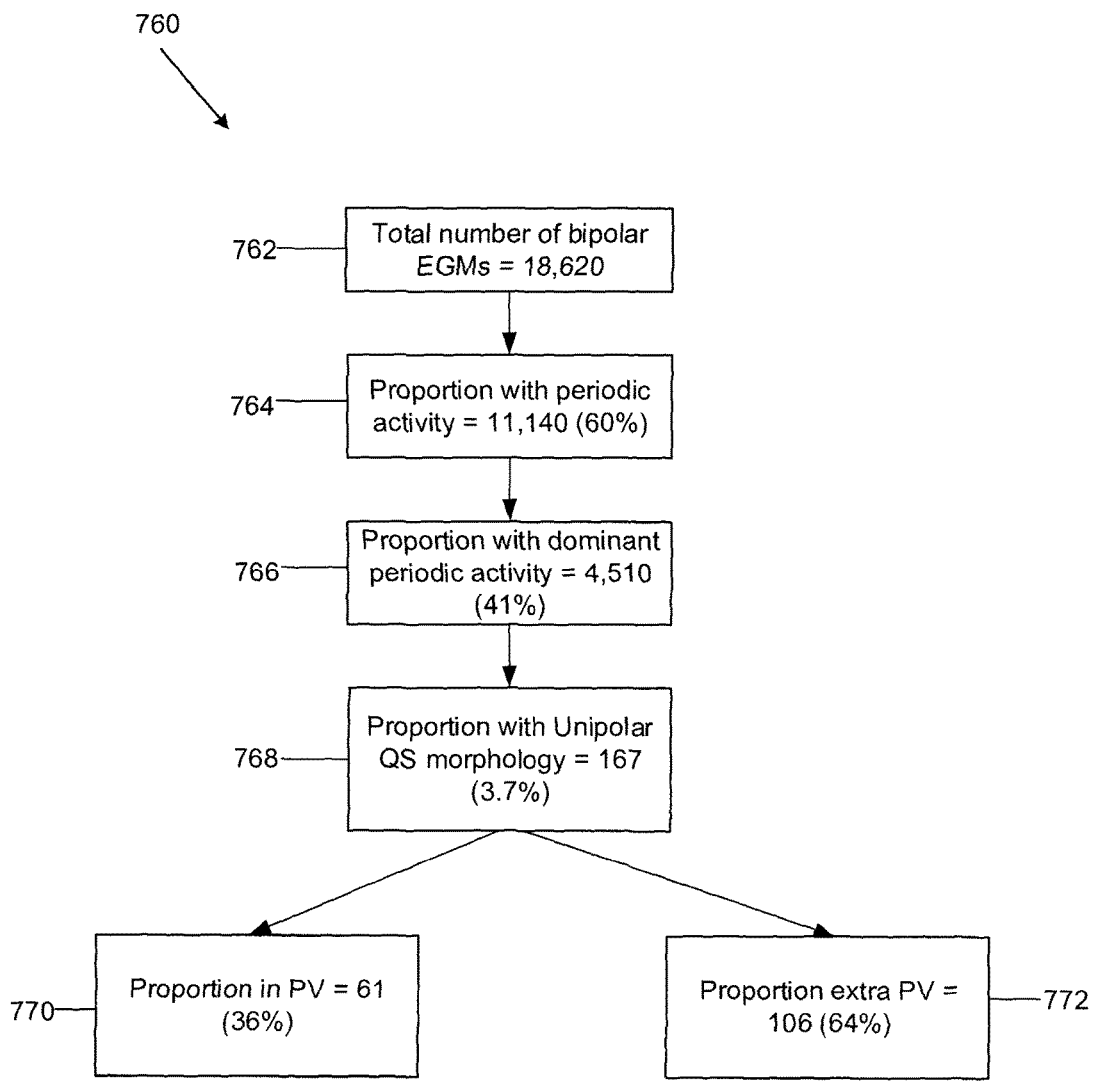
FIG. 11A is a diagram illustrating a flowchart of an example of the stepwise nature of the methods described in accordance with the teachings herein shown with reference to a total number of recorded EGMs.

Referring now to FIG. 11A, shown therein is a flowchart 760 illustrating the stepwise analysis performed by the methods described in accordance with the teachings herein. Flowchart 760 illustrates how the stepwise analysis performed by the methods described in accordance with the teachings herein gradually eliminates received electrical signal sets that no longer satisfy focal source characteristics. Flowchart 760 illustrates the prevalence of the electrical signal sets which may be used to indicate focal source location among all recorded EGMs at various levels of the analysis.

As flowchart 760 illustrates 18,620 bipolar EGMs were analyzed (762). The proportion 764 of those bipolar EGMs found to have periodic activity, for example at step 245 of method 200, was 11,140 or 60% of the total number of bipolar EGMs analyzed. The proportion 766 of periodic bipolar EGMs having dominant periodic activity was 4,510 or 41%.

The proportion 768 of bipolar EGMs having dominant periodic activity whose corresponding unipolar EGM showed a QS morphology at peak locations was 167, or 3.7% of the bipolar EGMs having dominant periodic activity. The proportion 768 corresponds to the electrical signal set for which a focal source location may be identified at 140 of method 100 when those electrical signal sets satisfy the criteria shown in method 400. Of those, the proportion 770 in the pulmonary veins was 61 (36%) while the proportion 772 outside the pulmonary veins was 106 (64%).

Figure 11B:
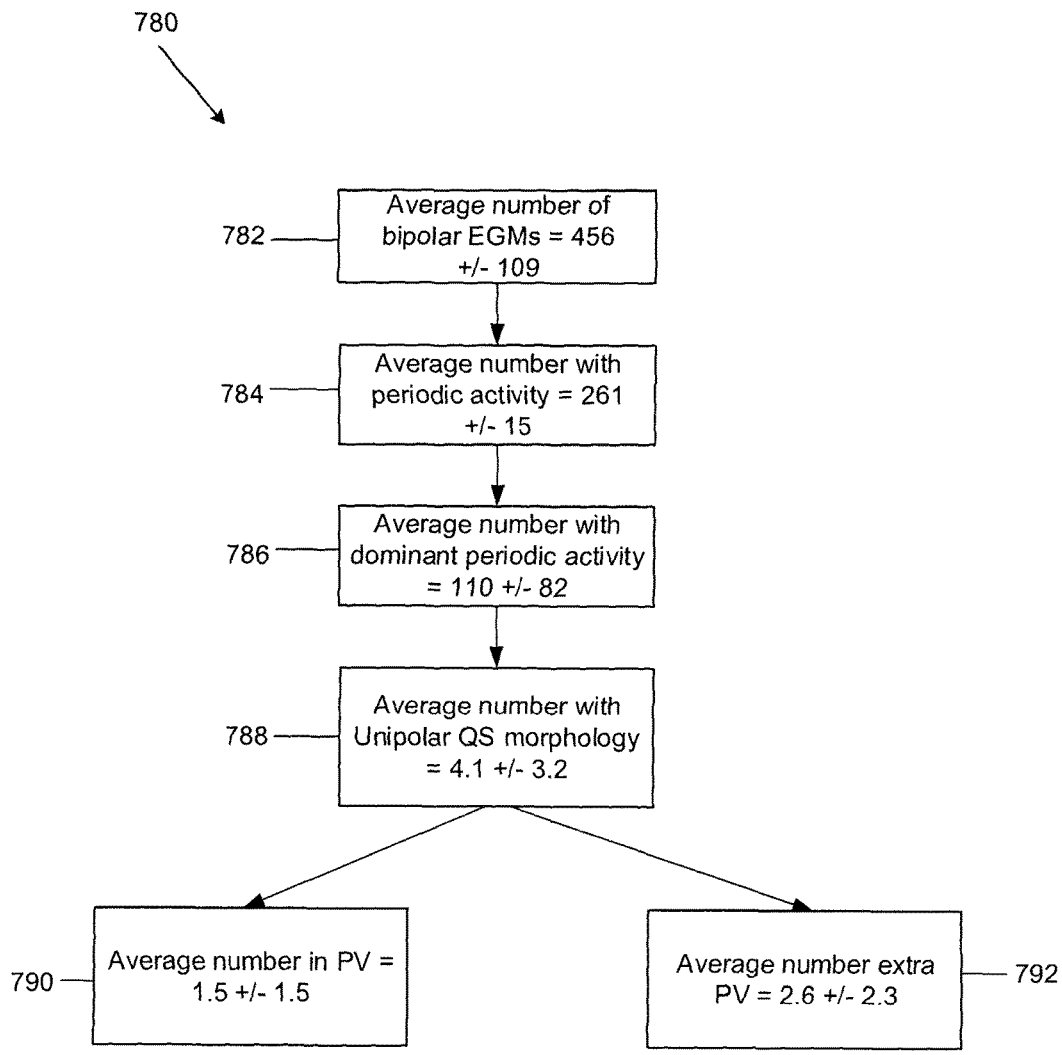
FIG. 11B is a diagram illustrating a flowchart of an example of the stepwise nature of the methods described in accordance with the teachings herein shown on a per-patient basis.

Referring now to FIG. 11B, shown therein is a flowchart 780 illustrating the stepwise analysis performed by the methods described in accordance with the teachings herein on a per patient basis. Flowchart 780 generally corresponds to flowchart 760, but shows a mean distribution per patient at each level of the analysis.

As flowchart 780 illustrates, an average of 456 (+/−109) bipolar EGMs were analyzed for each patient (782). The average number 784 of those bipolar EGMs found to have periodic activity for each patient, for example at step 245 of method 200, was 261+/−15. The average number 786 having dominant periodic activity was 110+/−82. The average number 788 of bipolar EGMs having dominant periodic activity whose corresponding unipolar EGM showed a QS morphology at peak locations was 4.1+/−3.2 per patient. This corresponds to the average number of focal source locations that may have been identified for each patient, for example at 140 in method 100. The average number 790 of focal source locations identified in the pulmonary veins was 1.5+/−1.5 while the average number 792 identified outside the pulmonary veins was 2.6+/−2.3.

Figure 12A:
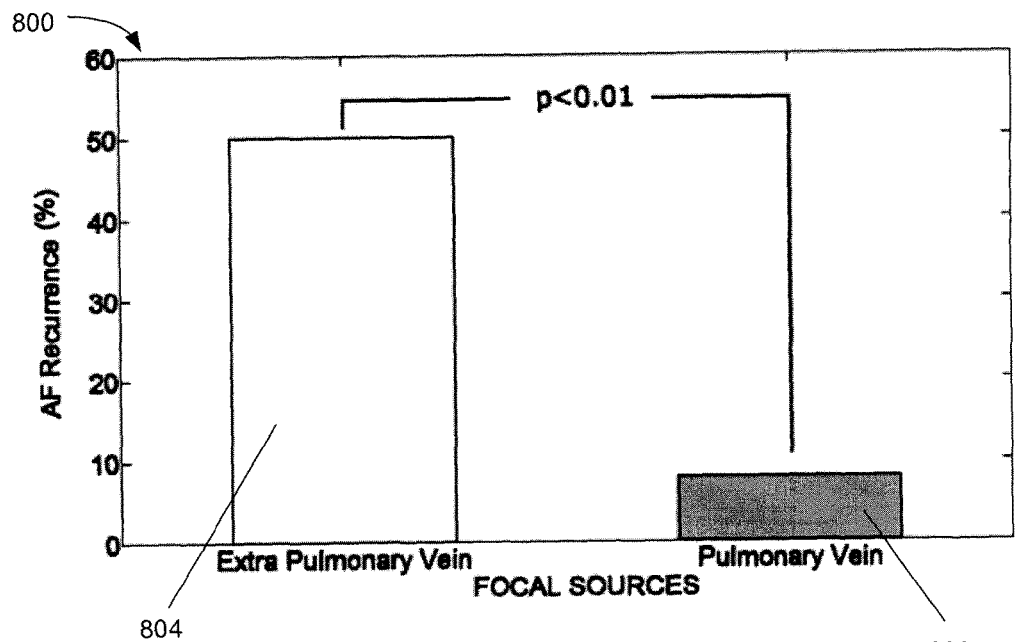
FIG. 12A is a diagram illustrating a plot of the AF recurrence in patients having focal source locations in the pulmonary veins only compared to the AF recurrence in patients with focal source locations outside the pulmonary veins.

Referring now to FIG. 12A, shown therein is a plot 800 illustrating the percentage of patients having AF recurrence where focal source locations were identified in the PV antra 802 and where focal source locations were identified outside the PV antra 804. The clinical outcomes shown in plot 800 were analyzed following PV antral ablation. As can be seen in plot 800, AF recurrence was significantly less among patients with only PV antral focal source locations compared to those with additional/exclusive extra PV antral focal source locations.

Figure 12B:
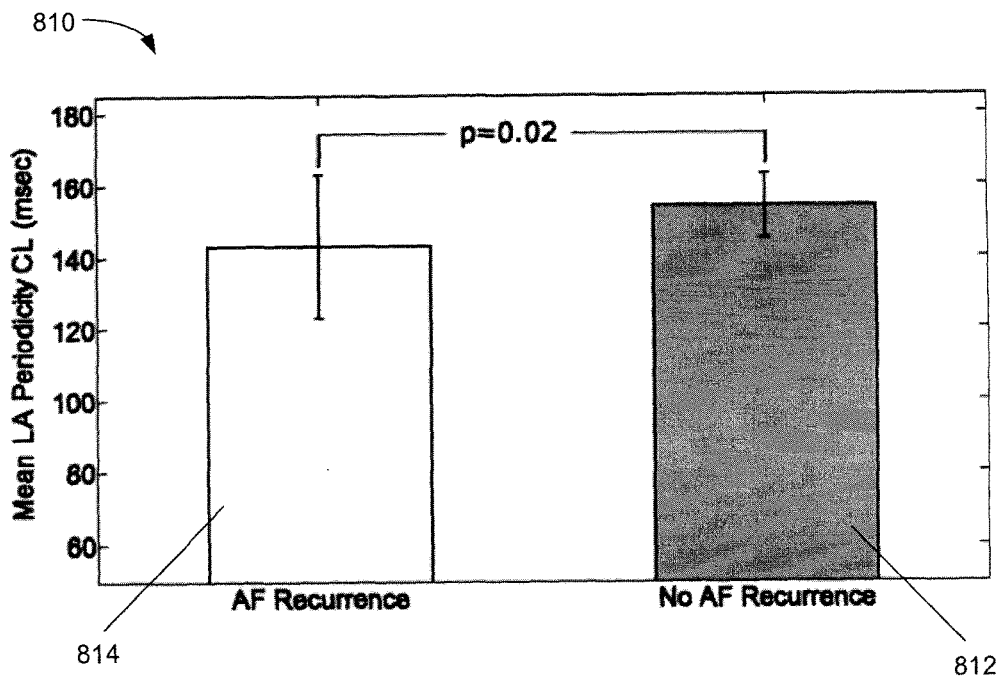
FIG. 12B is a diagram illustrating a plot of the mean periodicity cycle length in the left atrium of patients having AF recurrence compared to the mean periodicity cycle length in the left atrium of patients having no AF recurrence.

Referring now to FIG. 12B, shown therein is a plot 810 illustrating the mean periodicity cycle length identified in the left atrium of patients having AF recurrence 814 and patient having no AF recurrence 812. Among patients without AF recurrence, the mean LA periodicity cycle length 812 was significantly greater than the mean LA periodicity cycle length 814 for patients with AF recurrence.

In a study of 41 patients, bipolar EGMs were recorded in the left atrium during AF with a roving 20-pole circular catheter. Circumferential PV antral ablation with successful PV isolation was performed in all 41 patients. Ablation time was 58+/−17 minutes and during ablation 5 (12%) patients converted to sinus rhythm, while another 2 (5%) organized to atrial tachycardia/flutter. After a follow-up of 14+/−9 months, 15 (37%) of patients had had symptomatic AF recurrences and their characteristics are presented in Table 1. Among those with FS exclusively in the PV antra (n=12, 29%), only 1 (8%) had AF recurrence in follow-up. In the remaining 14 patients with extra-PV antral FS, AF recurrence was significantly greater (50%, p=0.03) as shown in FIG. 12A above. Patients with no FS (n=15, 36%) also had greater AF recurrence (50%, p=0.04) compared to those with PV antral FS.

Patients experiencing AF recurrence had evidence of more structural and electrical remodeling compared to those remaining in sinus rhythm based on larger LA diameter (45±6 vs. 42±4 mm, p<0.05) and shorter mean LA periodicity CL (143±20 vs. 154±9 ms, p<0.05) as shown in Table 1 and FIG. 12B. However, the mean LA dominant periodicity CL did not differ between patients with and without AF recurrence (166±18 vs. 160±16 ms, p=NS), and the area of periodicity (as a proportion of LA area) was not significantly different (15±11 vs. 19±8%, p=not significant).

TABLE 1

Patient characteristics and AF recurrence post-ablation

| | AF Recurrence (n = 15) | No AF Recurrence (n = 26) | p value |
|---|---|---|---|
| Age, yrs | 57 ± 10 | 57 ± 10 | 0.99 |
| Type of AF | | | |
| Paroxysmal AF, n (%) | 3 (30) | 7 (70) | |
| Persistent AF, n (%) | 12 (39) | 19 (61) | |
| AF symptom duration, yrs | 6.4 ± 4.5 | 5.1 ± 3.8 | 0.36 |
| Hypertension, n (%) | 4 (27) | 11 (42) | 0.50 |
| Diabetes, n (%) | 1 (7) | 2 (11) | 1.00 |
| Thyroid dysfunction, n (%) | 2 (13) | 3 (13) | 1.00 |
| Obstructive sleep apnea, n (%) | 5 (37) | 8 (44) | 0.62 |
| BMI (kg/m$^2$) | 29 ± 6 | 28 ± 7 | 0.93 |
| FS Characteristics | | | |
| Number of FS per patient | 1.5 ± 1.7 | 1.2 ± 1.1 | 0.48 |
| Patients with only PV antral FS, n (%) | 1 (7) | 11 (42) | |
| Patients with extra PV antral FS, n (%) | 7 (47) | 7 (27) | 0.03 * |
| Patients without any FS, n (%) | 7 (47) | 8 (31) | 0.04 * |
| FS periodicity CL | 163 ± 15 | 162 ± 17 | 0.84 |
| Structural and Electrical Characteristics | | | |
| LV ejection fraction, % | 58 ± 8 | 58 ± 8 | 0.63 |
| LA size, mm | 45 ± 6 | 42 ± 4 | 0.04 |
| LA volume, ml | 69 ± 58 | 57 ± 50 | 0.51 |
| Mean LA periodicity CL (ms) | 143 ± 20 | 154 ± 9 | 0.02 |
| Mean LA dominant periodicity CL (ms) | 166 ± 18 | 160 ± 16 | 0.35 |
| Mean periodicity area (% of LA surface) | 15 ± 11 | 19 ± 8 | 0.18 |
| Ablation time (min) | 57 ± 20 | 61 ± 23 | 0.42 |

* Versus patients with only PV antral FS.

Using contemporary ablation targets to modify atrial substrate in persistent AF has not resulted in durable rhythm control. Improving the specificity of substrate ablation by targeting AF drivers, such as FS, may improve long-term sinus rhythm maintenance. In the patients that were analyzed (whose characteristics are shown in Table 1), the presence of FS only in the PV antra predicted lower AF recurrence after PV antral ablation. Those with extra PV antral FS that were not ablated had more AF recurrence, suggesting that FS outside the PV antra may be important in AF maintenance and also require ablation.

Figure 13A:
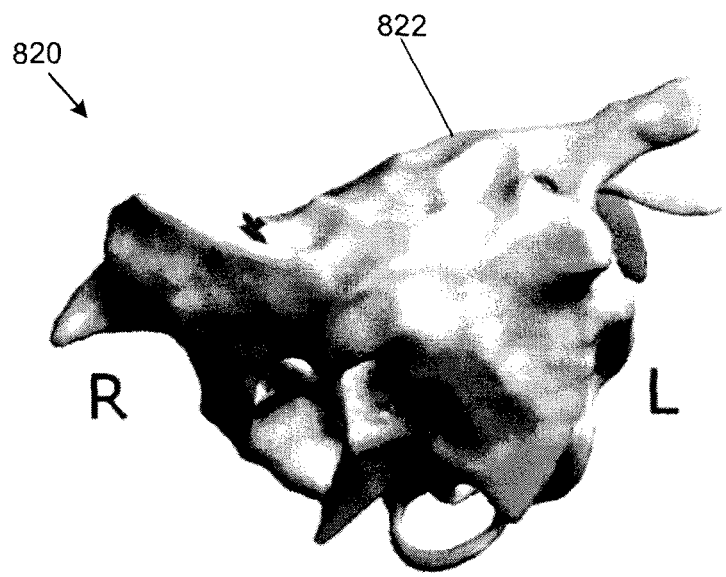
FIG. 13A is a diagram illustrating an example of a 3D map of a left atrium with the periodic regions highlighted along with their periodicity cycle lengths.

Referring now to FIG. 13A, shown therein is a diagram illustrating an example of a 3D map 820 of a left atrium in a first patient with the periodic regions highlighted. The 3D map 820 is an example of a 3D map of a left atrium 822 that may be displayed to the user of the system 10 after regions of periodicity have been identified in the atrium 822 using the focal source identification methods described in accordance with the teachings herein. In this patient, few periodic regions were identified in the left atrium 822. The cycle length of the periodic regions is indicated by the gray scale and the corresponding legend 829 (shown in FIG. 13B).

Figure 13B:
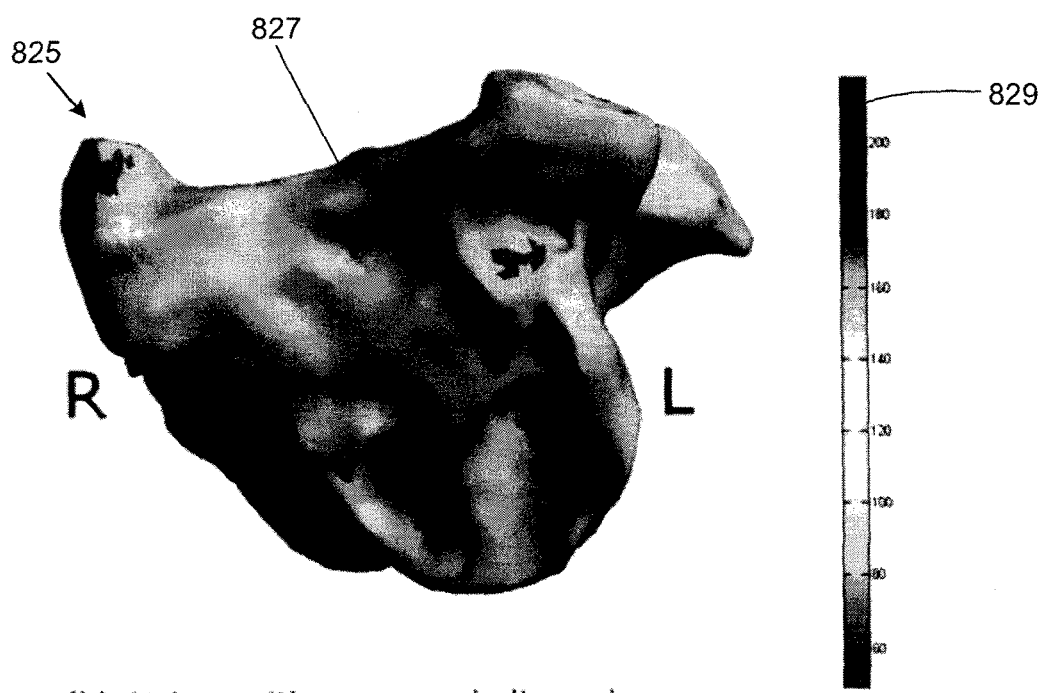
FIG. 13B is a diagram illustrating another example of a 3D map of a left atrium with the periodic regions highlighted along with their periodicity cycle lengths.

Referring now to FIG. 13B, shown therein is a diagram illustrating another example of a 3D map 825 of a left atrium in a second patient with the periodic regions highlighted. The 3D map 825 may be displayed to the user of the system 10 after regions of periodicity have been identified in the atrium 827 using the focal source identification methods described in accordance with the teachings herein. In this patient, many periodic regions were identified in the left atrium 827 shown in 3D map 825. The cycle length of the periodic regions is indicated by the gray scale and the corresponding legend 829.

Referring now to FIGS. 14A-14D shown therein are 3D maps of the left atrium 835 from a third patient. Each of the 3D maps shown in FIGS. 14A-14D show the same posterior view of the left atrium 835 in the same patient.

FIG. 14A shows a bipolar 3D map 830 of the left atrium 835 with the voltage of the corresponding bipolar EGMs highlighted. The 3D bipolar voltage map 830 demonstrated no significant scar burden in the left atrium 835.

FIGS. 14B-14D demonstrate the poor spatial correlation between periodicity (FIG. 14B), complex fractionated atrial electrocardiograms (CFAE) (Fractionation index (FI)>7) (FIG. 14C), and dominant frequency (DF) (>8 Hz) (FIG. 14D). Thus, the periodicity that has been determined according to the teachings herein is presenting an evaluation of signal organization which is not duplicated by the other conventional metrics.

Figure 15A:
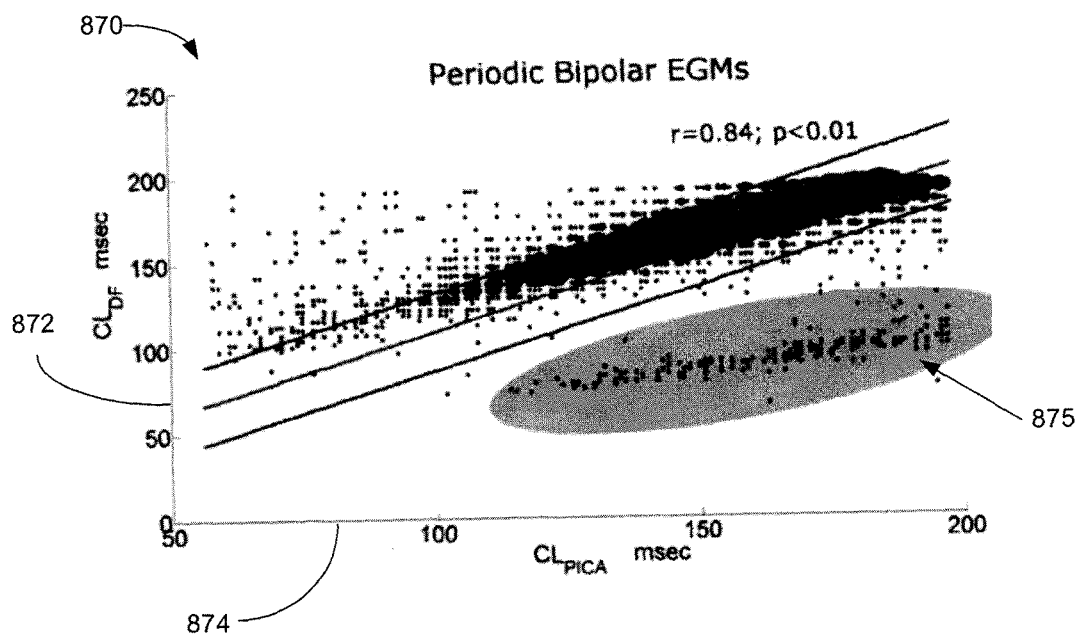
FIG. 15A is a diagram illustrating a plot of the correlation between periodicity cycle lengths identified using the methods described according to the teachings herein and the cycle lengths identified using dominant frequency analysis.

Referring now to FIG. 15A, shown therein is a plot 870 showing the correlation between periodicity cycle lengths 874 identified for a plurality of bipolar EGMs recorded from the left atrium of patients using PiCA with the methods described in accordance with the teachings herein and periodicity cycle lengths 872 identified for the same bipolar EGMs using dominant frequency (DF) analysis. For the majority of the bipolar EGMs shown in plot 870, there is a strong linear correlation (r=0.84, p<0.01) between the periodicity cycle lengths derived by the PiCA methods 874 and the dominant frequency analysis derived cycle lengths 872.

Despite the generally strong correlation in plot 870, there is a cluster 875 of bipolar EGMs that show poor correlation between the PiCA-derived periodicity cycle lengths 874 and the DF-derived cycle lengths 872. In cluster 875, the PiCA-derived periodicity cycle lengths 874 are about half the length of the DF-derived cycle lengths 872.

Figure 15B:
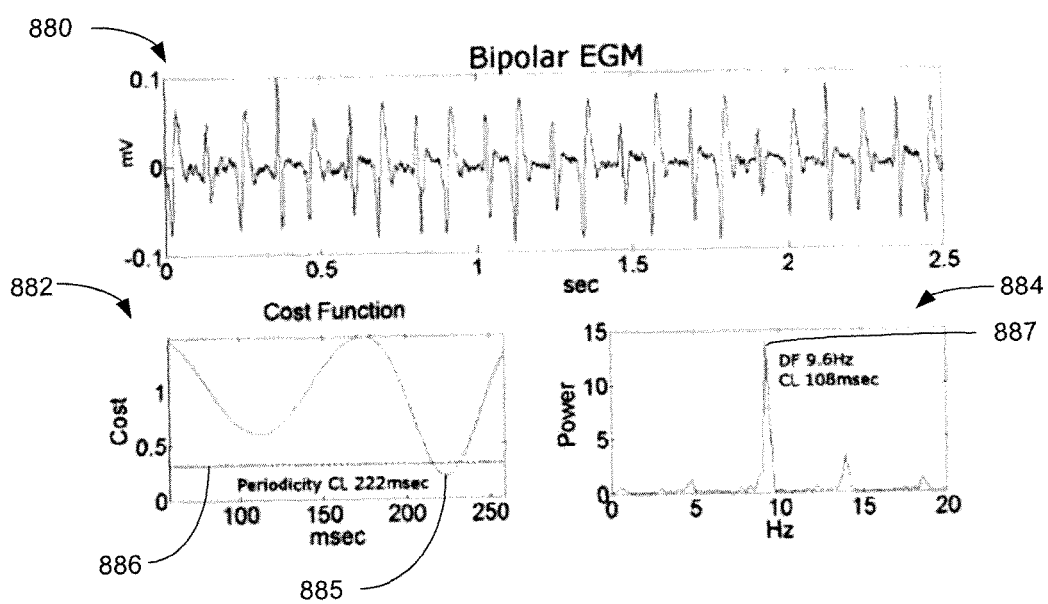
FIG. 15B is a diagram illustrating a bipolar electrogram recorded from the left atrium of a patient, a periodicity cost function corresponding to the bipolar electrogram, and a plot illustrating the dominant frequency analysis of the bipolar electrogram.

Referring now to FIG. 15B, shown therein is an example of a bipolar EGM 880 from the cluster 875 shown in FIG. 15A. The bipolar EGM 880 shows two sets of activations (potential peaks) with alternating morphologies. The two sets of activations in the bipolar EGM 880 are not double potentials because there is a prolonged isoelectric segment between them. Rather, the two sets of activations in the bipolar EGM 880 represent two different periodic activation peaks. Using the methods described in accordance with the teachings herein, the periodicity cycle length is determined to be 222 ms. Cost function 882 corresponding to bipolar EGM 880 shows a local minimum 885 at 222 ms, below the predefined threshold 886. In contrast, the DF analysis shown in plot 884 overestimates the frequency and identifies the dominant frequency 887 as 9.6 Hz (i.e. a cycle length of 108 ms). The methods described in accordance with the teachings herein can evaluate periodicity cycle length using correlation analysis that requires bipolar EGM morphology matching, so the second set of activations are not double counted. In contrast, DF analysis counts each of these activation peaks without considering EGM morphology, which reduces the true periodicity cycle length 2-fold.

Figure 15C:
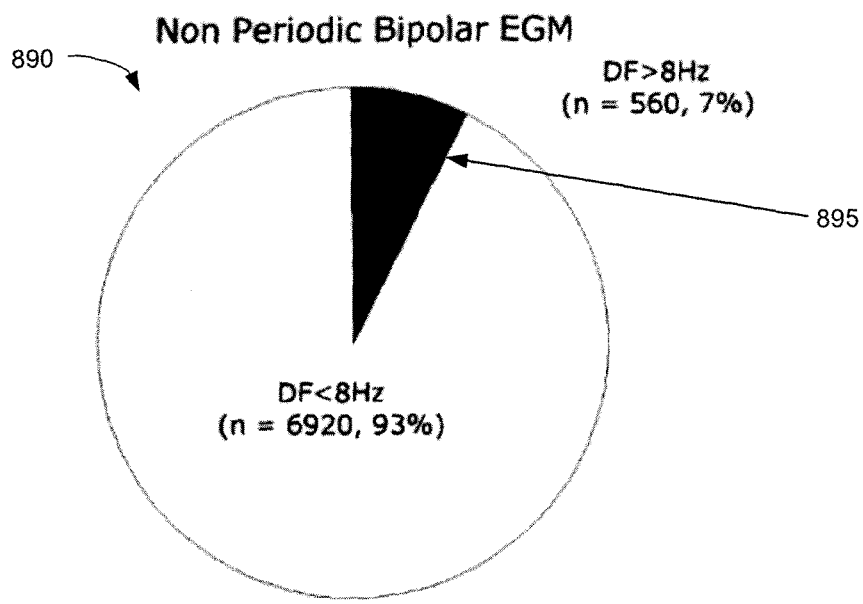
FIG. 15C is a diagram of a pie chart illustrating the proportion of bipolar electrograms having no determined periodicity when using the methods described according to the teachings herein but showing a significant dominant frequency according to dominant frequency analysis.

Referring now to FIG. 15C, shown therein is a pie chart 890 indicating the proportion 895 of bipolar EGM having no periodicity according to the methods described in accordance with the teachings herein where DF analysis shows a significant dominant frequency (>8 Hz). The proportion 895 shown in FIG. 15C includes 560 EGMs out of a total of 7480 aperiodic bipolar EGMs, or 7%.

Figure 15D:
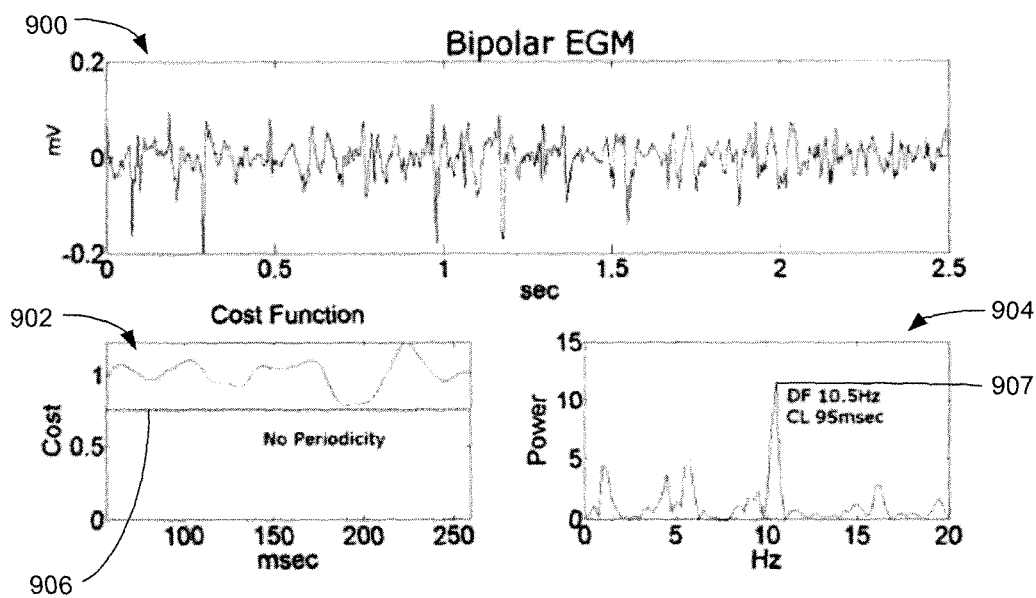
FIG. 15D is a diagram of another bipolar electrogram recorded from the left atrium of a patient, a periodicity cycle length cost function corresponding to the bipolar electrogram, and a plot illustrating the dominant frequency analysis of the bipolar electrogram.

Referring now to FIG. 15D, shown therein is an example of a bipolar EGM 900 corresponding to the proportion 895. As cost function 902 illustrates, there is no local minimum below threshold 906 so the methods described in accordance with the teachings herein determined that there was no periodicity in bipolar EGM 900. In contrast, the DF analysis shown in plot 904 detects periodicity based on a high spectral peak (i.e. >8 Hz) 907 at 10.5 Hz.

The performance of the focal source identification methods described in accordance with the teachings herein were tested in a simulation study against two recent peak detection algorithms, the automatic multiscale peak detection (AMPD) algorithm and an iterative method. The performance of the focal source identification methods was also tested in a simulation study against the conventional dominant frequency analysis method.

Artificial EGM signals with known periodicities with ±5% variations in the periodic cycle length and varying amounts of noise (−3 dB, 0 dB, 3 dB) were used to test all 4 algorithms. The artificial periodic EGM signals were generated by taking real AF bipolar activation templates and repeating them at known cycle lengths (i.e. 150 msec, 185 msec or 195 msec) and with varying amplitudes over a total duration of 2,500 msec. The 'noisy' signals were real AF bipolar EGMs which had no visually-discernible periodicity, but which had occasional aperiodic peaks that could introduce false peaks in the dominant periodic signal. For approximately 5% of the simulated signals, the periodic templates had double potentials. It should be noted that even though the activation peaks are identified on unipolar EGM data, the nature of unipolar EGMs make it susceptible to degradation by various high amplitude noise sources, especially multiple far-field effects such as ventricular beats and AF waves at a distance remote from the recording site. Hence, it is more practical to analyze the corresponding bipolar EGMs for periodic activity and identify associated peaks and then use the positions of those identified peaks to analyze corresponding areas in the unipolar EGMs to identify focal sources. For this reason, the simulated data were designed to simulate bipolar, rather than unipolar data.

The results of the simulations are shown in Table 2, Table 3, FIG. 16 and FIG. 17. Each method's peak annotations were compared to known periodic peak locations. If known and annotated peak locations were closer than 10 ms apart, the annotated peak was considered accurate. The accuracy of an algorithm was defined as the ratio of the number of periodic peaks successfully detected over the entire dataset to the total number of actual periodic peaks in the dataset. As Table 2, Table 3, FIG. 16 and FIG. 17 show, the focal source identification method according to the teachings herein outperformed the other methods. Table 2 also reflects some of the differences between the methods described herein and the dominant frequency analysis methods that were described above with regard to FIGS. 15A-15D.

TABLE 2

Performance of Dominant Frequency method and the method of the present invention for periodic peak detection using bipolar AF EGMs with simulated periodicity (CL 185 msec)

| | Overall Accuracy (%) | | Accuracy in setting of Double Potential (%) | |
| --- | --- | --- | --- | --- |
| SNR | DF | Present Method | DF | Present Method |
| +3 dB (n = 150) | 94 | 92 | 19 | 83 |

The difference in performance can be seen when double potentials are present. The dominant frequency analysis considers both peaks in the double potential, thereby overestimating the dominant frequency and underestimating periodicity cycle length. In contrast, the focal source identification method according to the teachings herein only considers one peak of the double potential which satisfies a periodic constraint (imposed using an independently obtained periodicity).

TABLE 3

Performance of periodic peak detection methods using bipolar AF EGMs with simulated periodicity (CL 150, 185, and 195 msec)

| | Mean Error in Peak Detection (ms) | | | Accuracy (%) | | |
| --- | --- | --- | --- | --- | --- | --- |
| SNR | CLI | AMPD | Present Method | CLI | AMPD | Present Method |
| +3 dB (n = 150) | 19 | 8.0 | 4.5 | 73 | 81 | 96 |
| 0 dB (n = 150) | 27 | 8.5 | 5.4 | 72 | 80 | 94 |
| −3 dB (n = 150) | 34 | 9.7 | 5.5 | 57 | 76 | 89 |

The difference in performance appears to be most pronounced in the cases where aperiodic, but physiologic electrical activity is high and in cases where the peaks vary widely in amplitude over the course of a single recording and hence the genuine peak, i.e. the peak corresponding to the periodic activity, is not the local maximum. The other two peak detection methods (CLI and AMPD) appear to be prone to detecting aperiodic peaks which are not part of the periodic signal. In contrast, the focal source identification method according to the teachings herein is more robust at ignoring aperiodic peaks because only peaks satisfying a periodic constraint (imposed using an independently obtained periodicity) are considered.

Figure 16A:
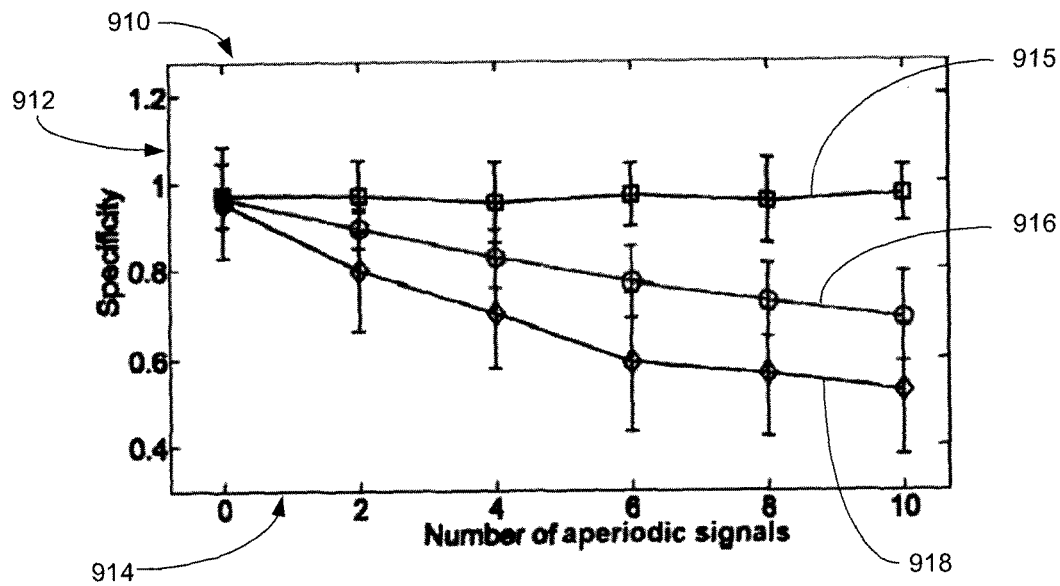
FIG. 16A is a diagram illustrating a plot of the specificity of identifying periodic activations using various methods.

Referring now to FIG. 16A, shown therein is a plot 910 illustrating the specificity 912 of correctly identifying periodic peaks in a bipolar EGM when an increasing number of aperiodic or noisy peaks 914 are introduced into the EGM signal. The aperiodic peaks 914 were introduced randomly into a complex AF bipolar EGM with simulated periodic peaks having a known periodicity cycle length. The simulated bipolar EGMs were analyzed using the methods described in accordance with the teachings herein, an AMPD method and a CLI method. Each method's peak annotations were compared to known peak locations. If known and annotated peak locations were closer than 10 ms apart, the annotated peak was considered accurate.

As plot 910 indicates, the specificity 915 of identifying periodic peaks using the methods described in accordance with the teachings herein appears to be greater than the specificity 916 for the AMPD method and the specificity 918 for the CLI method.

Figure 16B:
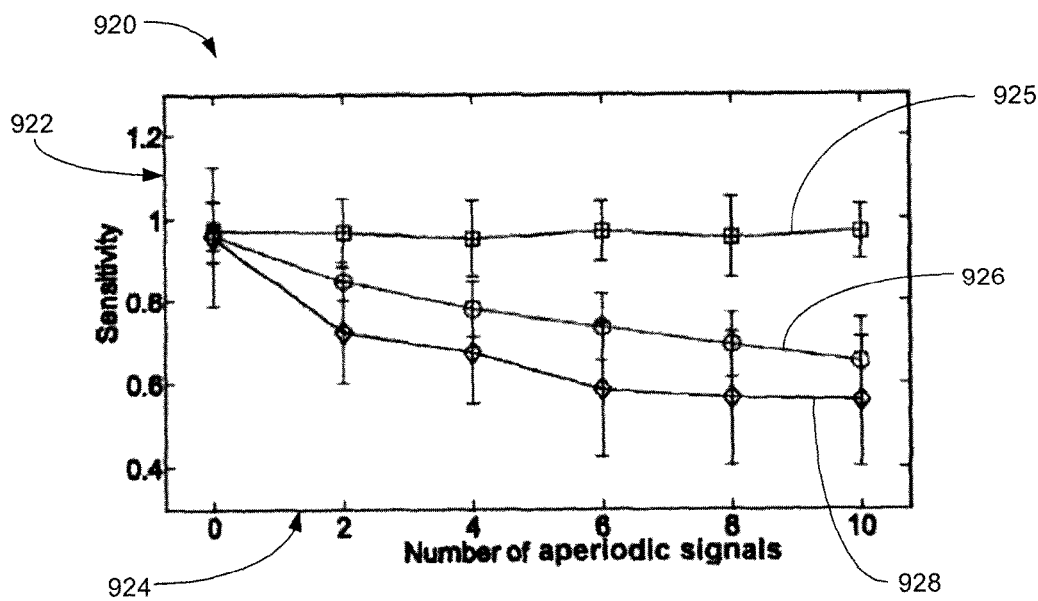
FIG. 16B is a diagram illustrating a plot of the sensitivity of identifying periodic activations using the same methods as in FIG. 16A.

Referring now to FIG. 16B, shown therein is a plot 920 illustrating the sensitivity 922 of various methods for identifying periodic peaks in bipolar EGMs when an increasing number of aperiodic or noisy peaks 924 are introduced into the EGM signal. The aperiodic peaks 924 were introduced randomly into complex AF bipolar EGMs with simulated periodic peaks having known periodicity cycle lengths. The simulated bipolar EGMs were analyzed using the methods described in accordance with the teachings herein, and the AMPD and CLI methods mentioned above.

As plot 920 indicates, in the simulations that were performed, the sensitivity 925 of identifying periodic peaks using the methods described in accordance with the teachings herein was seen to be better than the sensitivity 926 of the AMPD method and the sensitivity 928 of the CLI method.

Referring now to FIGS. 17A-17H, shown therein are various plots of simulated bipolar EGM signals used to derive the specificity plot 910 and the sensitivity plot 920 shown in FIGS. 16A and 16B above. Plot 930 shows a template of a simulated periodic signal peak 932 while plot 935 shows a template of a simulated aperiodic signal peak 934. Plot 940 illustrates a train of ten consecutive periodic signal peaks 932 corresponding to the template shown in plot 930. The periodic signal peaks 932 in plot 940 have a cycle length of 156 ms. Plot 945 illustrates a train of ten consecutive aperiodic signal peaks 934. As can be seen in plot 945, the aperiodic signal peaks 934 appear to be randomly distributed. Combined plot 950 includes a combination of the periodic signal peaks 932 having a cycle length of 156 ms and a random distribution of aperiodic signal peaks 934.

Figure 17A:
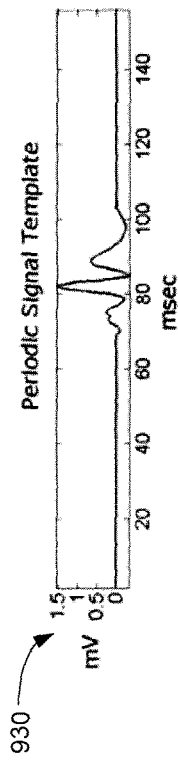
FIG. 17A is a diagram illustrating a plot of a template for a simulated periodic signal.
Figure 17B:
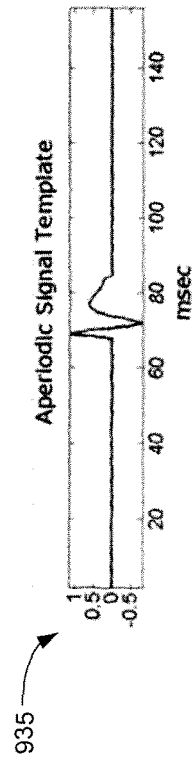
FIG. 17B is a diagram illustrating a plot of a template for a simulated aperiodic signal.
Figure 17C:
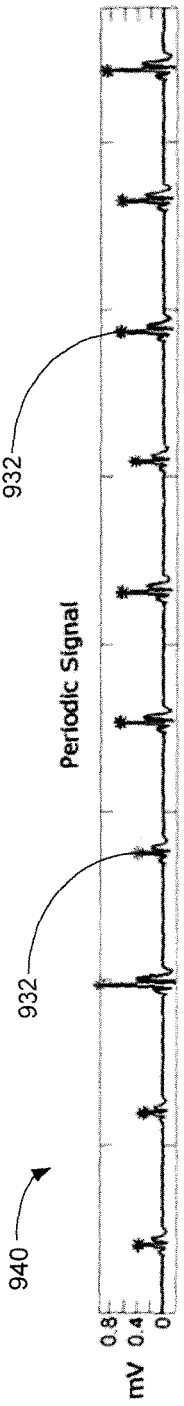
FIG. 17C is a diagram illustrating a plot of a train of 10 of the simulated periodic signals from FIG. 17A.
Figure 17D:
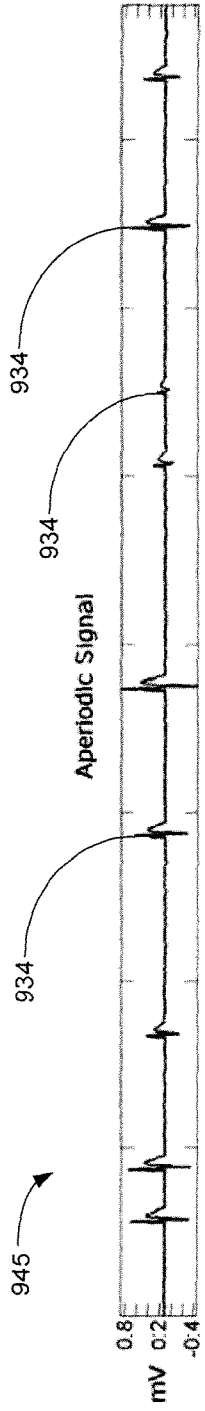
FIG. 17D is a diagram illustrating a plot of a train of 10 of the simulated aperiodic signals from FIG. 17B.
Figure 17E:
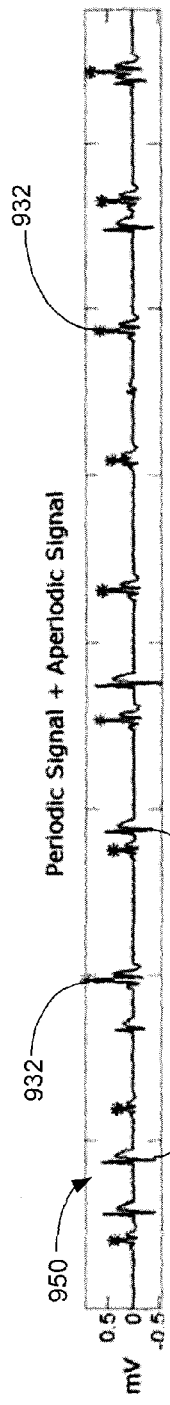
FIG. 17E is a diagram illustrating a plot with a combination of periodic peaks and aperiodic peaks.
Figure 17F:
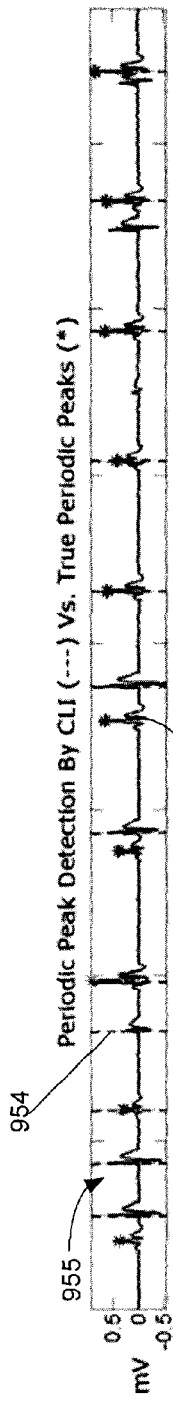
FIG. 17F is a diagram illustrating the plot of FIG. 17E showing the periodic peaks identified using a cycle length iteration (CLI) algorithm.
Figure 17G:
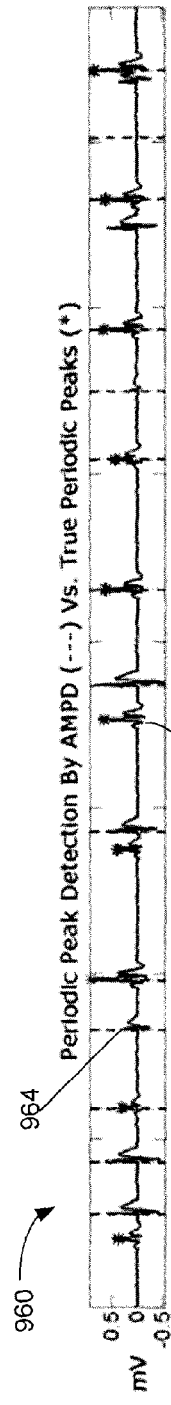
FIG. 17G is a diagram illustrating the plot of FIG. 17E showing the periodic peaks identified using an automatic multiscale peak detection (AMPD) algorithm.
Figure 17H:
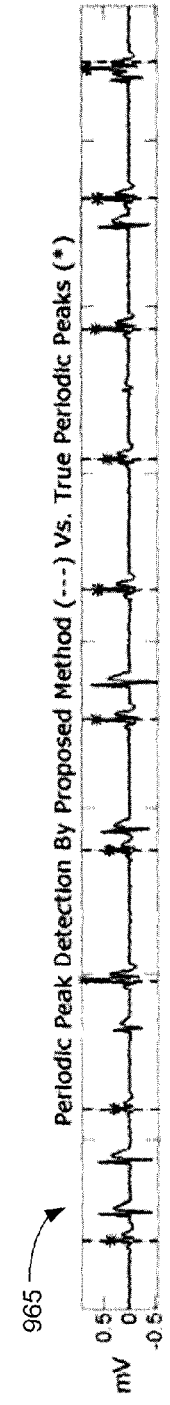
FIG. 17H is a diagram illustrating the plot of FIG. 17E showing the periodic peaks identified using the methods described in accordance with the teachings herein.

Analysis of the combined plot 950 was performed using the CLI method (results shown in FIG. 17F), the AMPD method (results shown in FIG. 17G) and the method described in accordance with the teachings herein (results shown in FIG. 17H).

Plot 955 shows the peaks detected by the CLI method using dashed lines with the true periodic peaks 922 identified by asterisks. As can be seen in plot 955, the CLI method identifies aperiodic peak 954 as one of the periodic peaks and does not identify periodic peak 952 as one of the periodic peaks.

Plot 960 shows the peaks detected by the AMPD method using dashed lines. Once again, we see that the AMPD method has incorrectly identified aperiodic peak 964 as one of the periodic peaks, while missing periodic peak 962.

Plot 965 shows the peaks detected by the methods described in accordance with the teachings herein using dashed lines. As shown in plot 965, the methods described in accordance with the teachings herein were able to correctly identify all the periodic peaks without any false peaks being identified.

It was found that the CLI and AMPD methods, shown in plots 955 and 960 respectively, have a tendency to annotate aperiodic peaks corresponding to local maxima at the expense of the true periodic peaks of lower magnitude. These annotations represent false positive periodic peaks. Advantageously, the methods described in accordance with the teachings herein may avoid such issues by first identifying the periodicity cycle length, and subsequently identifying peaks based on the identified cycle length.

In some cases, embodiments of the focal source identification method 100 can more accurately identify the periodicity cycle length and peaks of received electrical signal sets with double potentials. Double potentials may be present in the electrical signal sets recorded during AF and typically arise from local conduction block. Local conduction block is a discrete area in an organ where a propagating electrical wave cannot pass through, but must travel around it. This produces late activation of the recording electrode and the second potential. Double potentials may be seen as peaks that appear in pairs where the morphology of each peak in the pair may be different from its partner while being very similar to that of every alternate peak. The true periodicity of a signal with double potentials corresponds to the cycle length between every alternate peak.

Figure 18:
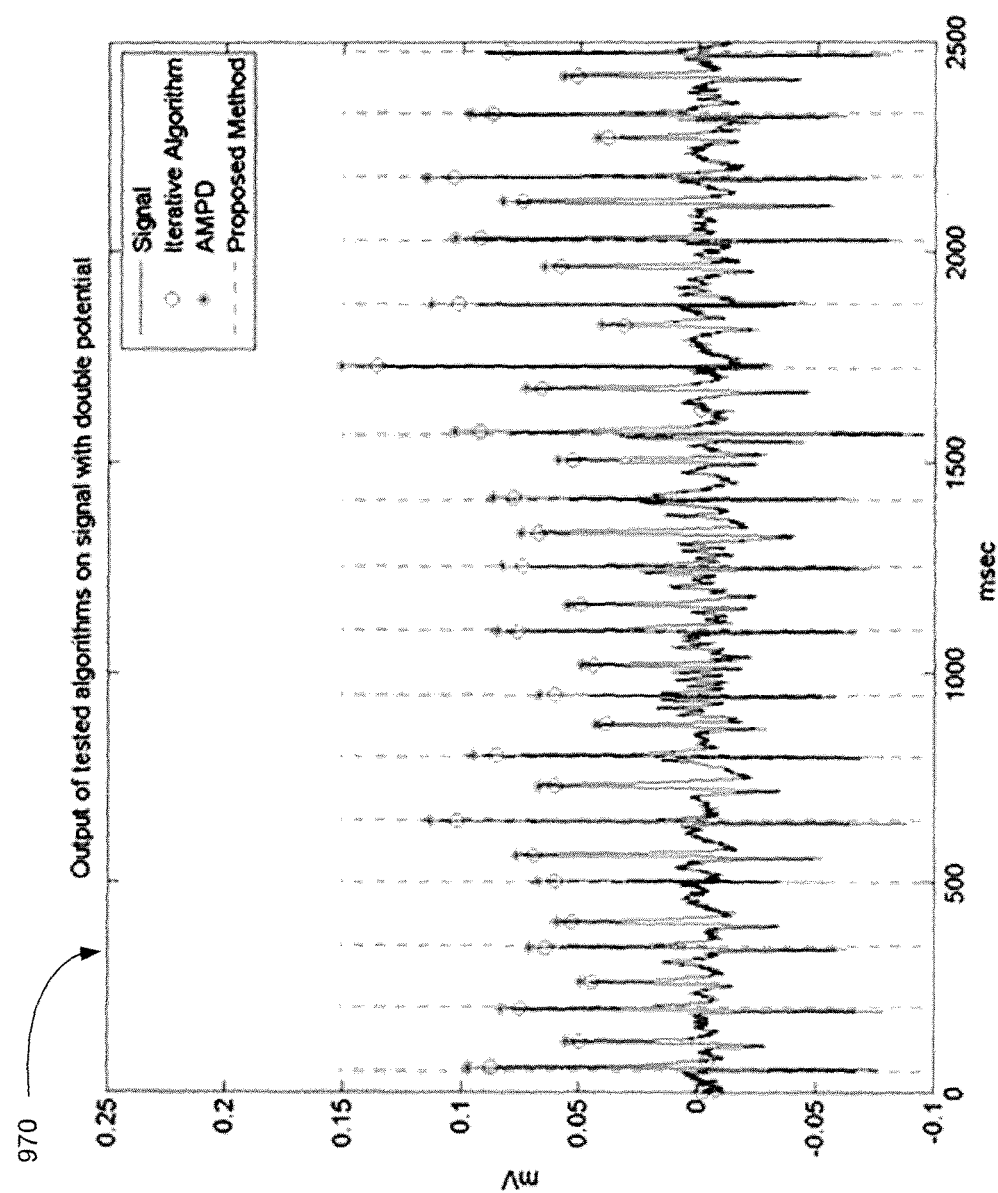
FIG. 18 is a diagram illustrating a plot of an electrogram signal with double potentials with the outputs of various peak detection methods marked.

Referring now to FIG. 18, shown therein is an example plot 970 of the outputs of various methods for identifying the periodic peaks of a bipolar EGM with double potentials recorded during AF in one patient. The results of an iterative algorithm (i.e. CLI), AMPD algorithm and an embodiment of the focal source identification methods described in accordance with the teachings herein with regard to FIGS. 3 to 5 are shown. Both the iterative algorithm and the AMPD algorithm identify all non-noise related peaks in the signal with double potentials. In contrast, the focal source identification method 100 is able to ignore the double potentials because the cycle length of the periodicity is first determined and peaks are then identified based on this cycle length.

Electrical signal sets with double potentials can have periodic activations with two peaks. These two peaks can be referred to as the first peak and the second peak. The correlation value determined for a given periodic cycle length that results in a circular shift where the first peaks overlap with successive first peaks, and the second peaks overlap with successive second peaks will be higher than the correlation value determined for a periodic cycle length that results in a circular shift where the second peaks overlap with the first peaks and vice versa. This may often be the case as the first peaks tend to have a different morphology than the second peaks. Accordingly, the methods described as per the teachings herein appear to be robust in dealing with double-potentials and not be overly sensitive to their existence in that only one peak from a set of double-potentials is tracked (as they should be) rather than both peaks being tracked.

As mentioned above, the system 10 may provide as an output an electronic file or display an image following the acquisition of electrical signal sets and analysis according to the method herein. In some cases, the output may be provided as a list of focal source location. The list may include the periodicity cycle lengths corresponding to those focal source locations. The focal source locations and potentially other locations where electrical signal sets were acquired may be identified in the list (see Table 4 below) using a unique identification number that corresponds to the recording site where the electrical signal set for that focal source location was acquired. The electrical signal sets corresponding to the various recording sites may also be display using a GUI such as GUI 1000 shown in FIG. 19A and GUI 1050 shown in FIG. 19B. The unique identification number may correspond to an identification number assigned by an electroanatomic mapping system. In some cases, this can be done where the electrical signal sets are not acquired directly by system 10, but are acquired using a commercial electroanatomic mapping amplifier and acquisition system. This may allow the anatomic location of the focal source location to be determined (see e.g. FIG. 19C) and tagged on an image of the anatomic region using anatomic data exported from an electroanatomic mapping system.

The outputs from system 10 can enable a user to examine the focal source locations identified, and determine whether to ablate those locations. The outputs may be used as a guide for individualized substrate modification in the treatment of atrial fibrillation.

Referring now to FIG. 19A, shown therein is an example embodiment of a Graphical User Interface (GUI) 1000 that may be displayed to a user on display 16 when the focal source location method is performed on EGM data. The GUI 1000 can display the electrical signals sets to a user as well as various properties of the electrical signal sets that have been determined by the method 100. The GUI 1000 may also display the various portions of an electrical signal set to a user such as a surface ECG 1005, a bipolar EGM 1010 and a unipolar EGM 1015.

The GUI 1000 may also include a correlation value plot 1020 that displays the correlation values corresponding to the plurality of potential cycle lengths. The identified periodicity cycle length 1022 may be displayed along with the confidence level 1024 of the identified cycle length 1022. In this example the periodicity cycle length 1022 has been identified as 146 ms and the confidence level 1024 has been identified as 2.27 standard deviations above the mean correlation value.

The GUI 1000 may be used by system 10 when a plurality of electrical signal sets have been recorded at different locations in an organ of a patient. Each of the electrical signal sets may be analyzed using the various methods described in accordance with the teachings herein. The user may refer to the GUI 1000 to review the plurality of electrical signal sets and the properties derived therefrom.

For example, the GUI may indicate the current electrical signal set 1045 that is being reviewed by the user as well as the number of electrical signal sets 1040 meeting threshold parameters and other criteria. In some embodiments, the threshold parameters and other criteria may be predefined or selected from a set of values. In other embodiments, the threshold parameters and other criteria may be set by the user. The user can use the GUI 1000 to review component data for locations that may be identified as focal sources before considering therapeutic intervention, such as catheter ablation.

The user may also use the GUI 1000 to adjust threshold parameters and predefined amounts. For example, the user may use input button 1025 to adjust the minimum potential cycle length 1028 and input button 1030 to adjust the maximum potential cycle length 1032. In this example, the minimum potential cycle length 1028 has been set to 55 ms while the maximum potential cycle length 1032 has been set to 203 ms.

The user may also use the input button 1035 to adjust the confidence threshold 1038 for determining whether an electrical signal set is periodic. In this example, the confidence threshold 1038 has been set to 2 standard deviations above the mean correlation value.

Referring now to FIG. 19B, shown therein is another example embodiment of a GUI 1050 that may be shown to a user on display 16 when the focal source location method is performed on EGM data. GUI 1050 is an example where a plurality of electrical signal sets including bipolar EGMs 1060a-1060g and corresponding unipolar EGMs 1070a-1070g recorded simultaneously are displayed. For each bipolar EGM 1060, the periodicity cycle length 1062 and corresponding confidence level 1064 (i.e. correlation value) is displayed. The periodicity cycle length 1062 can be displayed for each bipolar EGM even if the confidence level 1064 for at least some EGMs is not above the cycle length confidence threshold (threshold correlation value)

In the example shown in GUI 1050, the bipolar EGM 1060d and unipolar EGM 1070d correspond to a recording location that was identified as a focal source location using the methods described according to the teachings herein. The other bipolar EGMs 1060a-c, 1060e-g and unipolar EGMs 1070a-c, 1070e-g were acquired simultaneously from locations near to the focal source location using a multi-electrode catheter.

In GUI 1050, the periodic peaks in the bipolar EGM 1060d and unipolar EGM 1070d can be annotated with a peak annotation line such as a red dashed line. The peak annotation line can be extended to the EGMs for the adjacent recording sites to evaluate activation times relative to the focal source location identified.

Referring now to FIG. 19C, shown therein is another example embodiment of a GUI 1100 that may be shown to a user on display 16 when the focal source location method is performed on EGM data. GUI 1100 is an example of a periodicity map window that may be shown to the user after determining the periodicity cycle lengths for a plurality of bipolar electrograms.

GUI 1100 includes a three-dimensional anatomic shell of a patient's left atrium. The three-dimensional anatomic shell is an example of an anatomic shell that may be generated by exporting anatomic data from a commercial three-dimensional electroanatomic mapping system, such as those discussed above. The displayed anatomic shell may be rotated by a user of system 10 using user interface 18, e.g. a mouse.

The periodicity cycle length identified for all bipolar electrograms considered be periodic by the methods described in accordance with the teachings herein can be shown on the anatomic shell using a periodicity scale 1130. In FIG. 19C, the periodicity scale is shown in gray-scale, but it may also be a color scale. Regions of periodicity such as region 1120 can be identified on the anatomic shell by shades or colors corresponding to the periodicity scale 1130. This may permit spatial gradients in periodicity cycle length to be evaluated.

Focal source locations 1110 can also be identified on the anatomical shell shown in GUI 1100. This may allow a user to relate the focal source locations 1110 to the periodicity cycle length gradients. This may provide greater confidence to a user of the validity of the identified focal source location.

In some cases, the output may be provided as a list in an electronic file or displayed as a list on display 16. Table 4 below shows an example of an output list that may be provided to a user of system 10 after a plurality of focal source locations have been identified in accordance with the teachings herein. Table 4 identifies each focal source location using a point identification number. The list also includes the multielectrode catheter identification number for the acquisition of the electrical signal set along with the specific the bipolar electrode pair and constituent unipolar electrodes used to record the focal source. The periodicity cycle length for each focal source location is also identified along with the confidence level or correlation value for that focal source location. Finally, in Table 4, a unique identification number corresponding to a point in an electroanatomic mapping system (here the CARTO™ system manufactured by Biosense Webster). As mentioned above, the unique identification number may enable the focal source locations to be identified in the electroanatomic mapping system, as discussed with reference to FIG. 19C, above.

TABLE 4

Example of Output List of Identified Focal Source Locations

| Point | Cath. ID | Bipole | Unipole 1 | Unipole 2 | Periodicity CL (msec) | Confidence | Carto ™ ID |
|---|---|---|---|---|---|---|---|
| 1 | 2 | 4 | 7 | 8 | 123 | 10.24 | 14 |
| 2 | 10 | 1 | 1 | 2 | 131 | 13.89 | 91 |
| 3 | 14 | 5 | 9 | 10 | 123 | 14.34 | 135 |
| 4 | 14 | 4 | 7 | 8 | 138 | 12.61 | 134 |
| 5 | 19 | 5 | 9 | 10 | 145 | 11.6 | 185 |
| 6 | 31 | 1 | 1 | 2 | 148 | 11.56 | 301 |
| 7 | 33 | 1 | 1 | 2 | 129 | 14.29 | 321 |
| 8 | 41 | 2 | 3 | 4 | 140 | 14.34 | 402 |
| 9 | 41 | 3 | 5 | 6 | 140 | 12.64 | 403 |
| 10 | 47 | 6 | 11 | 12 | 119 | 17.67 | 466 |
| 11 | 47 | 5 | 9 | 10 | 125 | 10.64 | 465 |
| 12 | 47 | 4 | 7 | 8 | 129 | 10 | 464 |
| 13 | 48 | 6 | 11 | 12 | 119 | 12.36 | 476 |
| 14 | 48 | 7 | 13 | 14 | 148 | 19.67 | 477 |
| 15 | 50 | 2 | 3 | 4 | 138 | 14.91 | 492 |
| 16 | 50 | 3 | 5 | 6 | 138 | 19.07 | 493 |
| 17 | 51 | 2 | 3 | 4 | 133 | 10.01 | 502 |
| 18 | 51 | 3 | 5 | 6 | 138 | 10.84 | 503 |

In some cases, an electrical signal set recorded at a location in an organ of a patient may have more than one significant periodicity. Various cycle length detection and peak detection methods, such as those described herein, can be iteratively applied to such a signal using a multi-periodicity detection method to identify all the significant periodicities in the recorded electrical signal set.

Figure 20:
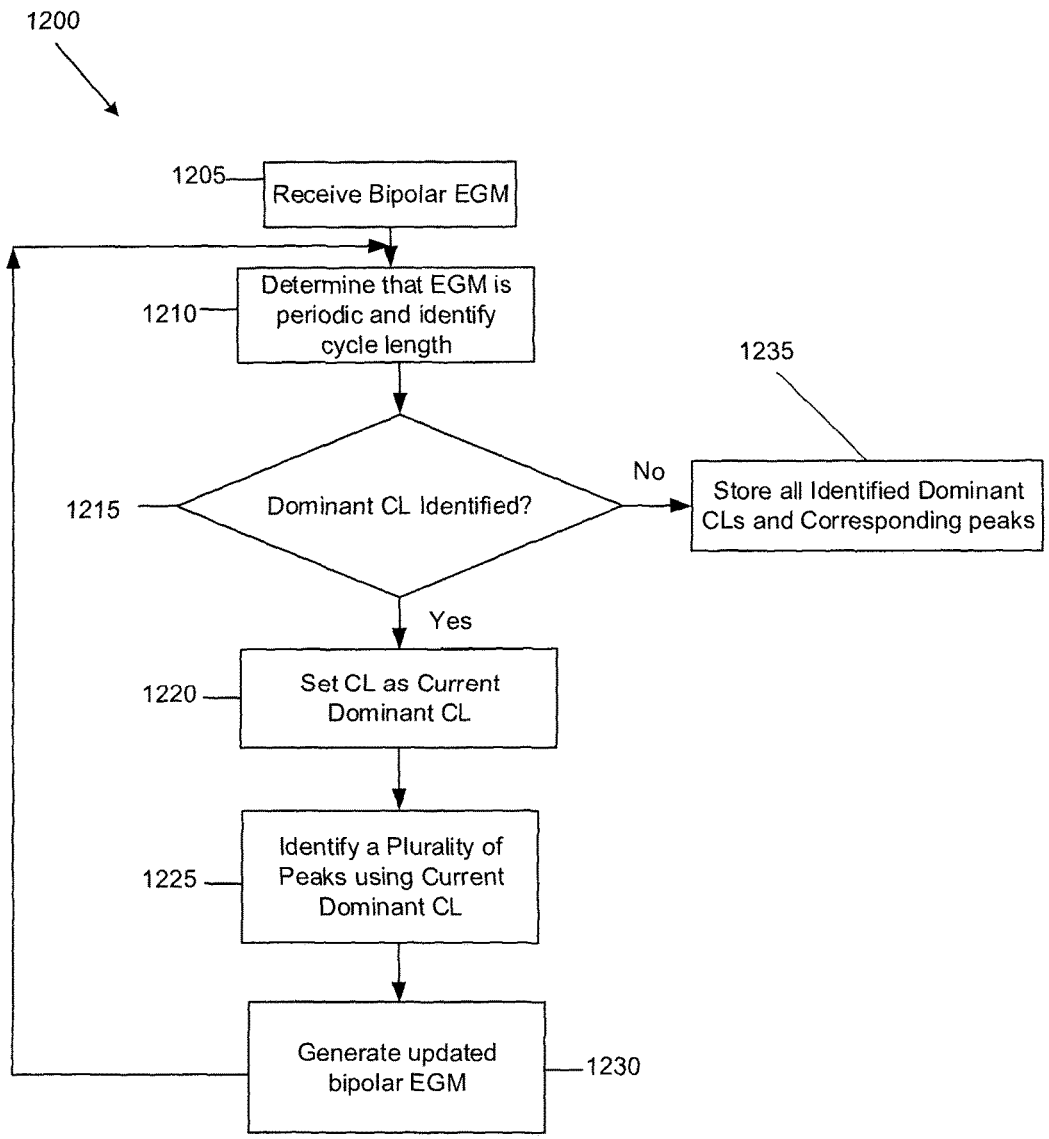
FIG. 20 is a flowchart of an example embodiment of a multiple periodicity detection method that can be used by the system of FIG. 1.

Referring now to FIG. 20, shown therein is a flowchart of an example embodiment of a multi-period identification method 1200. The method 1200 is an iterative method that can be used to identify multiple significant periodicities in an electrical signal set representing electrophysiological activity for an organ.

At 1205 a bipolar EGM is obtained. At 1210, the electrical signal set is determined to be periodic and a periodicity cycle length of the electrical signal is identified. The periodicity and cycle length of the electrical signal set can be identified using the various methods described in accordance with the teachings herein that are suitable.

At 1215, the method 1200 determines whether a dominant periodicity has been identified. If a dominant periodicity cycle length is identified in the electrical signal set (for example, at 245 of method 200), the dominant periodicity cycle length is set as the current dominant periodicity cycle length at 1220. If a dominant periodicity cycle length is not identified in the electrical signal set, all previously identified dominant periodicity cycle lengths and the corresponding pluralities of peaks will be stored, such as in databases 38, at 1235.

At 1225, a plurality of peaks are identified in the EGM that are associated with the current dominant periodicity cycle length. The plurality of peaks can be identified based on the current dominant periodicity cycle length using any suitable peak detection method, such as the methods described in accordance with the teachings herein. The plurality of peaks and the current dominant periodicity cycle length can be noted, or temporarily stored such as in databases 38, so that they can later be stored when method 1200 stores all identified periodicity cycle lengths and corresponding pluralities of peaks at 1235.

At 1230, the plurality of peaks that were identified at 1225 may be used to generate an updated bipolar EGM that can be used to identify any remaining significant periodicities in the original bipolar EGM. The updated bipolar EGM can be generated by blanking the previous bipolar EGM over a window around each peak in the plurality of peaks identified at 1225 in order to remove the plurality of peaks that were identified as being associated with the previous dominant periodicity cycle length. The window may be a time based window. For example, the window may be a 50 msec window around each of the peaks in the plurality of identified peaks.

Figure 21C:
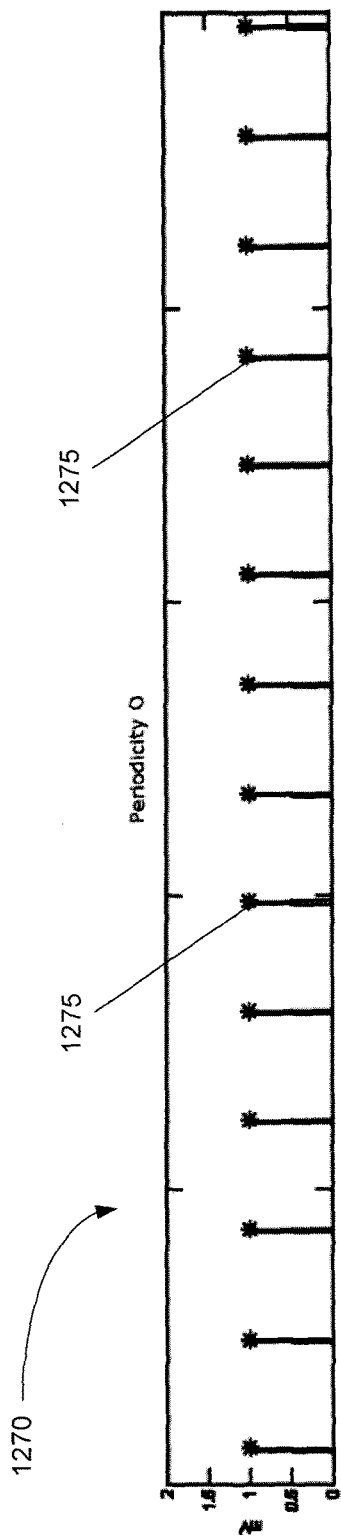
FIG. 21C is a diagram illustrating an example plot of a simulated electrogram signal with a periodic signal having a third cycle length.

Reference will now be made to FIGS. 21A-21D. FIG. 21A shows a plot 1250 of a first simulated periodic signal with peaks 1255 identified by diamonds having a cycle length of 111 ms. FIG. 21B shows a plot 1260 of a second simulated periodic signal with peaks 1265 identified by squares having a cycle length of 149 ms. FIG. 21C shows a plot 1270 of a third simulated periodic signal with peaks 1275 identified by asterisks having a cycle length of 186 ms.

Figure 21D:
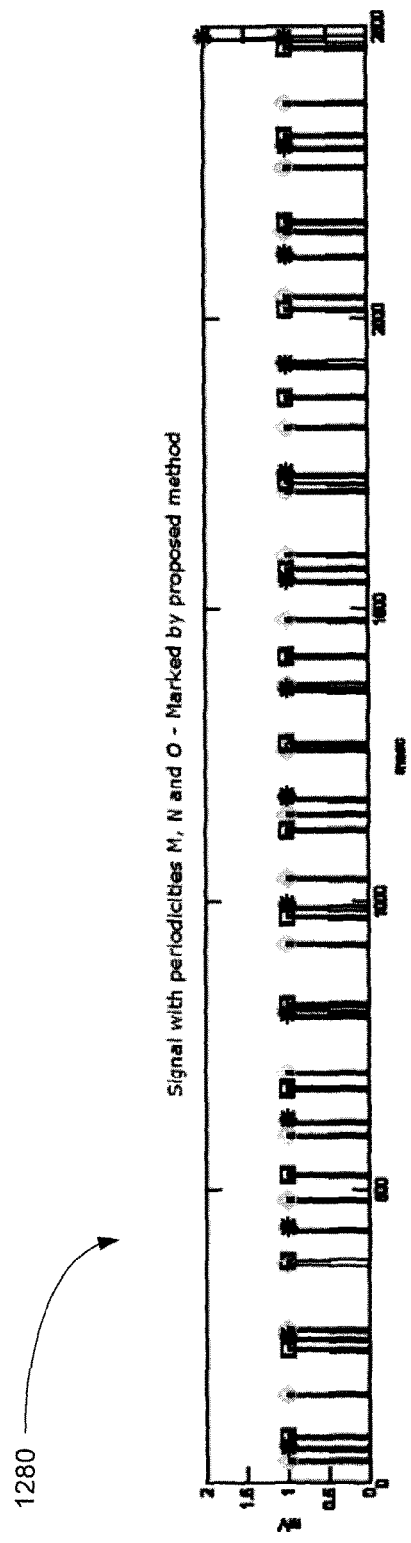
FIG. 21D is a diagram illustrating an example plot of a simulated electrogram signal composed of the periodic signals from FIG. 21A, FIG. 21B, and FIG. 21C where the peaks identified by a multiple periodicity detection method are marked.
Figure 22:
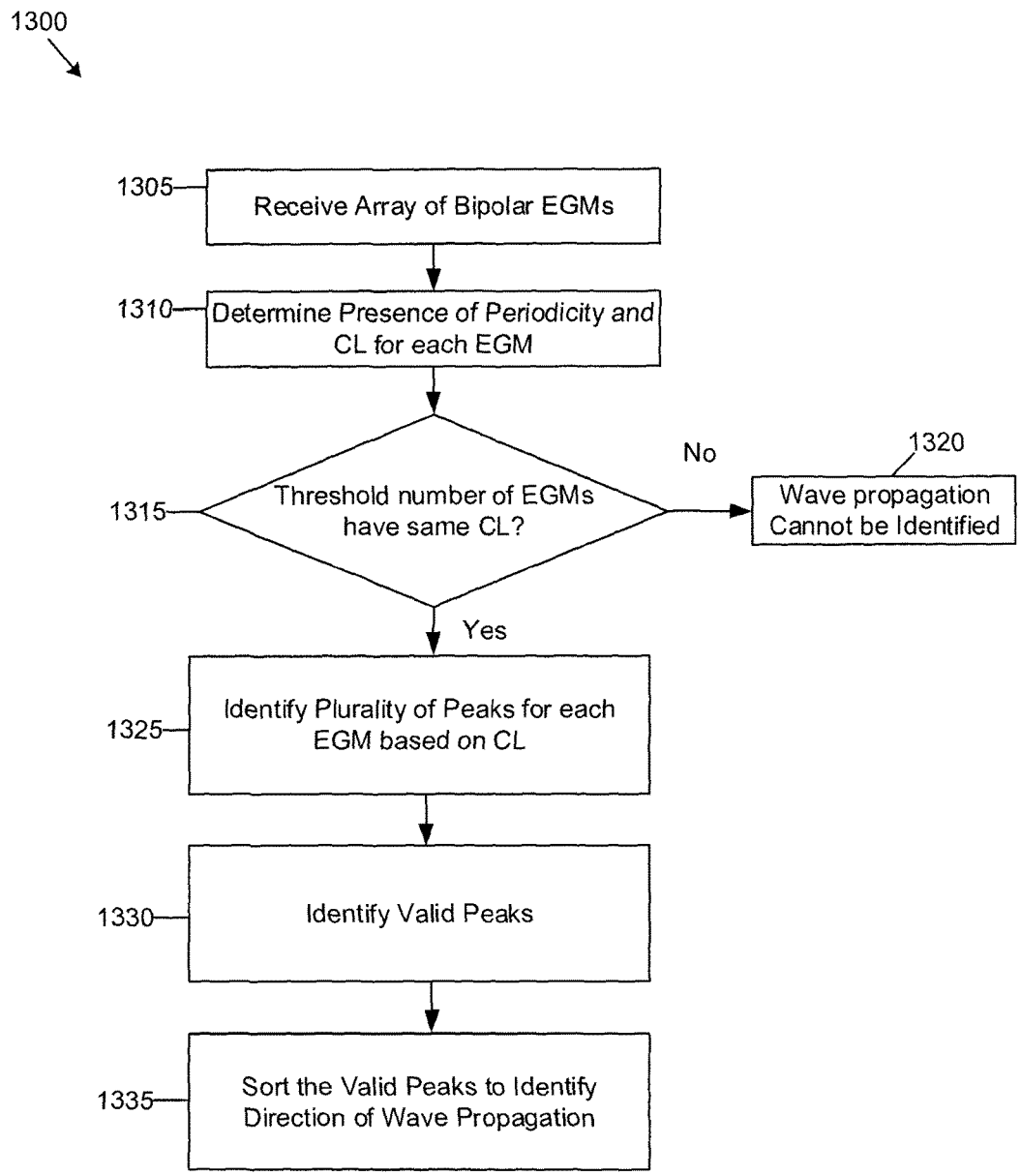
FIG. 22 is a flowchart of an example embodiment of a propagating wave evaluation method that may be used by the system of FIG. 1.

FIG. 21D shows a plot 1280 where the signals from plots 1250, 1260 and 1270 are combined. Plot 1280 is an example of a plot of an EGM signal corresponding to an AF bipolar EGM with multiple periodicities, in this case three periodic signals. The methods described in accordance with the teachings herein, such as method 1200 described above, were applied to the signal shown in plot 1280. Using these methods, the three periodicity cycle lengths were extracted and the method identified the peaks corresponding to each of the periodicity cycle lengths shown in FIGS. 21A-21C.

Table 5 below shows the performance of the methods described in accordance with the teachings herein in detecting 3 different periodic activations having periodicity cycle lengths of 111 ms, 186 ms, and 149 ms respectively. Table 5 shows the performance of the methods described in accordance with the teachings herein when the simulated periodic signals are repeated over 2.5 seconds and contaminated by increasing numbers of aperiodic activations.

The simulations that were analyzed were repeated 350 times. In each of the 350 simulations, the location of the aperiodic activations was varied randomly. The sensitivity and specificity of detecting the 3 periodic activations is shown above in Table 5. A sensitivity of 100% would indicate that all periodic peaks were detected, while a specificity of 100% would indicate that false detection of periodic peaks did not occur. As Table 5 illustrates, the methods described in accordance with the teachings herein show very good sensitivity and specificity even when the signals are contaminated with 5 aperiodic peaks.

TABLE 5

Performance of multiple periodicity detection methods using simulated peak signals with periodicity CL 111, 186, and 149 msec

| | No. of Aperiodic Activations | | | |
| --- | --- | --- | --- | --- |
| | 2 | 3 | 4 | 5 |
| Sensitivity (%) | 93 | 94 | 93 | 90 |
| Specificity (%) | 96 | 97 | 93 | 90 |

As mentioned above, some embodiments of the systems and methods in accordance with the teachings herein may be used to substantially simultaneously capture a plurality of electrical signal sets from a plurality of recording locations in an organ of a patient. This may be done using a multi-electrode catheter, such as the commercially available multi-electrode catheters from Biosense Webster (Pentarray™ and Lasso™) and St Jude Medical (Spiral™). When multiple electrical signal sets from various locations are recoded simultaneously, the systems and methods described according to the teachings herein may be used to evaluate activation patterns, or the direction of wave propagation.

Wave propagation may be evaluated to identify an earliest activation location that is indicative of a focal source location. An example embodiment of a method 1300 for evaluating wave propagation will now be described with reference to FIG. 22. The multiple electrical signal sets acquired simultaneously may be stored as an array. At 1305, the array of bipolar EGMS corresponding to the multiple recording locations is obtained.

At 1310, the presence of periodicity and the periodicity cycle length are identified for each EGM in the array. A first subset of the plurality of electrical signal sets in the array may be identified as having periodicity. The periodicity cycle lengths for the first subset of electrical signal set can also be determined. The presence of periodicity and periodicity cycle length may be identified using the various methods described in accordance with the teachings herein.

At 1315, the periodicity cycle lengths identified for the plurality of EGMs in the array are analyzed to determine whether a certain number of these EGMs have a similar periodicity cycle length. The electrical signal sets having similar periodicity cycle lengths may be referred to as a second subset of electrical signal sets in the first subset. If there is not a certain number of EGMs with a similar periodicity cycle length, a propagating wave cannot be identified and the method 1300 ends at 1320.

Similar periodicity cycle lengths may refer to cycle lengths that do not differ by more than a certain percentage. For example, a similarity threshold percentage may be set at +/−5%, so that cycle lengths may be considered similar to other cycle lengths within +/−5%. A wave threshold for the number of EGMs having similar cycle lengths may similarly be set as a threshold proportion of the total number of EGMs in the array. For example, if the threshold proportion is set at 70%, then greater than 70% of the EGMs in the array would have to have similar cycle lengths in order for the propagating wave to be identified.

If there is a threshold number of EGMs with similar periodicity cycle lengths, the plurality of peaks associated with the similar cycle length for each EGM in the second subset can be identified at 1325. These peaks may be identified using various peak detection methods, such as the methods described in accordance with the teachings herein. An example of a sub-process for identifying the plurality of periodic peaks from multiple EGMs will be described in further detail below with reference to FIG. 23.

At 1330, the plurality of valid peaks for each electrical signal set in the second subset of electrical signal sets can be identified. Each peak in the plurality of peaks identified at 1325 may be identified as a valid peak if they satisfy peak validity criteria. An example of a sub-process for identifying valid peaks is described with reference to FIG. 24 below.

At 1335, the plurality of valid peaks for the EGMs in the array identified at 1330 can be temporally sorted to identify the direction of wave propagation. This may occur when the plurality of valid peaks have propagating wave characteristics. Temporal sorting may be performed by identifying in order the valid peaks in the EGM array from the valid peak with the earliest activation onset to the valid peak having the latest activation onset. Temporal sorting may be performed by sorting the second subset of electrical signal sets in order of increasing activation time defined by timing of the identified plurality of valid peaks for each electrical signal set in the second subset of electrical signal sets.

Valid peaks that correspond to the similar periodicity cycle length across consecutive EGMs can be tracked. For example, in some cases the peaks may be tracked across successive EGMs using a nearest neighbor analysis within a search window. In other embodiments, other tracking methods may be used such as, but not limited to, cross-correlation, mean shift algorithms, and multiple hypothesis tracking algorithms. An example sub-process for sorting a plurality of valid peaks is described below with reference to FIG. 25.

The direction of wave propagation can be identified as a spatial vector of activation that travels from the EGM having the earliest activation onset periodicity peak to the EGM having the latest onset periodicity peak. The median of all the shifts across successive EGMs can be taken as the propagation of the activation process across neighboring electrograms. In some cases, an earliest activation location (corresponding to the recording site of the earliest activation peak time) may be identified.

Figure 23:
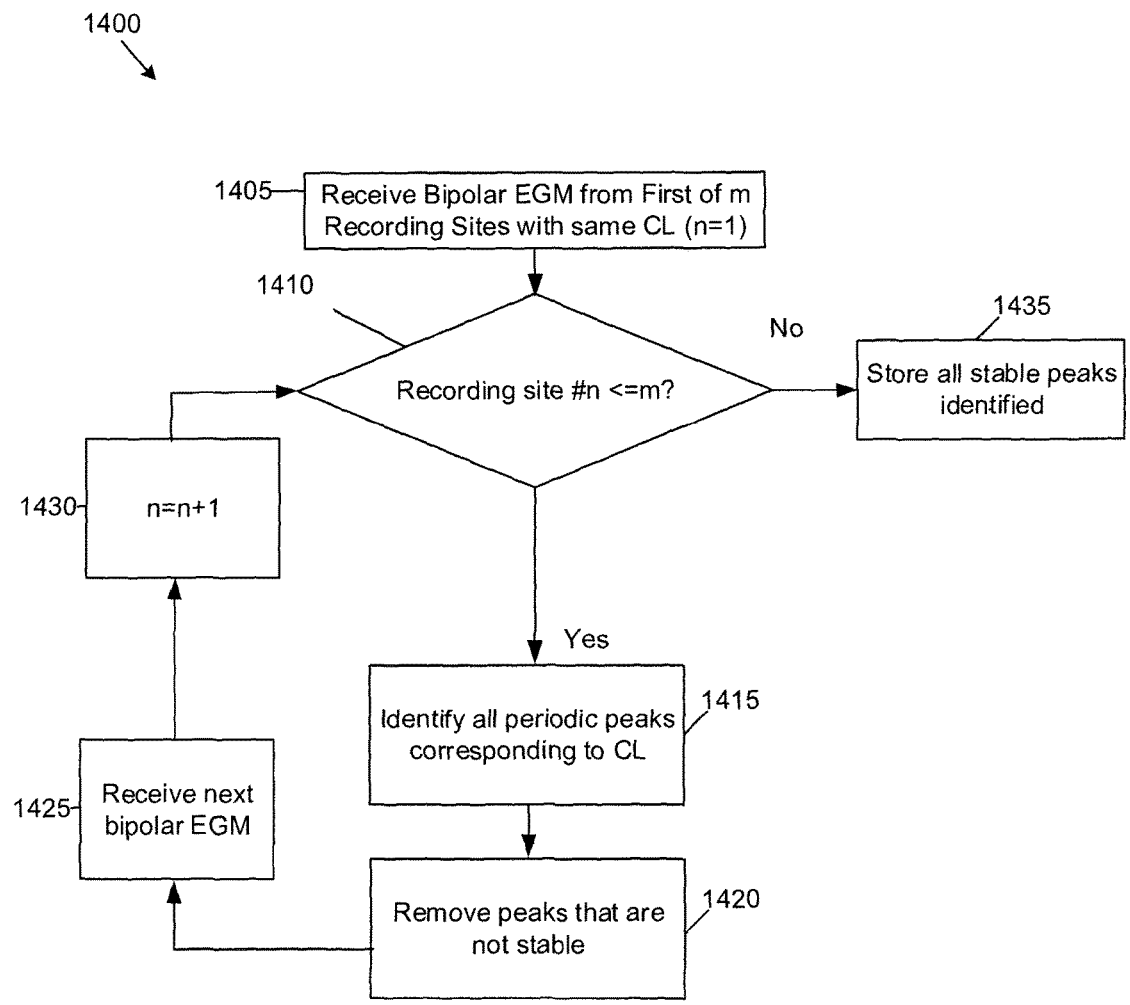
FIG. 23 is a flowchart of an example embodiment of a peak identification sub-process that can be used by the propagating wave evaluation method of FIG. 22.

Referring now to FIG. 23, shown therein is a flowchart of an example embodiment of a sub-process 1400 for identifying a plurality of stable peaks for each EGM. Sub-process 1400 is an example of a sub-process that may be performed at step 1325 of method 1300 to identify peaks corresponding to the similar periodicity cycle lengths of the EGMs being analyzed.

As 1405, a bipolar EGM from a first recording site is received. The bipolar EGM may be one of the bipolar EGMs in the array of bipolar EGMs received at 1305. However, sub-process 1400 may be performed only for those bipolar EGMs having the same dominant periodicity cycle length as determined in method 1300 for example. For ease of understanding, the number of bipolar EGMs having the same dominant cycle length will be referred to as 'm' (m may also be considered the number of electrode recording sites from a simultaneous multi-electrode recording having the same periodicity cycle length). Upon receiving the first bipolar EGM from the array, a counter 'n' is set to 1.

As 1410, an iterative process begins for determining the periodic peaks corresponding to each of the m bipolar EGMs. At 1410, it is determined whether the counter n is less than or equal to m. If this condition is true, then method 1400 proceeds to 1415. If n is greater than m, then all bipolar EGMs have been analyzed. Accordingly, method 1400 would proceed to 1435, where method 1400 ends as all stable periodic peaks corresponding to the same cycle length have been identified.

If further bipolar EGMs must be analyzed (i.e. n is less than or equal to m), at 1415 the periodic peaks in the current bipolar EGM corresponding to the dominant cycle length are identified. The periodic peaks may be identified using various methods described in accordance with the teachings herein such as method 300.

Once all periodic peaks (referred to as potential peaks) corresponding to the similar periodicity cycle length are identified at 1420 the periodic peaks that are not temporally stable are removed. Stable peaks may be identified using various methods, such as the methods described above with reference to step 425 of method 400. Once all the peaks that are not temporally stable have been removed, the remaining peaks should contain all of the temporally stable peaks corresponding to the dominant periodicity cycle length for the current bipolar EGM. The temporally stable peaks can be stored, for example, in database 38.

At 1425, if there are remaining bipolar EGMs to be analyzed, the next bipolar EGM is received. The bipolar EGM may be another of the bipolar EGMs from the array received at 1305. At 1430, the counter n is incremented and method 1400 returns to 1410 where it is determined whether all recording sites have been analyzed. If all recording sites have been analyzed, the method ends at 1435 and all the temporally stable peaks are stored.

It will be apparent to the skilled reader that various modifications to method 1400 can be made without affecting the outcome of method 1400. For instance, the counter n may be incremented and compared with the total number of bipolar EGMs 'm' prior to retrieving a subsequent EGM for analysis.

Figure 24:
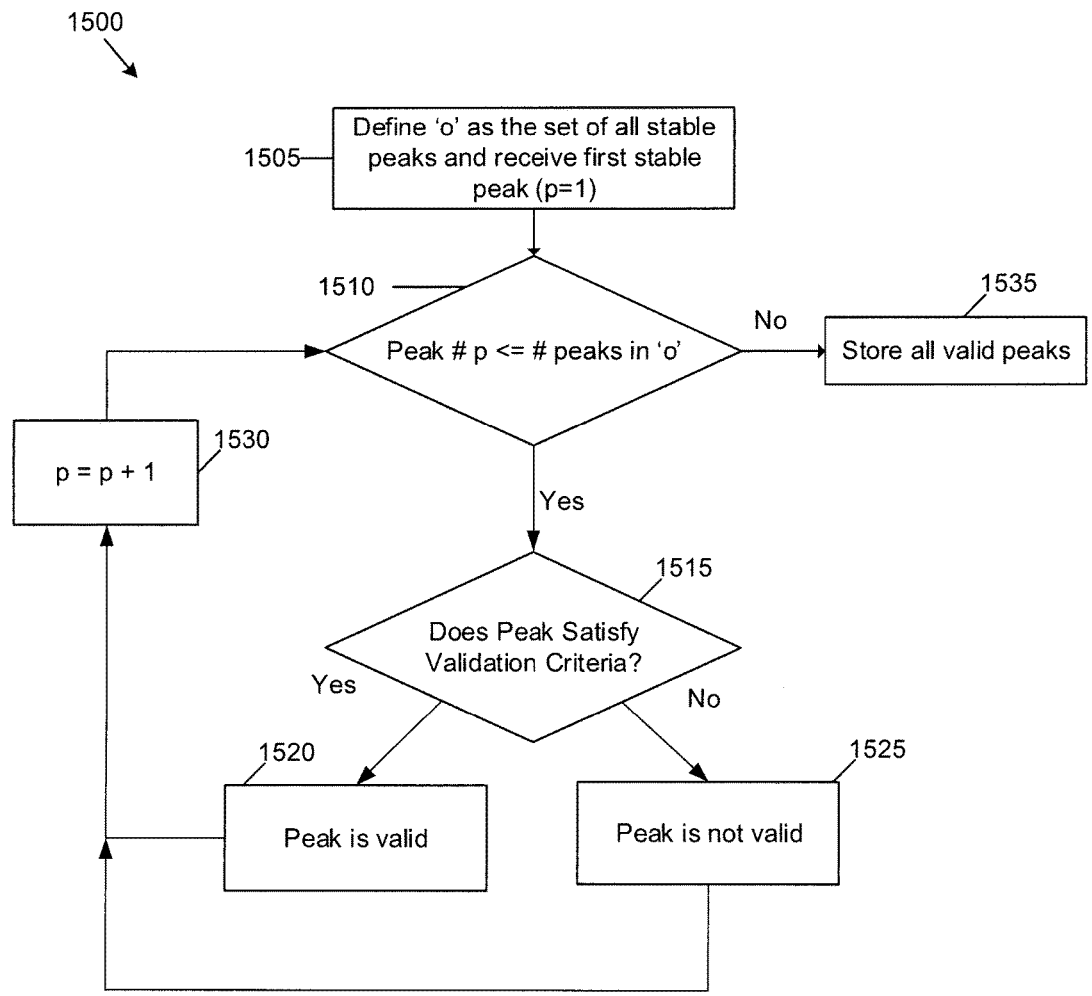
FIG. 24 is a flowchart of an example embodiment of a peak validation sub-process that can be used by the propagating wave evaluation method of FIG. 22.

Referring now to FIG. 24, shown therein is a flowchart of an example embodiment of a sub-process 1500 for determining if the periodic activation peaks are valid. Accordingly, method 1500 may be applied to consider the validity of the stable peaks identified using method 1400, for example. For each electrical signal set considered, the plurality of valid peaks for that electrical signal set may be identified as a valid subset of the stable peaks for that electrical signal set that satisfy validation criteria. Validity of periodic peaks as it is used in method 1500 refers to whether the periodic peak appears to be a valid constituent of a propagating wave. The total number of stable peaks being examined in method 1500 may be referred to as the set of peaks 'o'.

At 1505, the first stable periodic peak is received. A peak number counter 'p' can also be initialized to 1 at this point. The first stable peak may refer to the earliest stable peak identified from the array of bipolar EGMs received at 1300. However, it will be apparent to the skilled reader that the earliest stable peak does not need to be analyzed first.

At 1510, it is determined whether all the stable peaks have been analyzed. This can be done by comparing the value of 'p' to the number of peaks in the set 'o' at 1510. If p is less than or equal to the number of peaks in 'o', then there are remaining peaks to be validated and method 1500 proceeds to 1515.

At 1515, the current peak is examined to determine if it satisfies validation criteria. The validation criteria may be applied to determine if the peak may be a constituent of a propagating wave. For instance, a peak may be considered valid if i) the nearest peak in either of the previous two electrode recordings (i.e. an earlier neighboring peak) is before the present peak and within one periodicity cycle length of the present peak; or ii) the nearest peak in either of the two subsequent electrode recordings (i.e. a later neighboring peak) is after and within one periodicity cycle length of the current peak being analyzed.

If the peak validation criteria are satisfied, then method 1500 proceeds to 1520 where the current peak is considered to be a valid peak. If the peak validation criteria are not satisfied, the current peak is considered to not be a valid peak at 1525. Following identification of the peak as either valid or not valid, method 1500 proceeds to 1530.

At 1530, the activation counter 'p' is increased by 1. A subsequent activation peak (if any are remaining) may be retrieved at this point, or it may be retrieved after the incremented counter 'p' is compared to the total number of peaks in 'o' at 1510. If there are further peaks to be analyzed, then steps 1515-1530 will be repeated for each peak. If 'p' is greater than the number of peaks in 'o', this indicates that all of the stable peaks have been analyzed for validity. At this point, method 1500 proceeds to 1535 where all the validated peaks are stored, for instance in databases 38, and method 1500 ends.

Figure 25:
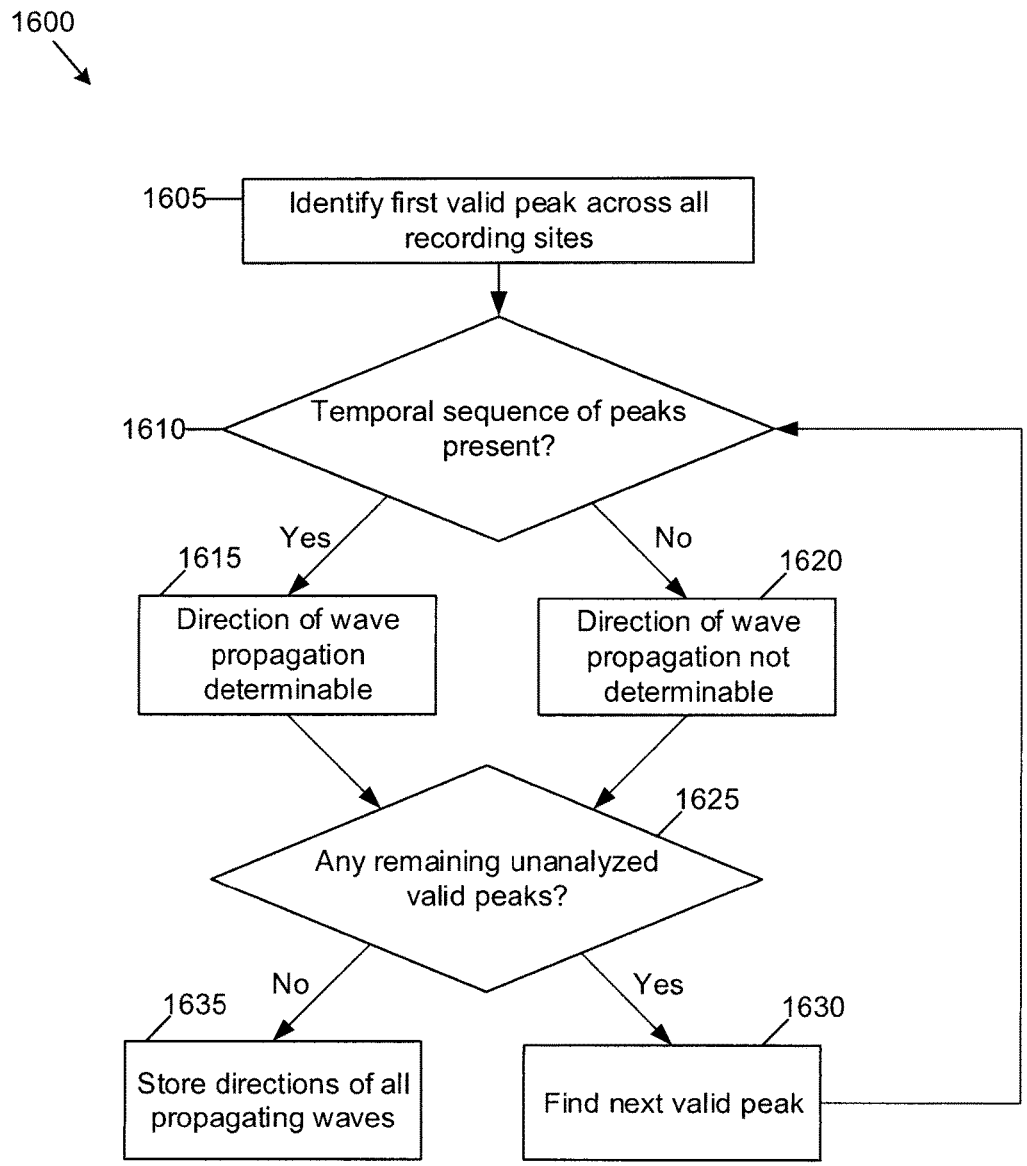
FIG. 25 is a flowchart of an example embodiment of a propagating wave direction identification sub-process that can be used by the propagating wave evaluation method of FIG. 22.

Referring now to FIG. 25, shown therein is a flowchart of an example embodiment of a sub-process 1600 for identifying the direction of wave propagation among a plurality of bipolar EGMs. Method 1600 is an example of a process that may be performed at step 1335 in method 1300. Method 1600 may identify the direction of a propagating wave if the plurality of valid peaks in the bipolar EGMs meet certain predefined propagating wave characteristics.

At 1605, the first valid peak across all recording sites may be identified. The series of valid peaks identified in method 1500 may be examined starting from the beginning (time=0) of a multi-electrode recording that was obtained using an array of bipolar EGMs. The first valid periodic peak, meaning the earliest valid peak in time in the array of bipolar EGMs may be identified as the first valid peak.

At 1610, the plurality of bipolar EGMs may be analyzed to determine if a temporal sequence of peaks are present. This may also be referred to as determining if the plurality of peaks have propagating wave characteristics. This can be done using a running window having a window size equivalent to the periodicity cycle length which can be applied to the array of bipolar EGMs beginning at the first valid peak. If a sequence of valid peaks greater than a wave threshold amount is present in the running window, then the current sequence in the window may enable the direction of wave propagation to be determined as shown at 1615. In such cases, the temporal sequence of the periodic peaks identified at 1610 may be used to determine the direction of wave propagation. The temporal sequence of valid peaks can be sorted to identify the direction of the propagating wave.

The wave threshold may be set as a percentage of the number of recording sites. For example, a sequence of valid peaks that are identified in more than 70% of the total number of recording sites within one periodicity cycle length may be considered adequate to evaluate the direction of wave propagation. If the sequence does not include the wave threshold number of peaks, then the direction of wave propagation may be considered indeterminable at 1620.

In either case, method 1600 proceeds to 1625 to determine if there are any remaining valid peaks that have not yet been considered. For example, this could be determined by determining if the running window has reached the end of the recording period for the array of bipolar EGMs. If the running window has reached the end, or there are no remaining valid peaks, then the direction of wave propagation has been identified and can be stored at 1635. Method 1600 would then end at 1635. The stored identified propagating waves and the direction of all the propagating waves may then be sent to another device or output on a display or otherwise reported to a user.

If there are remaining valid peaks, then the running window is shifted along the time period of the recording until the next valid periodic peak is detected at 1630. As will be understood by a person skilled in the art, the shifting of the running window will be dependent on the sampling resolution of the EGMs being analyzed. Once the next valid periodic peak is detected, the current sequence is again analyzed at 1610 to determine if the direction of the next propagating wave can be determined.

In some cases, methods 1400-1600 may also be applied to detect rotors. Rotors are propagating waves with a circular or rotational direction. Rotors have been implicated in sustaining arrhythmias such as AF. To detect a rotor, the array of bipolar EGMs must be recorded simultaneously using a multi-electrode catheter or an equivalent recording device, whose array of electrodes permit sensing of circular or rotating wave propagation. For example, a multi-electrode circular catheter or a multi-electrode basket catheter capable of sensing circular or rotating propagation may be used.

To detect rotors using the results of methods 1400-1600, additional criteria may also be applied. For instance, in some embodiments two additional criteria can be applied to propagating waves in order to detect the presence of a rotor. The first such criteria may be that a valid periodic peak at the end of the running window (whose duration equals the periodicity cycle length) is followed by a valid periodic peak at the beginning of the next running window, whose duration equals the periodicity cycle length. The second such criteria may be that the valid periodic peaks across all bipolar EGMs in a particular sequence must cover more than a rotor threshold amount of the periodicity cycle length, for example 90% of the periodicity cycle length. These two criteria ensure that the direction of wave propagation is inscribed entirely by the bipolar EGMs of the multielectrode catheter and that if the array of such bipolar EGMs is arranged to sense circular or rotational wave propagation, then such wave propagation may be identified as from a rotor.

Figure 26:
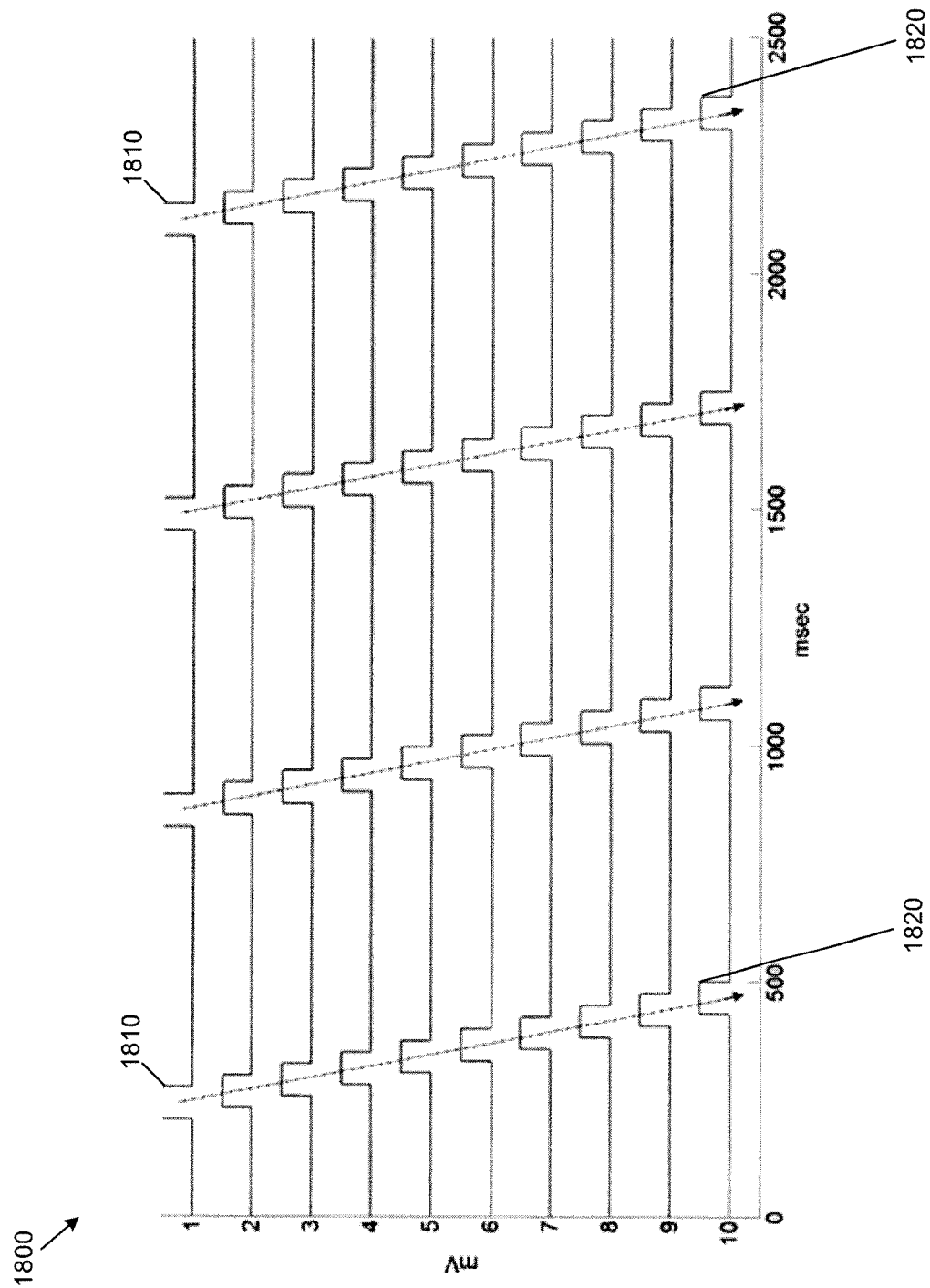
FIG. 26 is a diagram illustrating an example plot of a propagating wave pattern along 10 different recording sites, each manifesting periodic peaks.

Referring now to FIG. 26, shown therein is an example plot 1800 of an identified propagating wave whose direction corresponds to the temporal sequence of the array of 10 simulated periodic peaks of similar periodicity cycle length. The onset of each periodic peak in each of the 10 signals is varied, such that they are not simultaneous.

The periodic peaks for each signal associated with the similar periodicity cycle length were identified, and then the peaks were temporally sorted from those having the earliest peaks 1810 shown in the top row to those having the latest peaks 1820 shown in the bottom row. Thus, the direction of the propagating wave was from the top row signal to the bottom row signal. The method 1300 of identifying the direction of wave propagation described herein may be applied to a set of bipolar EGMs recorded simultaneously, for example for signals recorded using a multi-electrode catheter.

Figure 27:
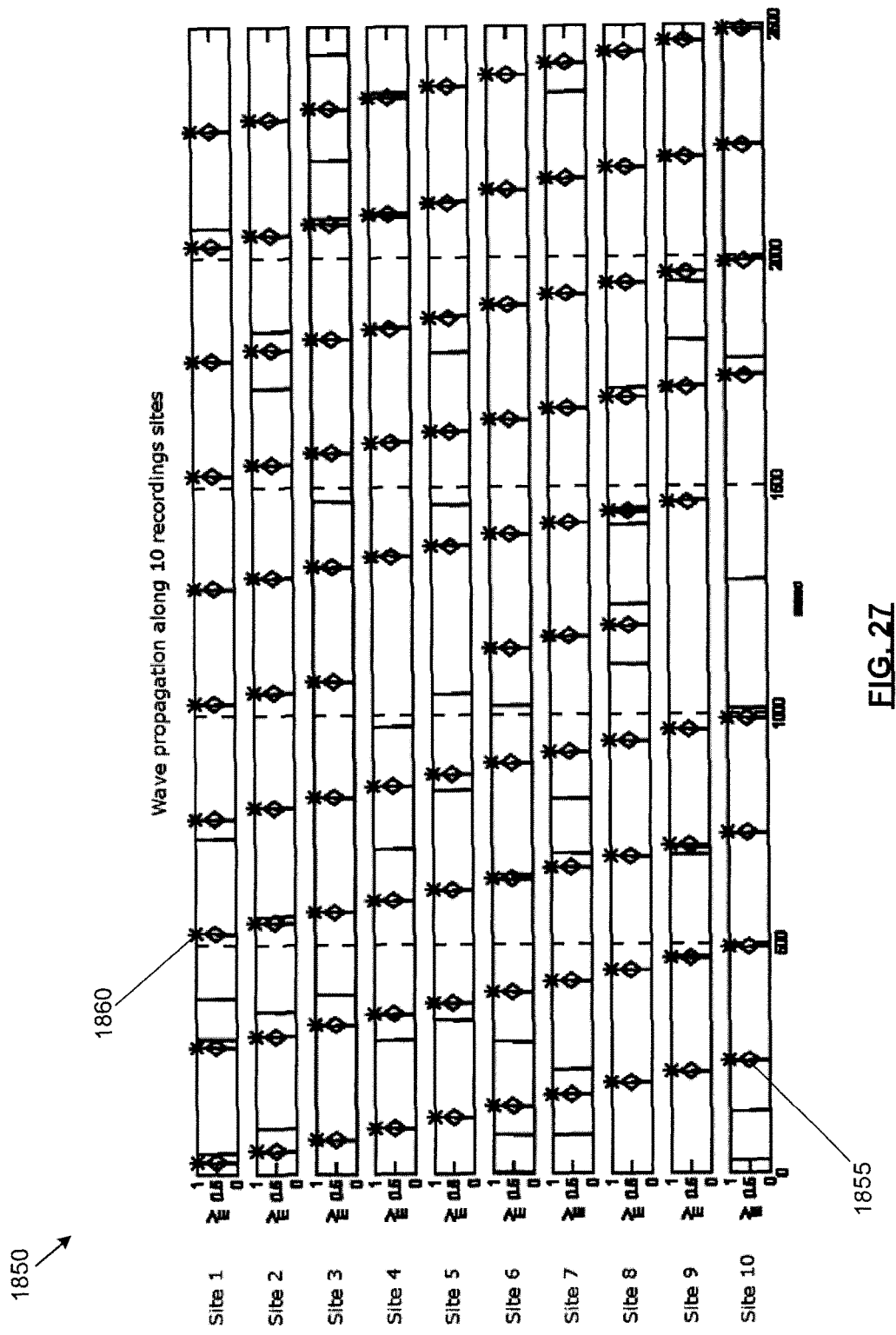
FIG. 27 is a diagram illustrating another example plot of a propagating wave pattern along 10 different recording sites, each manifesting periodic peaks, aperiodic peaks, and temporal periodic peak instability.

Referring now to FIG. 27, shown therein is a plot 1850 showing simulated periodic peaks over 2.5 seconds in 10 recording sites (Site 1 to 10), corresponding to 10 recording sites using a multi-electrode recording catheter. In the simulated plot 1850, each periodic peak propagates from one recording site to the next indicating the direction of wave propagation. In each recording site, the periodic peak is contaminated by 5 aperiodic peaks which are randomly positioned and the periodic peak is also randomly truncated to simulate temporal instability.

The periodic peaks 1855 identified by the methods described in accordance with the teachings herein are indicated in the plot 1850 by the diamonds. The asterisks indicate periodic peaks 1860 identified as forming a constituent of a propagating wave. In the example shown in plot 1850, the wave threshold for detecting the direction of a propagating wave was set to 70%. In other words, a running window, whose duration is equal to the periodicity cycle length, with a sequence of valid peaks from 7 or more of the recording sites may permit the direction of wave propagation to be determined. In contrast, when the running window begins at 1000 ms in FIG. 27, the direction of wave propagation cannot be determined because a sequence of 7 periodic peaks from the recording sites is not present within the duration of the running window.

Table 6 below shows the performance of the methods described in accordance with the teachings herein in detecting periodic peaks that comprise a propagating wave with linear directionality. Periodic peaks across 10 simulated recording sites (simulating a linear multi-electrode catheter) were staggered temporally to simulate a linear propagating wave. The set of 10 local periodic peaks was repeated every 250 ms (i.e. with a periodicity cycle length of 250 ms) over 2.5 s. In addition, 3 or 5 aperiodic peaks were randomly introduced into each recording site to contaminate the signal.

The simulation was repeated 350 times, and each time the location of the aperiodic peaks and temporal stability of the periodic peaks was varied randomly. The sensitivity and specificity of detecting all the local periodic peaks that comprise the propagating wave were calculated and are shown in Table 6 below. A sensitivity of 100% would indicate that all periodic peaks were detected, while a specificity of 100% would indicate that false detection of periodic peaks did not occur. As Table 6 illustrates, the methods described in accordance with the teachings herein show very good sensitivity and specificity even when the signals are contaminated with 5 aperiodic peaks.

TABLE 6

Performance of the methods described herein in detecting local periodic peaks that comprise a linear propagating wave

| | No. of Aperiodic Activations | |
|---|---|---|
| | 3 | 5 |
| Sensitivity (%) | 99 | 99 |
| Specificity (%) | 98 | 97 |

Table 7 shows the performance of the methods described in accordance with the teachings herein in detecting local peaks indicative of a rotor or rotating wave. Local periodic peaks across 10 simulated recording sites, simulating a multi-electrode circular catheter were staggered temporally to simulate a rotating wave. The set of 10 local periodic peaks was repeated every 250 ms (i.e. with a periodicity cycle length of 250 ms) over 2.5 s. In addition, 3 or 5 aperiodic activations were randomly introduced into each recording site to contaminate the signal.

The simulation was repeated 350 times, and each time the location of the aperiodic peaks and temporal stability of the periodic peaks was varied randomly. The sensitivity and specificity of detecting all periodic peaks that comprise the rotor were calculated and are shown in Table 7. A sensitivity of 100% would indicate that all periodic peaks were detected, while a specificity of 100% would indicate that false detection of periodic peaks did not occur. Again, the methods described in accordance with the teachings herein show good sensitivity and specificity even when the signals are contaminated with 5 aperiodic peaks.

TABLE 7

Performance of the described methods in detecting local activation peaks that comprise a rotor

|  | No. of Aperiodic Activations | |
| --- | --- | --- |
|  | 3 | 5 |
| Sensitivity (%) | 93 | 91 |
| Specificity (%) | 97 | 92 |

Various embodiments of methods for detecting peaks corresponding to the dominant periodicity in a periodic signal have been described in accordance with the teachings herein. These methods were compared against state-of-the-art peak detection algorithms using artificial AF data and were shown to perform favorably in comparison. The methods taught herein may be applied to the detection of focal electrical sources using a combination of bipolar and unipolar EGMs. These methods may be applied with real-time electrophysiological signals during AF to guide therapy, such as catheter ablation.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A method of identifying one or more focal source locations of electrophysiological activity for a heart using intracardiac electrograms of the heart, the method comprising:
   receiving, by a processor, a first electrical signal set obtained from a first location of the heart, the electrical signal set comprising electrophysiological signals acquired at the first location of the heart, wherein the electrical signal set comprises a unipolar electrogram and a bipolar electrogram;
   determining, by the processor, that the first electrical signal set is periodic;
   identifying, by the processor, a periodicity cycle length of the first electrical signal set when the first electrical signal set is periodic;
   automatically identifying, by the processor, a plurality of peaks in the bipolar electrogram of the first electrical signal set that are associated with the identified periodicity cycle length;
   for a given peak in the identified plurality of peaks, analyzing a peak morphology by:
      automatically identifying, by the processor, a unipolar electrogram portion in the unipolar electrogram corresponding to the given peak; and
      analyzing the identified unipolar electrogram portion to identify the peak morphology of the given peak;
   identifying, by the processor, the first location in the heart as a first focal source location of the one or more focal source locations when the identified periodicity cycle length and the identified plurality of peaks have focal source characteristics, wherein the focal source characteristics comprise at least a threshold percentage of peak morphologies in the first electrical signal set associated with the identified plurality of peaks having a QS morphology;
   determining, by the processor, an anatomic location of the first focal source location within the heart using anatomic mapping data from an electroanatomic mapping system;
   generating, by the processor, a 3D image of the heart that includes a tag identifying the anatomic location of the first focal source location within the 3D image using the electroanatomic mapping system; and
   displaying the 3D image of the heart including the tag to guide ablation of the first focal source location in the heart that corresponds to the tag shown in the 3D image.

2. The method as defined in claim 1, wherein the focal source characteristics comprise at least one of:
   the identified plurality of peaks being stable; and
   the identified periodicity cycle length being less than a periodicity cycle length threshold.

3. The method as defined in claim 2, wherein determining that the identified plurality of peaks is stable comprises:
   determining that a number of consecutive peaks in the plurality of peaks are spaced apart by a stable distance substantially equal to the periodicity cycle length; and
   determining that the number of consecutive peaks is larger than a consecutive peak threshold.

4. The method as defined in claim 1, wherein identifying the periodicity cycle length comprises:
   identifying a plurality of potential cycle lengths;
   determining a plurality of correlation values corresponding to the plurality of potential cycle lengths; and
   identifying the periodicity cycle length as the potential cycle length having an optimal correlation value.

5. The method as defined in claim 4, wherein determining a given correlation value for a corresponding potential cycle length comprises:
   identifying a first signal portion of the first electrical signal set;
   generating a second signal portion from the first electrical signal set by applying a circular shift to the first signal portion, the shift being the potential cycle length; and
   determining the correlation value between the first signal portion and the second signal portion.

6. The method as defined in claim 4, wherein determining a given correlation value for a corresponding potential cycle length comprises determining a cost value of the corresponding potential cycle length.

7. The method as defined in claim 4, wherein determining that the first electrical signal set is periodic further comprises determining that the optimal correlation value differs from a mean correlation value by more than a threshold correlation value.

8. The method as defined in claim 7, wherein the threshold correlation value is a predefined amount based on a standard deviation of the plurality of correlation values.

9. The method as defined in claim 1, wherein identifying the plurality of peaks in the first electrical signal set comprises:
   identifying a plurality of potential peaks in the first electrical signal set;

determining a plurality of potential peak distances, each potential peak distance corresponding to a distance in the first electrical signal set between two of the potential peaks;

determining a plurality of potential peak costs, each potential peak cost corresponding to one of the potential peak distances;

identifying a plurality of subsets of potential peaks from the plurality of potential peaks;

determining the peak cost measure for each subset of potential peaks; and identifying the plurality of peaks based on the subset of potential peaks having a lowest peak cost measure.

10. The method as defined in claim 9, wherein identifying the plurality of potential peaks in the first electrical signal comprises:

identifying a peak threshold; and identifying the plurality of potential peaks in the first electrical signal set by finding peaks in the first electrical signal set having an amplitude that is larger than the peak threshold.

11. The method as defined in claim 9, wherein each of the potential peak costs is determined based on a difference between the corresponding potential peak distance and the identified periodicity cycle length.

12. The method as defined in claim 9, wherein the peak cost measure is determined based on a sum of the potential peak costs corresponding to the peaks in the subset of potential peaks.

13. The method as defined in claim 9, wherein identifying the plurality of peaks based on the subset of potential peaks having the lowest peak cost measure comprises:

identifying a pruned subset of peaks by removing each of the peaks in the subset of potential peaks that are not within a peak threshold distance of an adjacent peak; and identifying the plurality of peaks as the pruned subset of peaks.

14. The method as defined in claim 13, wherein the peak threshold distance is determined based on the identified periodicity cycle length.

15. The method as defined in claim 1, wherein the percentage of peak morphologies is such that the expected morphology is found for a majority of the identified unipolar electrogram portions.

16. The method as defined in claim 1, further comprising:

receiving, by the processor, a plurality of additional electrical signal sets, each of the additional electrical signal sets being obtained from different locations in the heart;

determining, by the processor, that a given additional electrical signal set is periodic;

identifying, by the processor, an additional periodicity cycle length for the given additional electrical signal set;

identifying, by the processor, a plurality of additional peaks in the given additional electrical signal set that are associated with the identified additional periodicity cycle length; and identifying, by the processor, an additional location in the heart corresponding to the given additional electrical signal set as an additional focal source location when the additional identified periodicity cycle length and the identified plurality of additional peaks have the focal source characteristics.

17. The method as defined in claim 16, further comprising:

identifying the additional location as the additional focal source location when the additional periodicity cycle length is less than the periodicity cycle length threshold.

18. The method as defined in claim 17, further comprising:

determining a periodicity cycle length distribution based on the additional periodicity cycle lengths identified for each of the additional electrical signal sets; and identifying the periodicity cycle length threshold based on the periodicity cycle length distribution.

19. The method as defined in claim 1, wherein the electrophysiological activity is atrial fibrillation or ventricular fibrillation.

20. A method of identifying a direction of a propagating wave based on one or more focal source locations of electrophysiological activity for a heart using intracardiac electrograms of the heart, the method comprising:

receiving, by a processor, a plurality of electrical signal sets obtained substantially simultaneously from a plurality of locations of the heart, each electrical signal set comprising electrophysiological signals acquired at a corresponding location of the heart, wherein each electrical signal set comprises a unipolar electrogram and a bipolar electrogram acquired from the heart;

identifying, by the processor, a first subset of the plurality of electrical signal sets having periodicity;

determining, by the processor, periodicity cycle lengths for the first subset of electrical signal sets that have periodicity;

identifying, by the processor, a second subset of electrical signal sets having similar periodicity cycle lengths in the first subset of electrical signal sets;

identifying, by the processor, for each electrical signal set in the second subset of electrical signal sets, a plurality of valid peaks in the bipolar electrogram for that electrical signal set;

determining, by the processor, that the plurality of valid peaks in the bipolar electrograms of the electrical signal sets in the second subset of electrical signal sets have propagating wave characteristics;

sorting, by the processor, the valid peaks to identify the direction of the propagating wave when the plurality of valid peaks have propagating wave characteristics;

identifying, by the processor, an earliest activation location from the sorted valid peaks, wherein the earliest activation location is determined to be the bipolar electrogram in which the earliest valid peak is identified;

determining, by the processor, an anatomic location of the earliest activation location within the heart using anatomic mapping data from an electroanatomic mapping system;

generating, by the processor, a 3D image of the heart that includes a tag identifying the anatomic location of the earliest activation location within the 3D image using the electroanatomic mapping system; and displaying the 3D image of the heart including the tag to guide ablation of the earliest activation location in the heart that corresponds to the tag shown in the 3D image.

21. The method of claim 20, wherein sorting the valid peaks comprises sorting the second subset of electrical signal sets in order of increasing activation time defined by timing of the identified plurality of valid peaks for each electrical signal set in the second subset of electrical signal sets.

22. The method of claim 20, wherein the plurality of valid peaks have propagating wave characteristics when the plurality of valid peaks comprise a sequence of valid peaks within a running window, the running window corresponding to the similar periodicity cycle lengths of the plurality of peaks in the second subset of electrical signal sets, and the sequence of valid peaks comprises a number of valid peaks greater than a wave threshold.

23. The method of claim 22, wherein the wave threshold is defined based on a proportion of the electrical signal sets in the second subset.

24. The method of claim 20, wherein identifying the plurality of valid peaks for each electrical signal set in the second subset of electrical signal sets comprises, for each electrical signal set:
 identifying a plurality of potential peaks in that electrical signal set corresponding to the similar periodicity cycle length;
 identifying a plurality of stable peaks for that electrical signal set as the potential peaks that are stable; and
 identifying the plurality of valid peaks for that electrical signal set as a valid subset of the plurality of stable peaks that satisfy validation criteria.

25. A method of identifying multiple significant periodicities in an electrical signal set representing electrophysiological activity for a heart using intracardiac electrograms of the heart, the method comprising:
 receiving, by a processor, the electrical signal set obtained from a location of the heart, the electrical signal set comprising electrophysiological signals acquired at the first location of the heart, wherein the electrical signal set comprises a unipolar electrogram and a bipolar electrogram;
 identifying, by the processor, a periodicity cycle length of the electrical signal set;
 automatically determining, by the processor, a plurality of peaks in the bipolar electrogram of the electrical signal set that are associated with the identified periodicity cycle length;
 for a given peak in the identified plurality of peaks, analyzing a peak morphology by:
  automatically identifying, by the processor, a unipolar electrogram portion in the unipolar electrogram corresponding to the given peak; and
  analyzing the identified unipolar electrogram portion to identify the peak morphology of the given peak;
 noting, by the processor, the identified periodicity cycle length;
 generating, by the processor, an updated electrical signal set by removing information associated with the identified periodicity cycle length;
 repeating the identifying, determining, analyzing, noting and generating acts until no periodicity is detected in the updated electrical signal set;
 identifying, by the processor, the location of the heart as a focal source location when any of the identified periodicity cycle lengths and corresponding plurality of peaks have focal source characteristics, wherein the focal source characteristics comprise at least a threshold percentage of peak morphologies in the first electrical signal set associated with the identified plurality of peaks having a QS morphology;
 determining, by the processor, an anatomic location of the focal source location within the heart using anatomic mapping data from an electroanatomic mapping system;
 generating, by the processor, a 3D image of the heart that includes a tag identifying the anatomic location of each focal source location within the 3D image using the electroanatomic mapping system; and
 displaying the 3D image of the heart including the tag of the anatomic location of each focal source location to guide ablation of the each focal source location in the heart that corresponds to each tag shown in the 3D image.

26. The method of claim 25 wherein generating the updated electrical signal set comprises blanking a plurality of portions from the electrical signal set corresponding to the determined plurality of peaks.

* * * * *